(12) United States Patent
Rowlinson

(10) Patent No.: US 12,331,335 B2
(45) Date of Patent: Jun. 17, 2025

(54) METHODS FOR PRODUCTION OF HUMAN RECOMBINANT ARGINASE 1 AND USES THEREOF

(71) Applicant: Immedica Pharma AB, Stockholm (SE)

(72) Inventor: Scott W. Rowlinson, Austin, TX (US)

(73) Assignee: Immedica Pharma AB, Stockholm (SE)

( * ) Notice: Subject to any disclaimer, the term of this patent is extended or adjusted under 35 U.S.C. 154(b) by 0 days.

(21) Appl. No.: 18/338,255

(22) Filed: Jun. 20, 2023

(65) Prior Publication Data
US 2024/0110172 A1  Apr. 4, 2024

Related U.S. Application Data

(63) Continuation of application No. 17/006,383, filed on Aug. 28, 2020, now abandoned.

(60) Provisional application No. 62/894,319, filed on Aug. 30, 2019.

(51) Int. Cl.
| C12N 9/78 | (2006.01) |
| C07K 1/18 | (2006.01) |
| C07K 1/36 | (2006.01) |
| C12N 1/06 | (2006.01) |

(52) U.S. Cl.
CPC .............. *C12N 9/78* (2013.01); *C07K 1/18* (2013.01); *C07K 1/36* (2013.01); *C12N 1/06* (2013.01); *C12Y 305/03001* (2013.01)

(58) Field of Classification Search
None
See application file for complete search history.

(56) References Cited

U.S. PATENT DOCUMENTS

| 5,889,155 | A  | 3/1999  | Ashkenazi et al. |
| 6,316,199 | B1 | 11/2001 | Vockley et al. |
| 7,229,962 | B2 | 6/2007  | Chung et al. |
| 8,398,968 | B2 | 3/2013  | Mayall |
| 8,440,184 | B2 | 5/2013  | Georgiou et al. |
| 8,679,479 | B2 | 3/2014  | Georgiou et al. |
| 9,050,340 | B2 | 6/2015  | Georgiou et al. |
| 9,109,218 | B2 | 8/2015  | Cheng et al. |
| 9,382,525 | B2 | 7/2016  | Leung et al. |
| RE46,423  | E  | 6/2017  | Georgiou et al. |
| 10,098,933 | B2 | 10/2018 | Georgiou et al. |
| 10,729,752 | B2 | 8/2020  | Lowe et al. |
| 11,717,562 | B2 | 8/2023  | Rowlinson et al. |
| 2002/0119554 | A1 | 8/2002  | Vockley et al. |
| 2005/0244398 | A1 | 11/2005 | Cheng et al. |
| 2008/0226617 | A1 | 9/2008  | Cheng et al. |
| 2008/0292609 | A1 | 11/2008 | Cheng et al. |
| 2009/0238813 | A1 | 9/2009  | Georgiou et al. |
| 2010/0111925 | A1 | 5/2010  | Georgiou et al. |
| 2010/0247508 | A1 | 9/2010  | Leung et al. |
| 2012/0177628 | A1 | 7/2012  | Georgiou et al. |
| 2013/0273022 | A1 | 10/2013 | Georgiou et al. |
| 2014/0023628 | A1 | 1/2014  | Leung et al. |
| 2014/0112902 | A1 | 4/2014  | Foster et al. |
| 2014/0154797 | A1 | 6/2014  | Godfrin |
| 2014/0242060 | A1 | 8/2014  | Georgiou et al. |
| 2014/0363417 | A1 | 12/2014 | Cheng et al. |
| 2015/0010522 | A1 | 1/2015  | Cheng et al. |
| 2016/0095884 | A1 | 4/2016  | Godfrin et al. |
| 2016/0161485 | A1 | 6/2016  | Chu et al. |
| 2017/0128553 | A1 | 5/2017  | Georgiou et al. |
| 2017/0191078 | A1 | 7/2017  | Zhang et al. |
| 2017/0224843 | A1 | 8/2017  | Deglon et al. |
| 2017/0240922 | A1 | 8/2017  | Gill et al. |
| 2017/0283830 | A1 | 10/2017 | Saltzman et al. |
| 2018/0177853 | A1 | 6/2018  | Lowe et al. |
| 2018/0271960 | A1 | 9/2018  | Cheng et al. |
| 2019/0000939 | A1 | 1/2019  | Georgiou et al. |
| 2019/0167770 | A1 | 6/2019  | Rowlinson et al. |
| 2020/0360493 | A1 | 11/2020 | Lowe et al. |
| 2021/0128703 | A1 | 5/2021  | Georgiou et al. |
| 2021/0189371 | A1 | 6/2021  | Rowlinson |
| 2021/0379167 | A1 | 12/2021 | Quinn et al. |
| 2024/0009283 | A1 | 1/2024  | Georgiou et al. |
| 2024/0009284 | A1 | 1/2024  | Rowlinson et al. |

FOREIGN PATENT DOCUMENTS

| CA | 3073116 A1    | 2/2019  |
| CN | 103184208 A   | 7/2013  |
| CN | 105112391 A   | 12/2015 |
| EP | 1803465 A1    | 7/2007  |
| EP | 2799539 A1    | 11/2014 |
| JP | H02117383 A   | 5/1990  |

(Continued)

OTHER PUBLICATIONS

Aeglea Biotherapeutics, "Aeglea Biotherapeutics to Present Topline Data from Phase 1 Trial of Aeb11 02 for Treatment of Arginase I Deficiency at 2017 ACMG Annual Clinical Genetics Meeting," Press release, retrieved online at: ir.aegleabio.com/news-releases/news-release-details/aeglea-biotherapeutics-present-topline-data-phase-1-trial, Mar. 23, 2017, 3 pages.

Agnello et al., "Preclinical safety and antitumor activity of the arginine-degrading therapeutic enzyme pegzilarginase, a PEGylated, cobalt-substituted recombinant human arginase 1", Transl Res. Mar. 2020: 217: 11-22. Epub Dec. 27, 2019.

Allen, L. et al., eds., "Ansel's Pharmaceutical Dosage Forms and Drug Delivery Systems," 8th ed. Lippincott, 2005, excerpt, pp. 51, 53, 54, 92-94, 162-164, 169, and 182-184. 16 printed pages.

Amayreh, W. et al., "Treatment of arginase deficiency revisited: guanidinoacetate as a therapeutic target and biomarker for therapeutic monitoring," Dev Med Child Neurol. Oct. 2014; 56(10): 1021-4. Epub May 10, 2014.

(Continued)

*Primary Examiner* — Suzanne M Noakes
(74) *Attorney, Agent, or Firm* — COOLEY LLP

(57) ABSTRACT

Described are methods for producing recombinant Arginase, such as PEGylated, cobalt-substituted recombinant human Arginase 1. Also described are pharmaceutical compositions comprising such recombinant Arginase, as well as methods of treatment and uses of such recombinant Arginase.

16 Claims, 35 Drawing Sheets

Specification includes a Sequence Listing.

(56) References Cited

FOREIGN PATENT DOCUMENTS

| JP | 2015503912 A | 2/2015 |
|---|---|---|
| WO | WO-03063780 A2 | 8/2003 |
| WO | WO-2004001048 A1 | 12/2003 |
| WO | WO-2010051533 A2 | 5/2010 |
| WO | WO-2010124547 A1 | 11/2010 |
| WO | WO-2011008495 A2 | 1/2011 |
| WO | WO-2012061015 A2 | 5/2012 |
| WO | WO-2012085793 A1 | 6/2012 |
| WO | WO-2015164743 A2 | 10/2015 |
| WO | WO-2016033555 A1 | 3/2016 |
| WO | WO-2017192449 A1 | 11/2017 |
| WO | WO-2018032020 A1 | 2/2018 |
| WO | WO-2019035935 A1 | 2/2019 |
| WO | WO-2019113157 A1 | 6/2019 |
| WO | WO-2019228510 A1 | 12/2019 |
| WO | WO-2020081994 A1 | 4/2020 |
| WO | WO-2021041904 A1 | 3/2021 |
| WO | WO-2021202957 A1 | 10/2021 |
| WO | WO-2021257523 A1 | 12/2021 |
| WO | WO-2023201228 A1 | 10/2023 |

OTHER PUBLICATIONS

Ankudinov, A. L., et al., "Real-space Multiple-scattering Calculation and Interpretation of X-ray-absorption Near-edge Structure," Physical Review B, 58: 7565-7576, 1998.

Aoki S, et al., "Guanidine is a Zn(2+)-binding ligand at neutral pH in aqueous solution," J Am Chem Soc. May 15, 2002; 124(19): 5256-7.

Ascierto, P. A., et al., "Pegylated arginine deiminase treatment of patients with metastatic melanoma: results from phase I and II studies," J Clin Oncol. Oct. 20, 2005; 23(30): 7660-8.

Ash, D. E., "Structure and function of Arginases," J Nutr. Oct. 2004; 134(10 Suppl): 2760S-2764S; discussion 2765S-2767S. 5 printed pages.

ATS Committee on Proficiency Standards for Clinical Pulmonary Function Laboratories, "ATS Statement Guidelines for the Six-Minute Walk," Am J Respir Crit Care Med. Jul. 1, 2002; 166(1): 111-7.

Auld, D. S. & Vallee, B. L., "Kinetics of Carboxypeptidase A. The PH Dependence of Tripeptide Hydrolysis Catalyzed by Zinc, Cobalt, and Manganese Enzymes," Biochemistry, 9:4352-4359, 1970.

Aulton, M., ed., "Pharmaceutics: The Design and Manufacture of Medicines," Elsevier, 2007, excerpt, pp. 4, 5, 286, and 324. 5 printed pages.

Badarau A, et al., "The Variation of Catalytic Efficiency of Bacillus Cereus Metallo-beta-lactamase with Different Active Site Metal Ions," Biochemistry. Sep. 5, 2006; 45(35): 10654-66.

Badeaux et al., "Arginase Therapy Combines Effectively with Immune Checkpoint Blockade or Agonist Anti-0X40 Immunotherapy to Control Tumor Growth," Cancer Immunology Research, vol. 9, No. 4, Apr. 1, 2021 (Apr. 1, 2021), pp. 415-429.

Bansal, V., et al., "Arginine Availability, Arginase, and the Immune Response," Curr Opin Clin Nutr Metab Care. Mar. 2003; 6(2): 223-8.

Beale R N & Croft D., "A Sensitive Method for the Colorimetric Determination of Urea," J. Clin. Pathol., 14: 418-24, 1961.

Becht H et al., "Induction of an Arginine-rich Component during Infection with Influenza Virus", Journal of General Virology, vol. 4, No. 2, Mar. 1, 1969, pp. 215-220.

Bewley et al., "Crystal Structures of Bacillus Caldovelox Arginase in Complex with Substrate and Inhibitors Reveal New Insights into Activation, Inhibition and Catalysis in the Arginase Superfamily," Structure, 7: 435-448, 1999.

Bicker and Thompson "The protein arginine deiminases (PADs): Structure, Function, Inhibition, and Disease," Biopolymers. Feb. 2013; 99(2): 155-163.

Bickmore et al., "Bond-valence Methods for Pka Prediction. Ii. Bond-valence, Electrostatic, Molecular Geometry, And Solvation Effects," Geochimica Et Cosmochimica Acta, 70: 4057-4071, 2006.

Braissant, "GAMT deficiency: 20 years of a treatable inborn error of metabolism", Mol Genet Metab. Jan. 2014; 111(1): 1-3. Epub Nov. 10, 2013.

Burrage, L.C. et al., "Human recombinant arginase enzyme reduces plasma arginine in mouse models of arginase deficiency," Human Molecular Genetics, vol. 24, No. 22, 2015, pp. 6417-6427.

Caldwell, R. William et al., "Arginase: A Multifaceted Enzyme Important in Health and Disease," Physiol Rev. Apr. 1, 2018; 98(2): 641-665.

Cama et al., "Structural And Functional Importance of First-shell Metal Ligands in the Binuclear Manganese Cluster of Arginase 1," Biochemistry. Jul. 1, 2003; 42(25): 774858.

Carvajal et al., "Consequences of Mutations of Metal Ligands in Human Liver Arginase 1," Molecular Biology of the Cell, 13: 546A, 2002. 1 page.

Carvajal et al., Interaction of Arginase with Metal Ions: Studies of the Enzyme from Human Liver and Comparison with Other Arginases, Camp Biochem Physiol B Biochem Mol Bioi, 112: 153-159, 1995.

Carvalho, D.R., et al., "Clinical features and neurologic progression of hyperargininemia," Pediatr. Neural., 46(6): 369-74 (2012).

Cavalli et al., "Mutagenesis of Rat Liver Arginase Expressed in *Escherichia coli*: Role of Conserved Histidines," Biochemistry. Sep. 6, 1994; 33(35): 10652-7.

Cellarier et al., "Methionine Dependency and Cancer Treatment," Cancer Treat. Rev., 29: 489-499, 2003.

Chaberek et al., "Stability Of Metal Chelates. II. B-hydroxyethyliminodiacetic Acid," J Am. Chem. Soc., 74: 5057-60, 1952.

Cheng et al., "Enhanced hepatocyte growth factor signaling by type II transforming growth factor-beta receptor knockout fibroblasts promotes mammary tumorigenesis," Cancer Res., 67: 4869-4877, 2007.

Cheng et al., "Pegylated recombinant human arginase (rhArg-peg5,000mw) inhibits the in vitro and in vivo proliferation of human hepatocellular carcinoma through arginine depletion," Cancer Res. Jan. 1, 2007; 67(1): 309-17.

Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma," Cancer Lett. Jun. 16, 2005; 224(1): 67-80. Epub Dec. 25, 2004.

Christianson and Cox, "Catalysis by metal-activated hydroxide in zinc and manganese metalloenzymes," Annu Rev Biochem. 1999: 68: 33-57.

Christianson and Fierke, "Carbonic anhydrase: evolution of the zinc binding site by nature and by design," Ace. Chem. Res., 29: 331-339, 1996.

Colleluori et al., "Expression, purification, and characterization of human type II arginase," Arch Biochem Biophys. May 1, 2001; 389(1): 135-43.

Colleluori et al. "Probing the role of the hyper-reactive histidine residue of Arginase," Arch Biochem Biophys. Dec. 1, 2005; 444(1): 15-26. Epub Oct. 13, 2005. 12 pages.

Compaan, D.M. et al., "The crystal structure of the costimulatory OX40-OX40L complex," Structure. Aug. 2006; 14(8): 1321-30.

Das S. C. et al., "The Highly Conserved Arginine Residues at Positions 76 through 78 of Influenza A Virus Matrix Protein M1 Play an Important Role in Viral Replication by Affecting the Intracellular Localization of MI", Journal of Virology, vol. 86, No. 3, Nov. 16, 2011, pp. 1522-1530.

Deignan et al., "Increased plasma and tissue guanidine compounds in a mouse model of hyperargininemia," Mol. Genet. Metab. 93: 172-178, 2008.

Di Costanzo et al., "Stereochemistry of guanidine-metal interactions: implications for L-arginine-metal interactions in protein structure and function," Proteins. Nov. 15, 2006; 65(3): 637-42.

(56) References Cited

OTHER PUBLICATIONS

Dillon et al., "Biochemical characterization of the arginine degrading enzymes arginase and arginine deiminase and their effect on nitric oxide production", Med Sci Monit. Jul. 2002; 8(7): BR248-53. 7 pages.
Dinndorf et al., "FDA Drug Approval Summary: Pegaspargase (Oncaspar) for the First-line Treatment of Children with Acute Lymphoblastic Leukemia All)," Oncologist, 12: 991-998, 2007.
Dowling et al., "Evolution of the arginase fold and functional diversity," Cell Mol Life Sci. Jul. 2008; 65(13): 2039-55.
Downs, Stephen, "The Berg Balance Scale", J Physiother. Jan. 2015; 61(1): 46. Epub Dec. 1, 2014. 1 page.
Durante et al., "Arginase: a critical regulator of nitric oxide synthesis and vascular function," Clin Exp Pharmacol Physiol. Sep. 2007; 34(9): 906-11.
Dwight L. McKee et al., "Candidate drugs against SARS-CoV-2 and COVID-19", Pharmacological Research., vol. 157, Jan. 1, 2020 (Jan. 1, 2020), p. 104859.
Enright et al., "Reference equations for the six-minute walk in healthy adults," Am. J. Respir. Grit. Care Med., 1998 158(5 Pt 1): 1384-1387.
Ensor et al., "Pegylated arginine deiminase (ADI-SS PEG20,000 mw) inhibits human melanomas and hepatocellular carcinomas in vitro and in vivo," Cancer Res. Oct. 1, 2002; 62(19): 5443-50.
Feun et al., "Clinical trial of CP 1-11 and VM-26/VP-16 for patients with recurrent malignant brain tumors," J Neurooncol. Apr. 2007; 82(2): 177-81. Epub Oct. 19, 2006.
Final Office Action for U.S. Appl. No. 13/863,448 dated Oct. 22, 2014, 6 pages.
Final Office Action for U.S. Appl. No. 16/210,248 dated Apr. 6, 2021, 8 pages.
Fletcher et al., "I-Arginine depletion blunts antitumor T-cell responses by inducing myeloid-derived suppressor cells," Cancer Res. Jan. 15, 2015; 75(2): 275-83. Epub Nov. 18, 2014.
Fultang L , et al., "Molecular Basis and Current Strategies of Therapeutic Arginine Depletion for Cancer", International Journal of Cancer, Val. 139, No. 3, Apr. 15, 2016 (Apr. 15, 2016), pp. 501-509.
Geiger et al., "Six-minute walk test in children and adolescents", J Pediatr. Apr. 2007; 150(4): 395-9, 399.e1-2. 6 pages.
Gill and Von Hippel, "Calculation of protein extinction coefficients from amino acid sequence data," Anal Biochem. Nov. 1, 1989; 182(2): 319-26.
Glazer, E., et al., "Bioengineered Human Arginase I with Enhanced Activity and Stability Controls Hepatocellular and Pancreatic Carcinoma Xenografts," Translational Oncology, 2011, 4(3): 138-146.
Grimes et al., "Arginine depletion as a therapeutic approach for patients with COVID-19", International Journal of Infectious Diseases, International Society for Infectious Diseases, Hamilton, CA, vol. 102, 4 Nov. 4, 2020, pp. 566-570.
Haberle et al., "Suggested guidelines for the diagnosis and management of urea cycle disorders," Orphanet. J. Rare Dis., 2012 7: 32.
Han et al., "Synthesis and evaluation of alternative substrates for arginase," Bioorg Chern, 30: 81-94, 2002.
Haraguchi et al., "Molecular cloning and nucleotide sequence of cDNA for human liver arginase," Proc Natl Acad Sci USA. Jan. 1987; 84(2): 412-5.
Harris et al., "Pegylation: a novel process for modifying pharmacokinetics," Clin Pharmacokinet. 2001; 40(7): 539-51.
He et al., "Aminoguanidinium hydrolysis effected by a hydroxo-bridged dicobalt (II) complex as a functional model for arginase and catalyzed by mononuclear cobalt (II) complexes," J. Am. Chern. Soc., 120: 105-113, 1998.
Hernandez, C. P. et al., "Pegylated arginase I: a potential therapeutic approach in T-ALL," Blood. Jun. 24, 2010; 115(25): 5214-21. Epub Apr. 20, 2010.
Holtsberg et al., "Poly(ethylene Glycol) Peg) Conjugated Arginine Deiminase: Effects of Peg Formulations on Its Pharmacological Properties," Journal of Controlled Release, 80: 259-271, 2002.

Ikemoto et al., "Expression of Human Liver Arginase in *Escherichia coli*: Purification and Properties Ofthe Product," Biochem. J., 270: 697-703, 1990.
International Preliminary Report on Patentability for International Application No. PCT/US2018/063982, mailed Jun. 18, 2020, 9 pages.
International Preliminary Report on Patentability for International Application No. PCT/US2021/025509, mailed Oct. 13, 2022, 9 pages.
International Preliminary Report on Patentability for International Application No. PCT/US2021/037362, mailed Dec. 29, 2022, 8 pages.
International Preliminary Report on Patentability for International Patent Application No. PCT/US2017/050816, mailed Feb. 21, 2019. 11 pages.
International Preliminary Report on Patentability for PCT/US2019/062471 dated May 25, 2021, 7 pages.
International Preliminary Report on Patentability issued for International Application No. PCT/US2019/057027, mailed Apr. 29, 2021, 8 pages.
International Preliminary Report on Patentability Issued in International Application No. PCT/US2010/040205, mailed Jan. 12, 2012. 7 pages.
International Preliminary Report on Patentability received for International Application No. PCT/US2020/048536, mailed Mar. 10, 2022. 14 pages.
International Search Report and Written Opinion for International Application No. PCT/US2009/062969, mailed Jun. 17, 2010. 14 pages.
International Search Report and Written Opinion for International Application No. PCT/US2010/040205, mailed Mar. 25, 2011. 11 pages.
International Search Report and Written Opinion for International Application No. PCT/US2017/050816. mailed Dec. 28, 2017, 17 pages.
International Search Report and Written Opinion for International Application No. PCT/US2018/063982, mailed Feb. 28, 2019, 16 pages.
International Search Report and Written Opinion for International Application No. PCT/US2019/057027, mailed Apr. 2, 2020, 11 pages.
International Search Report and Written Opinion for International Application No. PCT/US2020/048536 dated Feb. 22, 2021, 22 pages.
International Search Report and Written Opinion for International Application No. PCT/US2021/021148 Jul. 28, 2021, 12 pages.
International Search Report and Written Opinion for International Application No. PCT/US2021/025509, mailed on Jul. 21, 2021, 13 pages.
International Search Report and Written Opinion for International Application No. PCT/US2021/037362, mailed on Sep. 24, 2021, 11 pages.
International Search Report and Written Opinion for International Application No. PCT/US2023/065630 dated Jul. 28, 2023, 9 pages.
Invitation to Pay additional fees received for International Application No. PCT/US2020/048536, mailed Nov. 5, 2020. 10 pages.
Irving and Williams, "Order of stability of metal complexes," Nature, 162: 746-747, 1948.
Izzo et al., "Pegylated arginine deiminase lowers hepatitis C viral titers and inhibits nitric oxide synthesis", J Gastroenterol Hepatol. Jan. 2007; 22(1): 86-91.
Izzo et al., "Pegylated arginine deiminase treatment of patients with unresectable hepatocellular carcinoma: results from phase 1/11 studies," J. Clin. Oncol., 22: 1815-1822, 2004.
Jefferis, "Antibody therapeutics: isotype and glycoform selection," Expert Opin Biol Ther. Sep. 2007; 7(9): 1401-13.
Jenkinson, Christopher P., et al., "Comparative properties of arginases," Comparative Biochemistry and Physiology Part B: Biochemistry and Molecular Biology (1996); 114(1): 107-132.
Jeon, H., et al., "Structure and Cancer Immunotherapy of the 87 Family Member B7x," Cell Reports, 2014, 9(3): 1089-1098.
Kalnine el al., Database GenBank Accession No. BT0199354, "Synthetic construct Homo sapiens arginase, type II mRNA, partial

(56) References Cited

OTHER PUBLICATIONS cds," NCBI Protein DB[online], Oct. 28, 2004 [retrieved on Aug. 16, 2013], URL: http://www.ncbi.nim.nih.~ov/nuccore/BT019935. 2 printed pages.
Kang J. et al., "Emerging PEGylated drugs," Expert Opin Emerg Drugs. Jun. 2009; 14(2): 363-80.
Katusic, Z., "Mechanisms of endothelial dysfunction induced by Aging: Role of Arginase 1", Circ Res. Sep. 28, 2007; 101(7): 640-1.
Kelly et at., "Arginine deiminase PEG20 inhibits growth of small cell lung cancers lacking expression of argininosuccinate synthetase," Br J Cancer. Jan. 17, 2012; 106(2): 324-32. Epub Dec. 1, 2011.
Khangulov et al., "L-arginine binding to liver arginase requires proton transfer to gateway residue His141 and coordination of the guanidinium group to the dimanganese(II,II) center," Biochemistry. Jun. 9, 1998; 37(23): 8539-50.
Knipp and Vasak, "A colorimetric 96-well microtiter plate assay for the determination of enzymatically formed citrulline," Anal Biochem. Nov. 15, 2000; 286(2): 257-64.
Kuhn et al., "pH-sensitive control of arginase by Mn(II) ions at submicromolar concentrations," Arch Biochem Biophys. Apr. 1991; 286(1): 217-21.
Lam, T. L., et al., "Recombinant human arginase inhibits proliferation of human hepatocellular carcinoma by inducing cell cycle arrest," Cancer Lett. May 8, 2009; 277(1): 91-100. Epub Jan. 12, 2009.
Lamb, J. & Wheatley, D. N., "Single Amino Acid Arginine) Deprivation Induces GI Arrest Associated with Inhibition of Cdk4 Expression in Cultured Human Diploid Fibroblasts," Exp Cell Res. Mar. 15, 2000; 255(2): 238-49.
Lambert et al., "Hyperargininemia: intellectual and motor improvement related to changes in biochemical data," J Pediatr. Mar. 1991; 118(3): 420-4.
Lastwika, K.J., et al., "Control of PD-L1 Expression by Oncogenic Activation of the AKT-mTOR Pathway in Non-Small Cell Lung Cancer," Cancer Research, vol. 76, No. 2, Dec. 4, 2015, pp. 227-238.
Lavulo et al., "Subunit-subunit interactions in trimeric arginase. Generation of active monomers by mutation of a single amino acid," J Biol Chem. Apr. 27, 2001; 276(17): 14242-8. Epub Jan. 24, 2001.
Lesterhuis, W.J., "Network analysis of immunotherapy-induced regressing tumours identifies novel synergistic drug combinations," Scientific Reports, Jul. 2015, 5: 12298. 11 pages printed.
Linch, S. N., et al., "OX40 Agonists and Combination Immunotherapy: Putting the Pedal to the Metal," Front Oncol. Feb. 16, 2015: 5: 34. eCollection 2015. 14 pages.
Lopez et al., "Insights into the interaction of human arginase II with substrate and manganese ions by site-directed mutagenesis and kinetic studies. Alteration of substrate specificity by replacement of Asn149 with Asp," FEBS J. Sep. 2005; 272(17): 4540-8.
Luneburg, N. et al., "Reference intervals for plasmaL-arginine and the L-arginine:asymmetric dimethylarginine ratio in the Framingham Offspring Cohort," J Nutr. Dec. 2011; 141(12): 2186-90. Epub Oct. 26, 2011.
Malumbres & Barbacid, "To Cycle or Not to Cycle: a Critical Decision in Cancer," Nat Rev Cancer. Dec. 2001; 1(3): 222-31.
Marescau et al., "Guanidino compound analysis as a complementary diagnostic parameter for hyperargininemia: follow-up of guanidino compound levels during therapy," Pediatr Res. Mar. 1990; 27(3): 297-303.
Marescau et al., "The pathobiochemistry of uremia and hyperargininemia further demonstrates a metabolic relationship between urea and guanidinosuccinic acid," Metabolism. Sep. 1992; 41(9): 1021-4.
Market Marisa et al., "Flattening the COVID-19 Curve With Natural Killer Cell Based Immunotherapies", Frontiers in Immunology, vol. 11, Jan. 1, 2020 (Jan. 1, 2020), p. 1512.
Mcgee et al., "Purification and characterization of Helicobacter pylori arginase, RocF: unique features among the arginase superfamily," Eur J Biochem. May 2004; 271(10): 1952-62.

Mercimek-Mahmutoglu et al., "A pilot study to estimate incidence of guanidinoacetate methyltransferase deficiency in newborns by direct sequencing of the GAMT gene," Gene. Jan. 1, 2016; 575(1): 127-31. Epub Aug. 28, 2015.
Mora et al., "Implications of the S-shaped domain in the quaternary structure of human arginase," Biochemica. Biophysica. Acta., 1476: 181-90, 2000.
Murch et al., "Common determinants of severe Covid-19 infection are explicable by SARS-CoV-2 secreted glycoprotein interaction with the CD33-related Siglecs, Siglec-3 and Siglec-5/14," Med Hypotheses. Nov. 2020: 144: 110168. Epub Aug. 7, 2020. 7 pages.
Newville, M., "IFEFFIT: interactive XAFS analysis and FEFF fitting," J Synchrotron Radiat. Mar. 1, 2001; 8(Pt 2): 322-4.
Ni et al., "Arginine deiminase, a potential anti-tumor drug," Cancer Lett. Mar. 8, 2008; 261(1): 1-11. Epub Jan. 7, 2008.
Non-Final Office Action for U.S. Appl. No. 15/270,955 dated Aug. 10, 2017, 12 pages.
Notice of Allowance Issued in Canadian Patent Application No. 2,742,497, dated Aug. 12, 2019. 1 page.
Oeffinger et al., "Outcome tools used for ambulatory children with cerebral palsy: responsiveness and minimum clinically important differences," Dev Med Child Neurol. Dec. 2008; 50(12): 918-25.
Office Action and Search Report for Chinese Application No. CN201880079119.9 dated May 27, 2023, with English translation, 11 pages.
Office Action for Australian Application No. AU20170310541 dated Sep. 8, 2023, 5 pages.
Office Action for Japanese Application No. JP20200531164 mailed Jul. 25, 2023, with English translation, 4 pages.
Office Action issued in Canadian Patent Application No. 2,742,497, dated Apr. 20, 2018. 3 pages.
Office Action Issued in Canadian Patent Application No. 2,742,497, dated Oct. 30, 2018. 3 pages.
Office Action issued in European Patent Application No. 16163214. 6, dated Jun. 12, 2018. 5 pages.
Office Communication issued in European Patent Application No. 09824219.1, dated Aug. 27, 2013. 5 pages.
Office Communication issued in Japanese Patent Application No. 2011-534855, dated Aug. 22, 2013. (English translation of Japanese text). 11 pages.
Office Communication issued in Japanese Patent Application No. 2011-534855, dated Jun. 5, 2014. (English translation of Japanese text). 5 pages.
Office Communication issued in U.S. Appl. No. 13/863,448, dated Feb. 24, 2014. 6 pages.
Office Communication issued in U.S. Appl. No. 13/863,448, dated Jun. 19, 2014. 24 pages.
Office Communication issued in U.S. Appl. No. 12/610,685, dated Aug. 26, 2011. 9 pages.
Office Communication issued in U.S. Appl. No. 12/610,685, dated Dec. 8, 2011. 22 pages.
Office Communication issued in U.S. Appl. No. 12/610,685, dated May 24, 2012. 14 pages.
Palacios et al., "Studies on the advent of ureotelism. The effects of bivalent cations on the capacity of the hepatic arginase of the Mexican axolotl to hydrolyse endogenous arginine," Biochem J. Sep. 1969; 114(3): 449-54.
Periyannan et al., "Sequential binding of cobalt(II) to metallo-beta-lactamase CcrA," Biochemistry. Jan. 31, 2006; 45(4): 1313-20.
Perrin, "421. The hydrolysis of manganese (II) ion," Journal of the Chemical Society, pp. 2197-2200, 1962.
Prasad et al., "Argininemia: a treatable genetic cause of progressive spastic diplegia simulating cerebral palsy: case reports and literature review," J Child Neurol. Aug. 1997; 12(5): 301-9.
Ratilla et al., "Terminal and new bridging coordination of methylguanidine, arginine, and canavanine to platinum (II). The first crystallographic study of bonding between a transition metal and a Quanidine ligand, " InorQanic Chemistry, 29: 918-926, 1990.
Reczkowski and Ash, "Rat liver arginase: kinetic mechanism, alternate substrates, and inhibitors," Arch. Biochem. Biophys., 312: 31-7, 1994.

(56) References Cited

OTHER PUBLICATIONS

Rehner et al., "Effect of manganese cobalt and nickel on the activity of liver arginase in-vitro and in-vivo," Medizin und Ernaehrung, 11 (2): 32-35, 1970. With English summary. 4 pages.
Robins and Shields, "Partial purification of bovine liver arginase," Archives of Biochemistry and Biophysics, 62: 55-62, 1956. (Abstract only). 1 page.
Rodriguez et al., "Arginine Metabolism in Myeloid Cells Shapes Innate and Adaptive Immunity," Front Immunol. Feb. 7, 2017: 8: 93. eCollection 2017. 12 pages.
Roopenian and Akilesh, "FcRn: the neonatal Fc receptor comes of age," Nat Rev Immunol. Sep. 2007; 7(9): 715-25. Epub Aug. 17, 2007.
Sabio et al., "Glu-256 is a main structural determinant for oligomerisation of human arginase I," FEBS Lett. Jul. 20, 2001; 501(2-3): 161-5.
Santhanam et al., "Inducible NO synthase dependent S-nitrosylation and activation of arginase1 contribute to age-related endothelial dysfunction," Circ Res. Sep. 28, 2007; 101(7): 692-702. Epub Aug. 17, 2007.
Sarkissian and Gamez, "Phenylalanine ammonia lyase, enzyme substitution therapy for phenylketonuria, where are we now?" Mol Genet Metab. Dec. 2005: 86 Suppl 1: S22-6. Epub Sep. 13, 2005.
Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia," Cancer Biochem Biophys. Sep. 1984; 7(3): 261-8.
Schierhorn et al., "Influenza A Virus Virulence Depends on Two Amino Acids in the N-Terminal Domain of Its NS1 Protein To Facilitate Inhibition of the RNA-Dependent Protein Kinase PKR," Journal of Virology, vol. 91, No. 10, May 15, 2017. 18 pages.
Schlune et al., "Hyperargininemia due to arginase I deficiency: the original patients and their natural history, and a review of the literature," Amino Acids. Sep. 2015; 47(9): 1751-62. Epub Jun. 27, 2015.
Schrover et al., "Minimal clinically important difference for the 6-min walk test: literature review and application to Morquio A syndrome," Orphanet J Rare Dis. Apr. 2, 20176; 12(1): 78. 11 pages.
Scolnick et al., "Altering the binuclear manganese cluster of Arginase diminishes thermostability and catalytic function," Biochemistry. Aug. 26, 1997; 36(34): 10558-65.
Scott et al., "Single amino acid (arginine) deprivation: rapid and selective death of cultured transformed and malignant cells," Br J Cancer. Sep. 2000; 83(6): 800-10.
Seely et al., "Making Site-specific Pegylation Work," BioPharm International 03-012005, vol. 18, Issue 3. Published Feb. 28, 2005. 9 printed pages.
Segawa et al., "A long-term survival case of arginase deficiency with severe multicystic white matter and compound mutations," Brain Dev. Jan. 2011; 33(1): 45-8. Epub Apr. 24, 2010.
Segel, "Enzyme Kinetics: behavior and analysis of rapid equilibrium and steady state enzyme systems," New York, John Wiley and Sons, Inc., pp. 914-917, 1975.
Shen et al., "Modulation of Arginine Metabolic Pathways As the Potential Anti-tumor Mechanism of Recombinant Arginine Deiminase," Cancer Lett., 231: 30-35, 2006.
Simmons et al., "Expression of full-length immunoglobulins in *Escherichia coli*: rapid and efficient production of aglycosylated antibodies," J Immunol Methods. May 1, 2002; 263(1-2): 133-47.
Spector et al., "Properties of fetal and adult red blood cell arginase: a possible prenatal diagnostic test for arginase deficiency," Am J Hum Genet. Jan. 1980; 32(1): 79-87.
Stemmler et al., "EXAFS comparison of the dimanganese core structures of manganese catalase, arginase, and manganese-substituted ribonucleotide reductase and hemerythrin," Biochemistry. Aug. 12, 1997; 36(32): 9847-58.
Stern et al., "Guanidinoacetate methyltransferase (GAMT) deficiency: a rare but treatable epilepsy," Pract Neurol. Jun. 2017; 17(3): 207-211. Epub Jan. 24, 2017.

Stockler-Ipsiroglu et al., "Guanidinoacetate methyltransferase (GAMT) deficiency: outcomes in 48 individuals and recommendations for diagnosis, treatment and monitoring," Mol Genet Metab. Jan. 2014; 111(1): 16-25. Epub Nov. 7, 2013.
Stone E. et al. "Strategies for Optimizing the Serum Persistence of Engineered Human Arginase I for Cancer Therapy," J Control Release. Feb. 28, 2012; 158(1): 1719. Epub Oct. 6, 2011.
Stone E M., et al., "Replacing Mn2+ with Co2+ in Human Arginase I Enhances Cytotoxicity Towards L-1arginine Auxotrophic Cancer Cell Lines," Acs Chern Bioi. Mar. 19, 2010; 5(3): 333-342.
Stone et al., "Engineering Human Arginase I As a Novel Cancer Therapeutic Agent," Retrieved from the Internet at http://aiche.conefx.com/aiche/09icbe/preliminaryprogram/abstract_143378.htm,retrieved on Feb. 29, 2012, dated Sep. 6, 2008. 1 page.
Storr & Burton, "The Effects of Arginine Deficiency on Lymphoma Cells," Br. J. Cancer, 30: 50-59, 1974.
Supplementary European Search Report and Search Opinion issued in European Application No. 09824219.1, mailed May 31, 2012. 7 pages.
Tao and Morrison, "Studies of aglycosylated chimeric mouse-human IgG. Role of carbohydrate in the structure and effector functions mediated by the human IgG constant region," J Immunol. Oct. 15, 1989; 143(8): 2595-601.
Tate et al., "Effect of arginase II on L-arginine depletion and cell growth in murine cell lines of renal cell carcinoma," J Hematol Oncol. Sep. 25, 2008: 1: 14. 10 pages.
Topal et al., "Mitochondrial Arginase II Modulates Nitric-Oxide Synthesis through Nonfreely Exchangeable L-Arginine Pools in Human Endothelial Cells," J Pharmacol Exp Ther. Sep. 2006; 318(3): 1368-74. Epub Jun. 26, 2006.
Tsui et al., "Pegylated Derivatives of Recombinant Human Arginase rhargl) for Sustained in Vivo Activity in Cancer Therapy: Preparation, Characterization and Analysis of Their Pharmacodynamics in Vivo and in Vitro and Action upon Hepatocellular Carcinoma Cell HCC)," Cancer Cell Int. Apr. 17, 2009: 9: 9. 13 pages.
Uchino, T., et al., "Molecular basis of Phenotypic Variation in patients with argininemia," Hum Genet. Sep. 1995; 96(3): 255-60.
US. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Viau, et al., "Evidence-Based Treatment of Guanidinoacetate Methyltransferase (GAMT) Deficiency," Mol Genet Metab. Nov. 2013; 110(3): 255-62. Epub Sep. 8, 2013.
Vigdorovich, V., et al., "Structure and T Cell Inhibition Properties of 87 Family Member, B7—H3," Structure, 2013, 21 (5): 707-717.
Vockley et al., "Loss of functional mutations in conserved regions of the human arginase I gene," Biochemical and Molecular Medicine, 59: 44-51, 1996.
Webb, "Sixpack: a graphical user interface for XAS analysis using IFEFFIT," Physica Scripta, 115: 1011-1014, 2005.
Wetzler et al., "Effective Asparagine Depletion with Pegylated Asparaginase Results in Improved Outcomes in Adult Acute Lymphoblastic Leukemia: Cancer and Leukemia Group B Study 9511," Blood, 109: 4164-4167, 2007.
Wheatley and Campbell, "Arginine catabolismliver extracts and cancer," Pathol. Oncol. Res., 8: 18-25, 2002.
Wheatley, "Arginine deprivation and metabolomics: important aspects of intermediary metabolism in relation to the differential sensitivity of normal and tumour cells," Semin Cancer Biol. Aug. 2005; 15(4): 247-53.
Wheatley et al., "Single Amino Acid Arginine) Restriction: Growth and Death of Cultured Hela and Human Diploid Fibroblasts," Cell Physiol Biochem. 2000; 10(1-2): 37-55.
Witalison et al., "Protein Arginine Deiminases and Associated Citrullination: Physiological Functions and Diseases Associated with Dysregulation," Curr Drug Targets. 2015; 16(7): 700-710.
Wu, G. et al., "Arginine metabolism: nitric oxide and beyond," Biochem J. Nov. 15, 1998; 336 (Pt 1) (Pt 1):1-17.
Wyse et al., "In vitro stimulation of oxidative stress in cerebral cortex of rats by the guanidino compounds accumulating in hyperargininemia," Brain Res. Dec. 27, 2001; 923(1-2): 50-7.

(56) References Cited

OTHER PUBLICATIONS

Yau et al. "A phase 1 dose-escalating study of pegylated recombinant human arginase 1 (Peg-rhArg1) in patients with advanced hepatocellular carcinoma," Invest New Drugs. Feb. 2013; 31(1): 99-107. Epub Mar. 17, 2012.
Ye et al., "Targeting Ornithine Decarboxylase by a-Difluoromethylornithine Inhibits Tumor Growth by Impairing Myeloid-Derived Suppressor Cells," Journal of Immunology, 2016, 196: 915-923; published online Dec. 9, 2015.
Yoon et al., "Renal cell carcinoma does not express argininosuccinate synthetase and is highly sensitive to arginine deprivation via arginine deiminase," Int. J. Cancer, 120: 897-905, 2006.
Yu et al., "PD-1 blockade attenuates immunosuppressive myeloid cells due to inhibition of CD47/SIRPa axis in HPV negative head and neck squamous cell carcinoma," Oncotarget, 2015, 6: 42067-42079.
Zarganes-Tzitzikas, T., et al., "Inhibitors of programmed cell death1 (PD-1): a patent review (2010-2015)," Expert Opinion on Therapeutic Patents, 2016, 26(9): 973977.
Zhang et al., "The cyanobacterial ornithine-ammonia cycle involves an arginine dihydrolase," Nat Chem Biol. Jun. 2018; 14(6): 575-581. Epub Apr. 9, 2018.
Zori, Roberto, et al., "Initial Results of a Phase 1 Open Label Study of AEB1102 Enzyme Replacement Therapy in Adult Patients with Arginase I Deficiency," Aeglea BioTherapeutics, Mar. 2017. 1 page.
Zori, R.T., "Once Weekly Intravenous Administration of Pegzilarginase Produces Marked and Sustained Reductions in Plasma Arginine Levels in Adults with Arginase 1 Deficiency: Early Results from a Phase 1/2 Open-label Study of Pegzilarginase," Molecular Genetics and Metabolism, 2018, Embase Database: Xp002788803, Database Accession No. Emb-622060654 [Abstract]. 1 page.
Agnello et al., "Abstract 869: Depletion of blood arginine with pegzilarginase (AEB1102) in combination with anti-PD-L1 increases tumor infiltration by immune cells and enhances antitumor activity." AACR, Cancer Res (2018) 78 (13_Supplement): 869. https://doi.org/10.1158/1538-7445.AM2018-869. 1 page.
Carvajal et al., "Hybrid, immobilised dimers of human liver arginase." Biochim Biophys Acta. Mar. 4, 1982; 701(3): 405-7. doi: 10.1016/0167-4838(82)90244-8.
Diaz, George, et al., "Clinical effect and safety profile of pegzilarginase in patients with arginase 1 deficiency." J Inherit Metab Dis. Jul. 2021; 44(4): 847-856. doi: 10.1002/jimd. 12343. Epub Jan. 26, 2021.
Extended European Search Report for EU Application No. 10800270.0, dated Nov. 29, 2012, 15 pages.
"Human mutant arginase I polypeptide, (Glu256Gln)." retrieved from EBI accession No. GSP:BFZ25537 Database accession No. BFZ25537, sequence & Database Geneseq [Online],Feb. 21, 2019 (Feb. 21, 2019), 2 pages.
"Human mutant arginase I polypeptide (Ser230Gly). " Retrieved from EBI accession no.GSP:BFZ25534, Database accession No. BFZ25534, sequence, Feb. 21, 2019 (Feb. 21, 2019), 2 pages.
Kanyo, Zoltan F., et al., "Structure of a unique binuclear manganese cluster in arginase", Nature (1996); 383(6600): 554-557.
Kobayashi, M., et al., "High-expression of a target gene and high-stability of the plasmid." Appl Biochem Biotechnol. Feb. 1991; 27(2): 145-62. doi: 10.1007/BF02921523.
"Mutant human arginase-1, SEQ ID 1." retrieved from EBI accession No. GSP:BGC24220 Database accession No. BGC24220, sequence, Apr. 4, 2019 (Apr. 4, 2019), 2 pages.
Office Action and Search Report for Chinese Application No. CN202080060999.2 mailed Jun. 14, 2024, 8 pages.
Savoca et al., "Preparation of a non-immunogenic arginase by the covalent attachment of polyethylene glycol." Biochim Biophys Acta. May 23, 1979; 578(1): 47-53. doi: 10.1016/0005-2795(79)90111-9.
Schulz, M F, et al., "Increased expression in Escherichia coli of a synthetic gene encoding human somatomedin C after gene duplication and fusion." J Bacteriol. Dec. 1987; 169(12): 5385-92. doi: 10.1128/jb.169.12.5385-5392.1987.
Tsumoto, Kouhei, et al., "Effects of Salts on Protein-Surface Interactions: Applications for col. Chromatography." J Pharm Sci. Jul. 2007; 96(7): 1677-90. doi: 10.1002/jps.20821.
Viator, Ryan, et al., "Characterization of Bacillus anthracis arginase: effects of pH, temperature, and cell viability on metal preference." BMC Biochem. Jun. 3, 2008: 9: 15. doi: 10.1186/1471-2091-9-15. 14 pages.
Search Report received for United Arab Emirates Application No. P6000344/2022 mailed Dec. 26, 2024, 5 pages.
Office Action for Japanese Application No. 2022-513535 issued Aug. 27, 2024, with machine translation, 11 pages.

Overview of Co-Arginase I Purification Process

| Step | Process Operation |
|---|---|
| 10 | Addition solid methoxy PEG succinimidyl carboxymethyl ester (MW 5000) and incubation pH 8.4 |
| 11 | Ultrafiltration/diafiltration 4<br><br>Buffer exchange into 20mM Sodium Phosphate, 50mM NaCl, 1.5% Glycerol, pH 7.4 and dilute to target concentration |
| 12 | Filtration of Co-ArgI-PEG drug substance, fill in 5L polycarbonate bottles, and freeze at ≤-60°C |
| 13 | Release test drug substance |

FIG. 2(b)

Analysis of Arginase 1 intermediate gluconylated variants

* Mean data not available at all time points.

METHODS FOR PRODUCTION OF HUMAN RECOMBINANT ARGINASE 1 AND USES THEREOF

CROSS-REFERENCE TO RELATED APPLICATIONS

This application is a continuation of U.S. patent application Ser. No. 17/006,383 filed on Aug. 28, 2020, which claims priority to U.S. Provisional Application No. 62/894,319 filed Aug. 30, 2019, the entire disclosure of which is hereby incorporated by reference herein.

INCORPORATION OF SEQUENCE LISTING

The Sequence Listing associated with this application is provided electronically in XML file format and is hereby incorporated by reference into the specification. The name of the XML file containing the Sequence Listing is AEGL_001_02US_SeqList_ST26.xml. The XML file is 5,702 bytes, was created on Jun. 20, 2023, and is being submitted electronically via the USPTO Patent Center.

REFERENCE TO AN ELECTRONIC SEQUENCE LISTING

The contents of the electronic sequence listing (AEGL_001_02US_SeqList_ST26.xml; Size: 5,702 bytes; and Date of Creation: Jun. 6, 2023) are herein incorporated by reference in its entirety.

TECHNICAL FIELD

The present disclosure generally relates to enzyme replacement therapy and treatment of Arginase 1 deficiency or hyperargininemia. The disclosure also encompasses methods for producing human recombinant Arginase 1. The Arginase 1 can also be used in the treatment of cancer.

BACKGROUND

Arginase 1 deficiency or hyperargininemia is a rare disorder of amino acid metabolism caused by a deficiency in the enzyme Arginase 1. Arginase 1 is one of the 6 enzymes critical to the normal function of the urea cycle; it catalyzes the conversion of L-arginine to urea and ornithine in the last step of the cycle. The ornithine then reenters the mitochondrion to continue the cycle.

Arginase 1 is found predominantly in red blood cells (RBCs) and the liver. ARG1 is the only gene in which mutations are currently known to cause Arginase 1 deficiency. Clinically, Arginase 1 deficiency is characterized by a slow deterioration of the cerebral cortex and pyramidal tracts that leads to progressive dementia, psychomotor retardation, spastic diplegia, seizures, and growth failure. If left untreated the disease progresses to severe spasticity, loss of ambulation, loss of bowel and bladder control, and severe intellectual disability. Patients with Arginase 1 deficiency typically have elevated blood arginine levels (3 to 4 times the upper limit of normal [ULN], mild hyperammonemia, and a mild increase in urinary orotic acid. Most patients have no detectable Arginase 1 enzyme activity in RBCs (<1% of normal).

The current treatment of Arginase 1 deficiency is focused on the maintenance of plasma arginine concentrations at a level as near to normal as possible through lifelong dietary protein restriction. Protein intake is limited to the minimum required to maintain protein biosynthesis and growth. Half or more of dietary protein is given in the form of an arginine free essential amino acid mixture. Such dietary modification can reduce plasma arginine levels in most patients, but the diet is unpalatable, expensive, and difficult to maintain and manage especially in growing children.

The paucity of treatment options for Arginase 1 deficient patients highlights the significant unmet need for a therapy that will lower arginine levels to within the normal range and promote the lifelong maintenance of normal arginine levels. The development of such a therapeutic could be useful in the attempt to minimize exposure to the neurotoxic effects of arginine and its metabolites and offer the potential for normal neurocognitive development in these patients.

In addition to treatment of Arginase 1 deficiency or hyperargininemia, the Arginase produced by these methods can be used to treat other diseases. Arginase 1 has been used in clinical trials investigating its use in cancer treatment and in combination with immune-oncology agents such as pembrolizumab.

SUMMARY

Production of Arginase

One aspect of the present invention relates to methods for producing and/or purifying recombinant human Arginase proteins. In one or more embodiments, the recombinant human Arginase protein is recombinant human Arginase 1 (rhARG1) (SEQ ID NO: 1; shown FIG. 1(a)). In other embodiments, the recombinant human Arginase protein is recombinant human Arginase 2 (rhARG2) (SEQ ID NO: 3; shown FIG. 1(c)). Although specific reference is made herein to rhARG1, the methods, formulations and uses described herein can also be applied to rhARG2.

Human Arginase 1 and 2 proteins that are subjected to the methods of the invention have two $Mn^{2+}$ sites; either or both sites can be substituted to generate a modified Arginase 1 or 2 protein with a non-native metal cofactor. In some embodiments, the protein displays a $k_{cat}/K_M$ greater than 200 $mM^{-1}$ $s^{-1}$ at pH 7.4. In a particular embodiment, the protein displays a $k_{cat}/K_M$ in the range of about 200 $mM^{-1}$ $s^{-1}$ to about 4,000 $mM^{-1}$ $s^{-1}$ at pH 7.4. In another embodiment, the protein displays a $k_{cat}/K_M$ in the range of about 400 $mM^{-1}$ $s^{-1}$ to about 2,500 $mM^{-1}$ $s^{-1}$ at pH 7.4 at 37° C. In a particular embodiment, the present invention contemplates a protein comprising an amino acid sequence of human Arginase 1 or 2 and a non-native metal cofactor, wherein said protein exhibits a $k_{cat}/K_M$ greater than 400 $mM^{-1}$ $s^{-1}$ at 37° C., pH 7.4. Exemplary $k_{cat}/K_M$ values include about 200, about 250, about 300, about 350, about 400, about 450, about 500, about 550, about 600, about 650, about 700, about 800, about 900, about 1,000, about 1,100, about 1,200, about 1,500, about 2,000, about 2,500, about 3,000, about 3,500 and about 4,000 $mM^{-1}$ $s^{-1}$ at pH 7.4 at 37° C.

In one or more embodiments, provided is a method for producing recombinant cobalt-substituted human Arginase protein (Co-rhARG). In one or more embodiments, the method comprises the following: strain fermentation of E. coli cells expressing rhARG1, substitution of cobalt for manganese in rhARG1 to provide a Co-Arginase 1 intermediate (Co-rhARG1), purification of this Co-Arginase 1 intermediate and PEGylation of Co-Arginase 1 intermediate to form the drug substance (Co-rhARG1-PEG). In one or more embodiments, the Co-rhARG1-PEG comprises pegzilarginase.

In one or more embodiments, the method comprises several steps: culturing E. coli cells in a bioreactor that produce the recombinant human Arginase (rhARG), lysing the E. coli cells, removing cell debris from the lysate, loading the cell lysate on a cation exchange column, eluting the recombinant human Arginase protein (rhARG) with a high salt solution, incubating the eluted recombinant human Arginase protein (rhARG) with a cobalt salt to form the cobalt-substitute recombinant human Arginase protein (Co-rhARG), applying the cobalt-substitute recombinant human Arginase protein (Co-rhARG) to an anion exchange column and collecting the flow-through, adding the flow-through onto a third chromatography column, and eluting the cobalt-substitute recombinant human Arginase protein (Co-rhARG) from the third chromatography column with a high salt concentration.

In one or more embodiments, the methods for producing recombinant cobalt-substitute human Arginase protein (Co-rhARG) comprises loading up to 60 grams of the recombinant human Arginase protein (rhARG) onto the cation exchange column per liter of cation exchange resin.

In one or more embodiments, the methods for producing recombinant cobalt-substitute human Arginase protein (Co-rhARG) comprises eluting the recombinant human Arginase protein (rhARG) from the cation exchange column using a high salt solution of up to about 0.5 M salt concentration. In some embodiments, the recombinant human Arginase protein (rhARG) is eluted from the cation exchange column using a high salt solution of 0.1 M concentration. In some embodiments, the recombinant human Arginase protein (rhARG) is eluted from the cation exchange column using a gradient of about 0.0 to about 0.5 M salt concentration. In some embodiments, the recombinant human Arginase protein (rhARG) is eluted from the cation exchange column using a gradient of about 0.0 to about 0.2 M salt concentration.

In one or more embodiments, the methods for producing recombinant cobalt-substitute human Arginase protein (Co-rhARG) comprises incubating the recombinant human Arginase protein (rhARG) that was eluted from the cation exchange column with the cobalt salt comprising $Co^{2+}$. In some embodiments, the cobalt salt comprises $CoCl_2$.

In one or more embodiments, the methods for producing recombinant cobalt-substitute human Arginase protein (Co-rhARG) comprises adding the recombinant cobalt-substitute human Arginase protein (Co-rhARG) flow-through onto the third chromatography column comprising a multimodal chromatography (MMC) column.

In one or more embodiments, the methods for producing recombinant cobalt-substitute human Arginase protein (Co-rhARG) comprises reacting the recombinant cobalt-substitute human Arginase protein (Co-rhARG) or the recombinant cobalt-substitute human Arginase protein (Co-rhARG) with a PEGylation reactant to provide a PEGylated protein. In some embodiments, the PEGylated protein comprises one or more of PEGylated amino acid residues at K16, K32, K38, K40, K47, K67, K74, K82, L87, K88, K152, K154, K171, K222, K223, K312 and K321. In some embodiments, the PEGylated protein comprises one of more of about 15% to about 60% of K16, about 35% to about 80% of K32, about 20% to about 85% of K38, about 10% to about 60% of K40, about 10% to about 60% of K47, about 40% to about 90% of K67, about 30% to about 95% of K74, about 30% to about 98% of K82, about 15% to about 65% of K87, about 25% to about 70% of K88, about 25% to about 85% of K152, about 15% to about 65% of K154, about 20% to about 75% of K171, 0% to about 30% of K222, 0% to about 35% of K223, 0% to about 45% of K312, and 0% to about 45% of K321 is PEGylated. In some embodiments, the PEGylated protein comprises PEGylated amino acid residues at least at K16, K32, K38, K40, K47, K67, K74, K82, L87, K88, K152, K154, K171, K312 and K321. In some embodiments, the PEGylated protein does not have PEGylated amino acid residues at K3, K149, K190, K195, K29, K265 and K283.

One or more embodiments of Co-rhARG1-PEG relate to a cobalt-substituted, PEGylated human recombinant Arginase 1 enzyme expressed in E. coli that is formulated for intravenous (IV) or subcutaneous (SC) administration. The replacement of the native manganese ($Mn^{2+}$) with cobalt ($Co^{2+}$) in the active site of Arginase 1 enhances the stability and catalytic activity at physiological pH. PEGylation also extends the circulating half-life ($t_{1/2}$) of recombinant Arginase 1.

In various embodiments, the methods comprise culturing E. coli cells in a bioreactor to produce recombinant human Arginase 1, lysing the E. coli cells and purifying the recombinant human Arginase 1 (See FIGS. 2 and 3(a)-3(b)). Purification of Co-Arginase 1 intermediate can be performed by a purification procedure that includes one or more of the following steps: cell disruption by high pressure homogenization, homogenate clarification, SP Sepharose FF cation exchange capture chromatography, cobalt exchange, ultrafiltration/diafiltration, Q Sepharose FF anion exchange flow-through chromatography, Capto MMC multimodal chromatography, and ultrafiltration/diafiltration. The purified Co-Arginase 1 intermediate may be processed to form PEGylated drug substance or frozen and stored for later conversion to drug substance.

In preferred embodiments of the methods, an E. coli lysate containing rhARG1 is loaded onto a cation exchange (CEX) chromatography column (also called "Column 1") to capture the rhARG1, and which is then eluted with a high salt solution to provide a first protein product ("First Protein Product").

In one or more embodiments, the method further comprises loading the First Protein Product onto an anion exchange (AEX) chromatography column (also called "Column 2") and collecting the flow-through to provide a second protein product ("Second Protein Product"). In another aspect of the methods, the method further comprises loading the Second Protein Product onto a multimodal chromatography (MMC) column which captures the Arginase 1 and is then eluted to provide a third protein product ("Third Protein Product"). In some embodiments, this third chromatography column (also called "Column 3") may be a size exclusion chromatography (SEC) column.

Various embodiments comprise changing the native manganese co-enzyme of Arginase for a cobalt co-enzyme. Cobalt substitution (also called cobalt loading) can be performed at any step in the manufacturing process. For example, Arginase 1 cobalt loading can be performed on either the E. coli lysate, the First Protein Product, the Second Protein Product, the Third Protein Product, or at any step on a PEGylated Arginase 1. In other embodiments the cobalt loading can be performed on Arginase 1 eluted from Column 1, or Arginase 1 eluted from Column 2, or Arginase 1 eluted from Column 3. Cobalt loading can be performed on an Arginase 1 that has been eluted from a CEX column, Arginase 1 eluted from an AEX column, Arginase 1 eluted from an MMC column, or Arginase 1 eluted from an SEC column.

Cobalt loading of Arginase 1 can be done with a variety of solutions containing cobalt and at a variety of temperatures. In one or more embodiments, the cobalt salt comprises a Co²⁺ such CoCl$_2$. In a preferred embodiment, cobalt loading of Arginase 1 is performed with CoCl$_2$ at or about room temperature, such as about 15 to about 25° C. or about 20 to about 25° C. The rate of cobalt loading can be manipulated by increasing or decreasing the temperature of the reaction. Cobalt loading can also be performed at a range of pH values.

One aspect of the present disclosure pertains to varying the conditions related to CEX chromatography (Column 1). The amount of protein loaded onto Column 1 can be increased or decreased to select for different Arginase 1 charge variants. Load factors can be manipulated to cause a shift towards more desirable CEX charge species profiles. Load factors (amount of protein in grams/volume of CEX column resin in liters) up to about 60 g/L can produce Arginase 1 with high specific activity. In various embodiments, the load factor is up to about 10 g/L, about 20 g/L, about 30 g/L, about 40 g/L, about 50 g/L or about 60 g/L.

In a preferred embodiment, Arginase 1 is first captured on Column 1 followed by sequential purification on Column 2, then Column 3. In an alternative embodiment, the *E. coli* lysate can be loaded onto an AEX column (for example Column 2) and the flow through applied to a CEX column to capture the Arginase 1. In another embodiment, cobalt loading of Arginase 1 can occur after the PEGylation reaction. Also, other chromatography columns can be used to replace the MMC column, such as an SEC column.

One aspect of the present invention relates to methods for producing recombinant cobalt-substitute human Arginase protein (Co-rhARG). In one or more embodiments, the recombinant human Arginase protein (rhARG) comprises an amino acid sequence that is at least 98% identical to SEQ ID NO: 1. The method comprises several steps: culturing *E. coli* cells in a bioreactor that produce the recombinant human Arginase (rhARG), lysing the *E. coli* cells, removing cell debris from the lysate, loading the cell lysate on a cation exchange column, eluting the recombinant human Arginase protein (rhARG) with a high salt solution, incubating the eluted recombinant human Arginase protein (rhARG) with a cobalt salt to form the cobalt-substitute recombinant human Arginase protein (Co-rhARG), applying the cobalt-substitute recombinant human Arginase protein (Co-rhARG) to an anion exchange column and collecting the flow-through, adding the flow-through onto a third chromatography column, eluting the cobalt-substitute recombinant human Arginase protein (Co-rhARG) from the MMC column with a high salt solution, reacting a molar excess of methoxy PEG succinimidyl carboxymethyl ester and removing excess PEG.

Recombinant Human Arginase 1, Pharmaceutical Compositions and Formulations

Another aspect of the present invention relates to rhARG1, Co-rhARG1 and/or Co-rhARG1-PEG produced by the methods described herein, or a composition comprising the same.

In one or more embodiments, the protein is covalently linked to a polyethylene glycol at one or more of K16, K32, K38, K40, K47, K67, K74, K82, L87, K88, K152, K154, K171, K222, K223, K312 and K321.

Another aspect of the present invention relates to a composition comprising a recombinant human Arginase (rhARG) protein, wherein the protein comprises an amino acid sequence that is at least 98% identical to SEQ ID NO: 1, wherein the protein is in a complex with a non-native metal cofactor, wherein the non-native metal cofactor is cobalt, and wherein the protein is covalently linked to a polyethylene glycol at one or more of K16, K32, K38, K40, K47, K67, K74, K82, L87, K88, K152, K154, K171, K222, K223, K312 and K321.

In one or more embodiments, the protein comprises an amino acid substitution at a position selected from the group consisting of: H100, D123, H125, D127, D231, D233, W121, D180, S229, C302, and E255.

In one or more embodiments, the protein comprises at least one amino acid substitution selected from the group consisting of: D180S, S229C, S229G, C302F, C302I, E255Q, D180E, and S229A.

In one or more embodiments, the at least one amino acid substitution is C302.

In one or more embodiments, the protein comprises at least two amino acid substitutions.

In one or more embodiments, the protein is a truncated arginase I protein.

In one or more embodiments, the protein further comprises an exogenous protein fragment.

In one or more embodiments, the exogenous protein fragment comprising the Fc region of an immunoglobulin or a portion of the Fc region of an immunoglobulin.

In one or more embodiments, the specific activity of Co-rhARG-PEG is in the range of about 400 U/mg to about 700 U/mg.

In one or more embodiments, the protein displays a $k_{cat}/K_m$ for the hydrolysis of arginine in the range of about 200 mM$^{-1}$ s$^{-1}$ to about 4,000 mM$^{-1}$ s$^{-1}$ at pH 7.4 when assayed in vitro.

In one or more embodiments, the protein displays a $k_{cat}/K_M$ for the hydrolysis of arginine in the range of about 400 mM$^{-1}$ s$^{-1}$ to about 2,500 mM$^{-1}$ s$^{-1}$ at pH 7.4 when assayed in vitro.

In one or more embodiments, the molar ratio of PEG:Co-rhARG is in the range of about 7 moles/mole to about 15 moles/mole.

In one or more embodiments, the free PEG concentration is less than or equal to 100 μg/mL.

In one or more embodiments, the total cobalt content of the composition is in the range of about 9 μg/mL to about 15 μg/mL.

In one or more embodiments, the composition produces at least 9 peaks when loaded on imaging capillary isoelectric focusing (iCIEF), wherein peak 1 is less than 20%, peak 2 is less than 30%, Peak 3+4 is in the range of 10-30%, peak 5 is in the range of 15-30%, peak 6 is in the range of 10-25%, peak 7 is less than 25%, peak 8 is less than 15%, and peak 9 is less than 8%.

In one or more embodiments, the composition produces at least 9 peaks when loaded on icIEF, wherein peak 1 is in the range of 5-7%, peak 2 is in the range of 8-11%, Peak 3+4 in the range of 16-20%, peak 5 in the range of 21-24%, peak 6 in the range of 21-22%, peak 7 in the range of 14-15%, peak 8 in the range of 5-8%, and peak 9 in the range of 2-3%.

Another aspect of the present invention relates to pharmaceutical compositions comprising the rhARG1, Co-rhARG1 and/or Co-rhARG1-PEG, and a pharmaceutically acceptable carrier. In one or more embodiments, the composition is formulated for intravenous or subcutaneous administration. In one or more embodiments, the composition comprises potassium phosphate, sodium chloride and glycerol. In one or more embodiments, the composition comprises about 50 mM NaCl, about 1 mM K$_2$HPO$_4$, about 4 mM KH$_2$PO$_4$, and about 1.5% w/v glycerol.

Method of Treating Arginase 1 Deficiency

Another aspect of the present invention relates to the administration of a recombinant human Arginase 1 such as Co-rhARG1-PEG. Such administration can be by any suitable method, including IV or SC administration. In one or more embodiments of this aspect, the dose of Co-rhARG1-PEG is determined by a particular algorithm:

In one or more embodiments of this algorithm, the patient initiates therapy at 0.10 mg/kg. Plasma arginine levels are monitored. If the plasma arginine level is >150 µM, the dose will be increased to 0.20 mg/kg. If the plasma arginine level is <50 µM, the dose is decreased to 0.05 mg/kg. Otherwise, the patient remains on the dose at 0.10 mg/kg.

In one or more embodiments of this algorithm, dose modifications are as follows:

If the plasma arginine level is >150 µM, a single 168-hour sample will be used to increase the dose by 2 dose levels in the table below (not to exceed 0.20 mg/kg) if the 2 doses prior to this sample were a) the same dose level in mg/kg, and b) consecutive (with no missed doses).

If the plasma arginine levels from 2 sequential 168-hour samples (regardless of missed doses) are both <50 µM, the dose is decreased by 1 dose level in the table below, not to decrease below 0.05 mg/kg.

| Dose Level[a] | Dose |
| --- | --- |
| 1 (Minimum Possible Dose) | 0.05 mg/kg |
| 2 (Starting Dose) | 0.10 mg/kg |
| 3 | 0.15 mg/kg |
| 4 (Maximum Possible Dose) | 0.20 mg/kg |

[a] Pegzilarginase dosing starts at level 2. 0.10 mg/kg. Dose increases when required, are by 2 dose levels. Dose decreases are by 1 dose level.

BRIEF DESCRIPTION OF THE DRAWINGS

Further features of the present invention will become apparent from the following written description and the accompanying figures, in which:

FIG. 1(a) shows the amino acid sequence of recombinant human Arginase 1 that was expressed in E. coli. (SEQ ID NO: 1); and FIG. 1(b) shows the codon optimized DNA sequence (SEQ ID NO: 2) of recombinant human Arginase 1. The expressed monomer of Arginase 1 is missing the N-terminal methionine found in native human Arginase 1 monomer. FIG. 1(c) shows the amino acid sequence of Arginase 2 that is missing the N-terminal methionine found in native human Arginase 2 monomer.

FIG. 3(a) shows an exemplary process including a cation exchange column (Column 1), an anion exchange column (Column 2) and a Capto multimodal column (Column 3), as well as a cobalt loading step. FIG. 3(b) shows PEGylation of the Co-Arginase 1 intermediate, followed by final filtering and formulation to provide the drug substance.

FIG. 4(a) shows loading the E. coli cell lysate onto a cation exchange column (Column 1), washing of the column, then elution with a high salt solution (to provide a First Protein Product). Protein loading and elution was assessed by measuring UV absorbance at 280 nm. Approximately 3 liters (L) of cell lysate was applied to the column, then the column washed with approx. 1.5 L of buffer, then elution was performed with less than about 1 L. FIG. 4(b) shows loading of the Column 1 eluted Arginase 1 (the First Protein Product) onto an anion exchange column (Column 2), the protein concentration was measured using absorbance at 280 nm. Arginase 1 was collected in the flow through from this Column 2 to provide a Second Protein Product. FIG. 4(c) shows capture of Arginase 1 onto the Capto Multimodal Cation Exchange column (Column 3) and elution with a high salt solution to provide a Third Protein Product.

FIG. 5(a) shows a representative chromatogram of the charge heterogeneity species of Arginase 1. The Arginase 1 charge variants were eluted from this analytical HPLC column after 10-20 minutes. FIG. 5(b) shows the same chromatogram as FIG. 5(a) with greater magnification of the peaks. FIG. 5(c) shows the assignment of Peak Numbers to the Arginase 1 cation exchange charge variants. FIG. 5(d) shows a typical charge heterogeneity profile of drug substance resolved by an imaging capillary isoelectric focusing (iCIEF) method.

FIG. 8(a) shows a representative enzyme kinetic analysis of Co-Arginase 1 intermediate (conversion of arginine to ornithine with substrate concentrations over a range of 0-2 mM at 37° C.). FIG. 8(b) shows a representative enzyme kinetic analysis for Co-rhARG1-PEG drug substance.

FIGS. 9(a)-9(f) show a pharmacokinetic analysis of Co-rhARG1-PEG drug substance. FIGS. 9(a) and 9(b) show mean (±SD) Arginase 1 concentration versus time profiles in patients following a single IV dose administration of Co-rhARG1-PEG: Part 1. Linear (FIG. 9(a)) and semi-log (FIG. 9(b)) plots are shown. Note that first mean BQL concentration is plotted at half of the LLOQ (0.125 µg/mL). Mean circulating drug concentrations in all patients increased with escalating doses of Co-rhARG1-PEG. FIGS. 9(c)-9(f) show mean (±SD) Co-rhARG1-PEG concentration versus time profiles in patients following QW (weekly) IV dose administration of Co-rhARG1-PEG: Part 2. Linear plots for week 1 (FIG. 9(c)) and week 8 (FIG. 9(d)); semi-log plots for week 1 (FIG. 9(e)) and week 8 (FIG. 9(f)).

FIGS. 10(a)-10(c) show three representative integrated plots for pharmacokinetics (PK) and pharmacodynamics (PD) in the Phase 1/2, open-label study to evaluate administration of Co-rhARG1-PEG to patients with Arginase 1 deficiency: Patient 1 (FIG. 10(a)); Patient 2 (FIG. 10(b)), and; Patient 3 (FIG. 10(c)). Using the escalation stop criteria, the doses settled upon in Part 2 were 0.09 mg/kg for Patient 1, 0.12 mg/kg for Patient 3, and 0.04 mg/kg (for the period of Part 2 shown). By applying the dose escalation stopping criteria, other patients in the trial settled upon a variety of Part 2 dosing levels. These same criteria can be applied to adjust (increase or decrease) the dose of any patient that is already on Co-rhARG1-PEG in response to arginine levels that move outside preferred (healthy) ranges.

FIG. 11(a) includes data from the first week subsequent to end of Part 2 and FIG. 11(b) excludes IV data from this week 1 extension. Plots are shown as an average of patient values and the data are drawn from the dose that the stopping criteria determined for each patient.

FIG. 12(a) shows plasma arginine levels at baseline, after dose 1, after dose 8 and during the open label extension (OLE). FIG. 12(b) shows plasma levels for guanidinoacetic acid (GAA), N-α-acetyl-L-arginine (NAA), α-keto-δ-guanidinovaleric acid (GVA) and argininic acid (ARGA) at baseline and during the OLE.

FIG. 13(a) shows the baseline deficit for Arginase 1 deficiency patients for the 6-Minute Walk Test (6MWT), Gross Motor Function Measure (GMFM) Parts D and E, and Adaptive Behaviour Assessment System (AB AS). FIG. 13(b) shows the clinical response for the 6MWT, GMFM-D and GMFM-E.

FIG. 14(a) shows the percentage of clinical responders for 6MWT across all patients and those with baseline deficits in 6MWT at dose 8 and dose 20. FIG. 14(b) shows the percentage of clinical responders for GMFM-D across all patients and those with baseline deficits in 6MWT at dose 8 and dose 20. FIG. 14(c) shows the percentage of clinical responders for GMFM-E across all patients and those with baseline deficits in 6MWT at dose 8 and dose 20.

FIG. 17 shows an exemplary Phase 3 trial schedule.

DETAILED DESCRIPTION

Recombinant Human Arginase 1

Human Arginase 1, identified as hArg 1, is a binuclear manganese metalloenzyme that catalyzes the hydrolysis of L-arginine (L-Arg) to yield L-ornithine and urea. Arginase 1 is a trimer of three non-covalently bound identical monomer units. Monomeric Arginase 1 is enzymatically active but less stable. The substitution of the native manganese ($Mn^{2+}$) with cobalt ($Co^{2+}$) in the active site of Arginase 1 enhances catalytic activity at physiological pH. The methods of producing cobalt-substituted Arginase 1 enzyme described herein provide an enzyme that is highly pure and highly active. The methods can also provide Co-Arginase 1 (Co-rhARG1) as an isolated intermediate in the manufacture of the drug substance. In one or more embodiments, the drug substance is PEGylated Co-Arginase 1 (Co-rhARG1-PEG). PEGylation of Co-Arginase 1 extends the circulating half-life significantly. Again, although specific reference is made herein to rhARG1, the methods, formulations and uses described herein can also be applied to rhARG2.

As used herein, the term "rhARG1" refers to a recombinant human Arginase 1 enzyme, such as a recombinant enzyme having at least 98% sequence identity to SEQ ID NO: 1.

As used herein, the terms "Co-rhARG1", "Co-Arginase 1 intermediate" and the like refer to a rhARG1 that has at least some of the native manganese cofactor replaced with cobalt. In one or more embodiments, the Co-rhARG1 is an isolatable intermediate in a production and/or purification process for Co-rhARG1-PEG.

As used herein, the terms "Co-rhARG1-PEG", "PEGylated Co-Arginase 1" and the like refers to a Co-rhARG1 that has one or more PEG units covalently linked to the enzyme, such as at free amine(s) at the N-terminal amino acid and/or at one or more lysine residues.

The quantity of Co-rhARG1-PEG drug substance can be expressed as the mass amount of un-PEGylated enzyme. In one embodiment of the method, each mg (enzyme basis) of Co-rhARG1-PEG drug substance also contains approximately 1-2 mg of PEG, such as about 1.4 mg of PEG.

Figure 1:
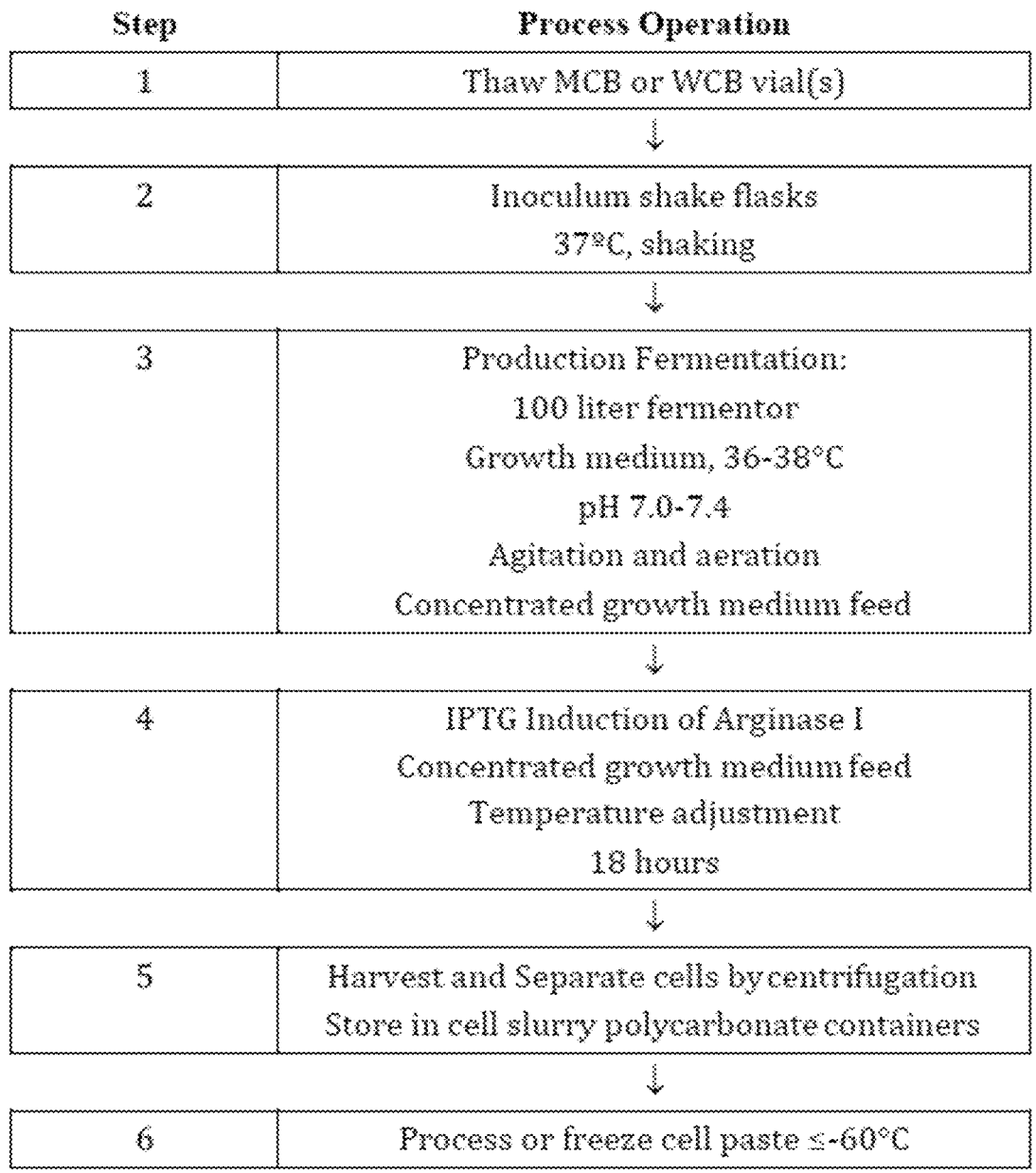
FIGS. 1(a)-1(c) show the amino acid and DNA sequence of Arginase 1, as well as the amino acid sequence of Arginase 2.

FIG. 1(a) shows the amino acid sequence that was expressed in *E. coli*. The hArg 1 protein sequence was obtained from the NCBI database (UniProtKB: locus ARGI1_HUMAN, accession P05089). Overlapping oligonucleotides were used in a PCR reaction to generate Arginase 1 DNA that was codon optimized for expression in *E. coli* (FIG. 1(b)). The 321 amino acid *E. coli* expressed monomer of Arginase 1 lacks the N-terminal methionine found in native human Arginase 1 monomer. The calculated molecular weight of Co-Arginase 1 is 34721.6 Daltons (Table 1). The calculated molecular weight of homotrimeric Co-Arginase 1 is 104164.8 Daltons. Arginase 1 does not have any disulfide bonds.

TABLE 1

Structural Information of an Exemplary Co-Arginase 1 Intermediate

| | |
|---|---|
| Molecular weight of Co-Arginase 1 | 34721.6 Daltons (calculated value with cobalt) |
| Homotrimeric Co-Arginase 1 | 104164.8 Daltons (calculated value with cobalt) |
| Length of the monomer | 321 amino acid residues |
| Disulfide bonds | None |
| Amino acid sequence | The primary sequence of recombinant human Arginase 1 is provided in FIG. 1(a)-1(c) |

In one or more embodiments, the calculated molecular weight of monomeric Co-rhARG1-PEG is about 75-115 kDa. In one or more embodiments, the calculated molecular weight of homotrimeric Co-rhARG1-PEG is about 224-344 kDa. In one or more embodiments, the average number of PEG is about 8 to about 25 moles of PEG/mole Co-Arginase 1 monomer, such as about 8 to about 16 moles of PEG/mole Co-Arginase 1 monomer. Exemplary amounts of PEG include about 8, about 9, about 10, about 11, about 12, about 13, about 14, about 15 and about 16 moles of PEG/mole Co-Arginase 1 monomer. In one or more embodiments, each PEG has an average molecular weight of about 1,000 to about 10,000 Daltons, such as about 1,000, about 2,000, about 3,000, about 4,000, about 5,000, about 6,000, about 7,000, about 8,000, about 9,000 or about 10,000 Daltons. In a particular embodiment, the average MW of the PEG is about 5,000 Daltons.

In one or more embodiments, the Co-rhARG1-PEG comprises pegzilarginase. Pegzilarginase has the following two chemical names:
  a. poly(oxy-1,2-ethanediyl), α-(carboxymethyl)-ω-methoxy-, amide with arginase 1 [cobalt cofactor] (synthetic human) (1:10), trimer
  b. Des-Met[1]-arginase-1 (liver-type arginase, EC 3.5.3.1) (Homo sapiens) from which manganese has been replaced with cobalt, an average of 10 primary amines (of N-terminal serines and $N^6$-lysines) are amidified with [methoxypoly(ethyleneoxy)]acetyl, non-covalent homotrimer, produced in *Escherichia coli* The molecular formula for pegzilarginase is $C_{1554}H_{2492}N_{416}O_{453}S_6$ $[C_3H_4O_2 (C_2H_4O_n)_n]_a$ monomer. The average molecular weight for pegzilarginase is 284 kDa for the trimer. The CAS registry number for pegzilarginase is 1659310-95-8.

Potential PEGylation sites of pegzilarginase are shown below in SEQ ID NO: 1:

```
Monomer sequence
SAKSRTIGII GAGFSKGQPR GGVEEGPTVL RKAGLLEKLK EQECDVKDYG      50

DLPFADIPND SPPQIVKNPR SVGKASEQLA GKVAEVKKNG RISLVLGGDH     100

SLAIGSISGH ARVHPDLVGI WVDAHTDINT PLTTTSGNLH GQPVSFLLKE     150

LKGKIPDVPG FSWVTPCSIA KDIVYIGLRD VDPGEHYILK TLGIKYFSMT     200

EVDRLGIGKV MEETLSYLLG RKKRPIHLSF DVDGLDPSFT PATGTPVVGG     250

LTYREGLYIT EEIYKTGLLS GLDIMEVNPS LGKTPEEVTR TVNTAVAITL     360

ACFGLAREGN HKPIDYLNPP K                                    321
```

Potential Modified Residues

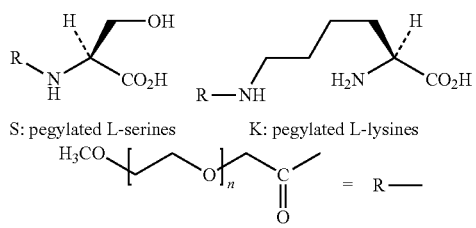

S: pegylated L-serines     K: pegylated L-lysines

Typically, PEGylation reaction is performed on the Co-rhARG1. In some embodiments, PEGylation reaction may be performed on the rhARG1. In one or more embodiments, amount of reactants, time, temperature and solution and reactant handling (such as mixing, addition rate, PEG handling) are important to produce consistent PEGylated product. Typically, PEGylation reaction on Co-rhARG1 is performed in a reaction buffer at pH 8.4. In one or more embodiments, the Co-rhARG1 is PEGylated in 0.1M sodium phosphate buffer at pH 8.4. In one or more embodiments, the PEGylation reaction comprises reactant ratio, PEG (g) to Co-rhARG1 (g), is in the range of 4:1 to 1:1. In one or more embodiments, the PEGylation reaction comprises reactant ratio, PEG (g) to Co-rhARG1 (g), is about 2.77:1. In one or more embodiments, the PEGylation reaction is performed by misting PEG and Co-rhARG1 from about 5 minutes to about 300 minutes, about 10 minutes to about 300 minutes, about 20 minutes to about 300 minutes, about 30 minutes to about 300 minutes, about 5 minutes to about 280 minutes, about 10 minutes to about 280 minutes, about 20 minutes to about 280 minutes, about 30 minutes to about 280 minutes, about 5 minutes to about 260 minutes, about 10 minutes to about 260 minutes, about 20 minutes to about 260 minutes, about 30 minutes to about 260 minutes, about 5 minutes to about 240 minutes, about 10 minutes to about 240 minutes, about 20 minutes to about 240 minutes, about 30 minutes to about 240 minutes. In one or more embodiments, the PEGylation reaction is stopped by removing excess PEG and reducing pH of the reaction buffer. In some embodiments, the excess PEG is removed by filtration technique. In one or more embodiments, the pH is reduced by exchanging the reaction buffer with a storage buffer. In some embodiments, the storage buffer comprises 5 mM potassium phosphate, 50 mM NaCl, 1.5% w/v Glycerol and pH 7.4.

In one or more embodiments, the Co-rhARG1-PEG is PEGylated at one or more of K16, K32, K38, K40, K47, K67, K74, K82, L87, K88, K152, K154, K171, K222, K223, K312 and K321 amino acid residues. In some embodiments, the Co-rhARG1-PEG is PEGylated at least at K16, K32, K38, K40, K47, K67, K74, K82, L87, K88, K152, K154, K171, K312 and K321 amino acid residues. In some embodiments, the Co-rhARG1-PEG is PEGylated at K222 and/or K223 amino acid residues. In some embodiments, the Co-rhARG1-PEG is not PEGylated at K222 and/or K223 amino acid residues. In some embodiments, the Co-rhARG1-PEG is not PEGylated at one or more of K3, K149, K190, K195, K29, K265 and K283 amino acid residues. In some embodiments, the Co-rhARG1-PEG is not PEGylated at K3, K149, K190, K195, K29, K265 and K283 amino acid residues.

In one or more embodiments of the Co-rhARG1-PEG, K16 is PEGylated in the range of about 15% to about 60%. In one or more embodiments of the Co-rhARG1-PEG, K32 is PEGylated in the range of about 35% to about 80%. In one or more embodiments of the Co-rhARG1-PEG, K38 is PEGylated in the range of about 20% to about 85%. In one or more embodiments of the Co-rhARG1-PEG, K40 is PEGylated in the range of about 10% to about 60%. In one or more embodiments of the Co-rhARG1-PEG, K47 is PEGylated in the range of about 10% to about 60%. In one or more embodiments of the Co-rhARG1-PEG, K67 is PEGylated in the range of about 40% to about 90%. In one or more embodiments of the Co-rhARG1-PEG, K74 is PEGylated in the range of about 30% to about 95%. In one or more embodiments of the Co-rhARG1-PEG, K82 is PEGylated in the range of about 30% to about 98%. In one or more embodiments of the Co-rhARG1-PEG, K87 is PEGylated in the range of about 15% to about 65%. In one or more embodiments of the Co-rhARG1-PEG, K88 is PEGylated in the range of about 25% to about 70%. In one or more embodiments of the Co-rhARG1-PEG, K152 is PEGylated in the range of about 25% to about 85%. In one or more embodiments of the Co-rhARG1-PEG, K154 is PEGylated in the range of about 15% to about 65%. In one or more embodiments of the Co-rhARG1-PEG, K171 is PEGylated in the range of about 20% to about 75%. In one or more embodiments of the Co-rhARG1-PEG, K222 is PEGylated in the range of 0% to about 30%. In one or more embodiments of the Co-rhARG1-PEG, K223 is PEGylated in the range of 0% to about 35%. In one or more embodiments of the Co-rhARG1-PEG, K312 is PEGylated in the range of 0% to about 45%. In one or more embodiments of the Co-rhARG1-PEG, K321 is PEGylated in the range of 0% to about 45%.

PEG-Protein Molar ratio is an attribute indicative of the extent of PEGylation. In one or more embodiments, about 1 to about 20 moles of PEG has PEGaylated one mole of Co-rhARG1. Exemplary range of molar ratio for PEG:Co-rhARG1 include 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 and 20:1. In some embodiments, the molar ratio of PEG:Co-rhARG is in the range of about 7 moles/mole to about 15 moles/mole.

The free PEG is measured to demonstrate PEG clearance and stability. In some embodiments, free PEG concentration (µg) in PEGylated Co-rhARG1 (mL) is less than or equal to 500 µg/mL, less than or equal to 400 µg/mL, less than or equal to 300 µg/mL, less than or equal to 200 µg/mL, less than or equal to 100 µg/mL, and less than or equal to 50 µg/mL.

Human Arginase 1 catalyzes the fifth and final step in the urea cycle which is the conversion of L-arginine into L-ornithine and urea. The PEGylated drug substance, Co-rhARG1-PEG, catalyzes the same reaction. The assay to assess enzyme activity measures the conversion of L-arginine to L-ornithine during a fixed reaction time at pH 7.4 and 37° C. The amount of conversion of product is converted to a reaction rate and fit to the Michaelis-Menten equation to determine $K_m$ and $k_{cat}$.

$$V = \frac{Vmax[S]}{Km + [S]}$$

$V_{max}$ is the maximum reaction rate achieved at saturating substrate concentration; $K_m$ is the Michaelis-Menten binding constant to measure the substrate concentration yielding a velocity at the half of $V_{max}$. The enzymatic turnover number, $k_{cat}$ is calculated by $V_{max}/[E]$.

Specific activity is determined by dividing the reaction velocity at 2 mM arginine expressed in µmoles/minute by the enzyme concentration in mg.

The values for Co-rhARG1-PEG drug substance for $K_M$ and $k_{cat}$ as measured in the enzyme activity assay typically range from 0.15-0.22 mM and approximately 200-300/sec respectively. Upon PEGylation of the Co-Arginase 1 intermediate to form the drug substance, compared to the unPEGylated intermediate, the enzyme activity is not significantly changed. However, PEGylation significantly increases the circulating half-life of the Co-rhARG1-PEG drug product compared to the Co-Arginase 1 intermediate.

In one or more embodiments, the protein (e.g. Co-rhARG1 or Co-rhARG1-PEG) displays a $k_{cat}/K_M$ greater than 200 mM$^{-1}$ s$^{-1}$ at pH 7.4. In a particular embodiment, the protein displays a $k_{cat}/K_M$ in the range of about 200 mM$^{-1}$ s$^{-1}$ to about 4,000 mM$^{-1}$ s$^{-1}$ at pH 7.4. In another embodiment, the protein displays a $k_{cat}/K_M$ in the range of about 400 mM$^{-1}$ s$^{-1}$ to about 2,500 mM$^{-1}$ s$^{-1}$ at pH 7.4 at 37° C. In a particular embodiment, the present invention contemplates a protein comprising an amino acid sequence of human Arginase 1 and a non-native metal cofactor, wherein said protein exhibits a $k_{cat}/K_M$ greater than 400 mM$^{-1}$ s$^{-1}$ at 37° C., pH 7.4. Exemplary $k_{cat}/K_M$ values include about 200, about 250, about 300, about 350, about 400, about 450, about 500, about 550, about 600, about 650, about 700, about 800, about 900, about 1,000, about 1,100, about 1,200, about 1,500, about 2,000, about 2,500, about 3,000, about 3,500 and about 4,000 mM$^{-1}$ s$^{-1}$ at pH 7.4 at 37° C., or any range in between these values.

The specific activity is an indication of potency of the protein (e.g. Co-rhARG1 or Co-rhARG1-PEG). In one or more embodiments, the specific activity of Co-rhARG-PEG is in the range of about 200 U/mg to about 1000 U/mg. Exemplary ranges of the specific activity include about 200 U/mg to about 1000 U/mg, about 300 U/mg to about 1000 U/mg, about 400 U/mg to about 1000 U/mg, about 200 U/mg to about 900 U/mg, about 300 U/mg to about 900 U/mg, about 400 U/mg to about 900 U/mg, about 200 U/mg to about 800 U/mg, about 300 U/mg to about 800 U/mg, about 400 U/mg to about 800 U/mg, about 200 U/mg to about 700 U/mg, about 300 U/mg to about 700 U/mg, and about 400 U/mg to about 700 U/mg.

In one or more embodiments, the rhARG1, Co-rhARG1 or Co-rhARG1-PEG can have at least 98%, 98.5%, 99% or 99.5% identity to SEQ ID NO: 1. In one or more embodiments, rhARG1, Co-rhARG1 or Co-rhARG1-PEG can have at 1, 2, 3, 4, 5, 6, 7, 8, 9, 10, 11, 12, 13, 14, 15 or more deletions, substitutions and/or insertions to the amino acid sequence described by SEQ ID NO: 1. Various alignment algorithms and/or programs may be used to calculate the identity between two sequences, including FASTA, or BLAST which are available at the National Center for Biotechnology Information website (http://www.ncbi.nlm.nih.gov/).

In one or more embodiments, the rhARG1, Co-rhARG1 or Co-rhARG1-PEG has at least one amino acid substitution at a position selected from H100, D123, H125, D127, D231, D233, D180, 5229, and C302. In some embodiments, rhARG1, Co-rhARG1 or Co-rhARG1-PEG comprises at least one amino acid substitution selected from the group consisting of: D180S, S229C, S229G, C302F, C302I, E255Q, D180E, and S229A. In one or more embodiments, rhARG1, Co-rhARG1 or Co-rhARG1-PEG comprises at least an amino acid substitution at C302.

Using the methods described herein, it is possible to replace almost all the manganese cofactor in Arginase 1 with cobalt. The change to cobalt cofactor results in a change in the $K_m$ for arginine from 2.8 mM to about 0.18 mM at pH 7.4. In one or more embodiments, the Co-rhARG1-PEG comprises about 0.1 to about 2 µg Co/mg protein. Exemplary cobalt loadings include about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9 and about 2 µg Co/mg protein.

The free cobalt is measured to demonstrate cobalt clearance and stability. In some embodiments, the free cobalt is less than or equal to 0.10 µg/mL, less than or equal to 0.09 µg/mL, less than or equal to 0.08 µg/mL, less than or equal to 0.07 µg/mL, less than or equal to 0.06 µg/mL, less than or equal to 0.05 µg/mL, and less than or equal to 0.04 µg/mL.

The total cobalt impacts potency of the protein and is an indicator of bound cobalt as the amount of free cobalt is relatively small. In some embodiments, the total cobalt concentration is in the range of about 5 µg/mL to about 20 µg/mL, about 6 µg/mL to about 20 µg/mL, about 7 µg/mL to about 20 µg/mL, about 8 µg/mL to about 20 µg/mL, about 9 µg/mL to about 20 µg/mL, about 5 µg/mL to about 19 µg/mL, about 6 µg/mL to about 19 µg/mL, about 7 µg/mL to about 19 µg/mL, about 8 µg/mL to about 19 µg/mL, about 9 µg/mL to about 19 µg/mL, about 5 µg/mL to about 18 µg/mL, about 6 µg/mL to about 18 µg/mL, about 7 µg/mL to about 18 µg/mL, about 8 µg/mL to about 18 µg/mL, about 9 µg/mL to about 18 µg/mL, about 5 µg/mL to about 17 µg/mL, about 6 µg/mL to about 17 µg/mL, about 7 µg/mL to about 17 µg/mL, about 8 µg/mL to about 17 µg/mL, about 9 µg/mL to about 17 µg/mL, about 5 µg/mL to about 16 µg/mL, about 6 µg/mL to about 16 µg/mL, about 7 µg/mL to about 16 µg/mL, about 8 µg/mL to about 16 µg/mL, about 9 µg/mL to about 16 µg/mL, about 5 µg/mL to about 15 µg/mL, about 6 µg/mL to about 15 µg/mL, about 7 µg/mL to about 15 µg/mL, about 8 µg/mL to about 15 µg/mL, and about 9 µg/mL to about 15 µg/mL.

In various embodiments, the Co-rhARG1-PEG comprises less than about 1 µg Mn/mg protein, such as less than about 1, about 0.9, about 0.8, about 0.7, about 0.6, about 0.5, about 0.4, about 0.3, about 0.2, about 0.15, about 0.1, about 0.09, about 0.08, about 0.07, about 0.06, about 0.05, about 0.04, about 0.03, about 0.02 or about 0.01 µg Mn/mg protein. In a particular embodiment, Co-rhARG1-PEG drug substance contains about 2 µg Co/mg protein and about 0.05 µg Mn/mg protein.

In various embodiments, the Co-rhARG1-PEG comprises less than about 1 µg Fe/mg protein, such as less than about 1, about 0.9, about 0.8, about 0.7, about 0.6, about 0.5, about 0.4, about 0.3, about 0.2, about 0.15, about 0.1, about 0.09, about 0.08, about 0.07, about 0.06, about 0.05, about 0.04, about 0.03, about 0.02 or about 0.01 µg Fe/mg protein.

Production and Purification of rhARG1, Co-rhARG1 and PEGrhARG1

Figure 2A:
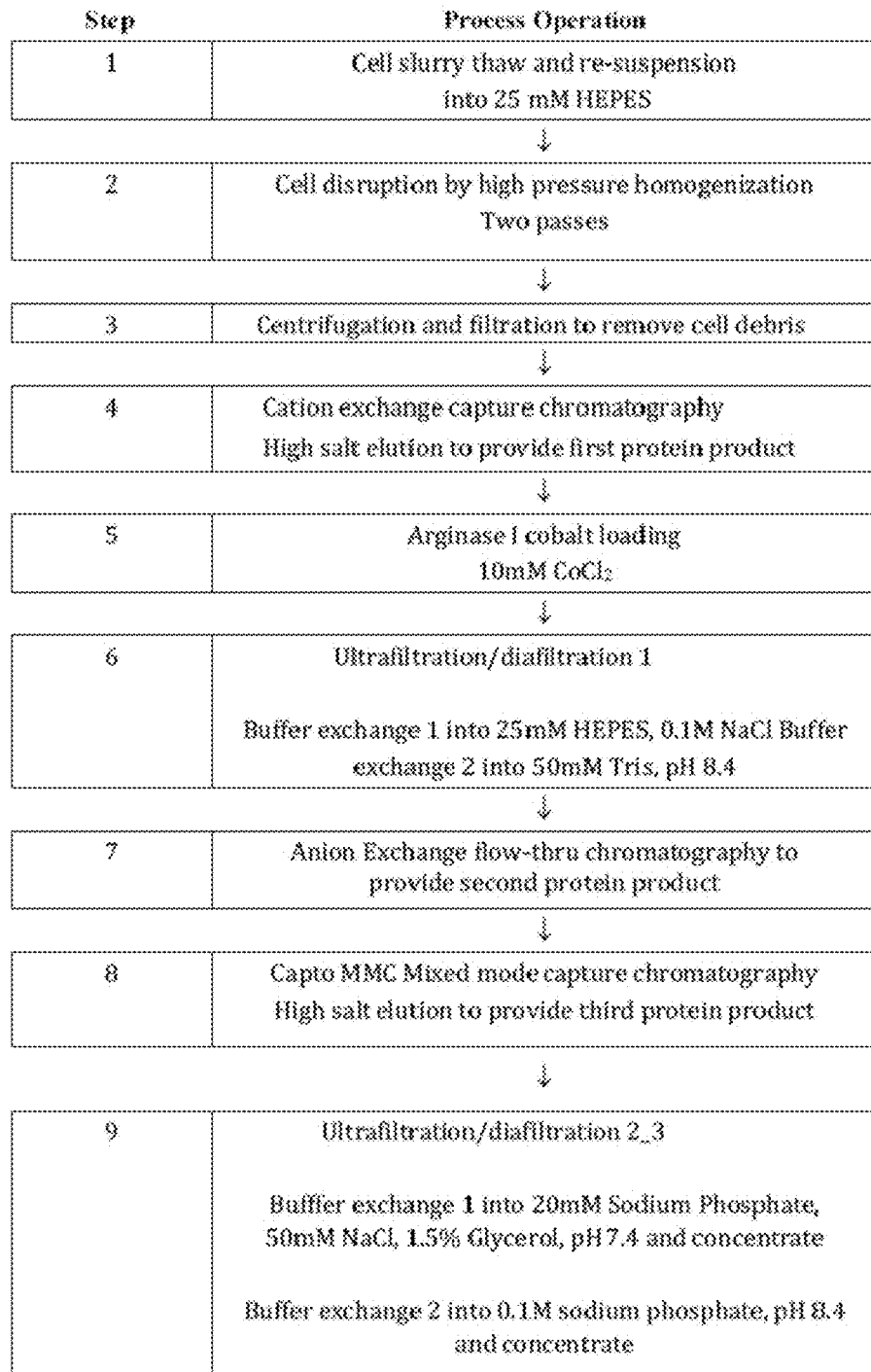
FIG. 2 is a schematic diagram of an exemplary process for the fermentation of E. coli and expression of Arginase 1.
Figure 3A:
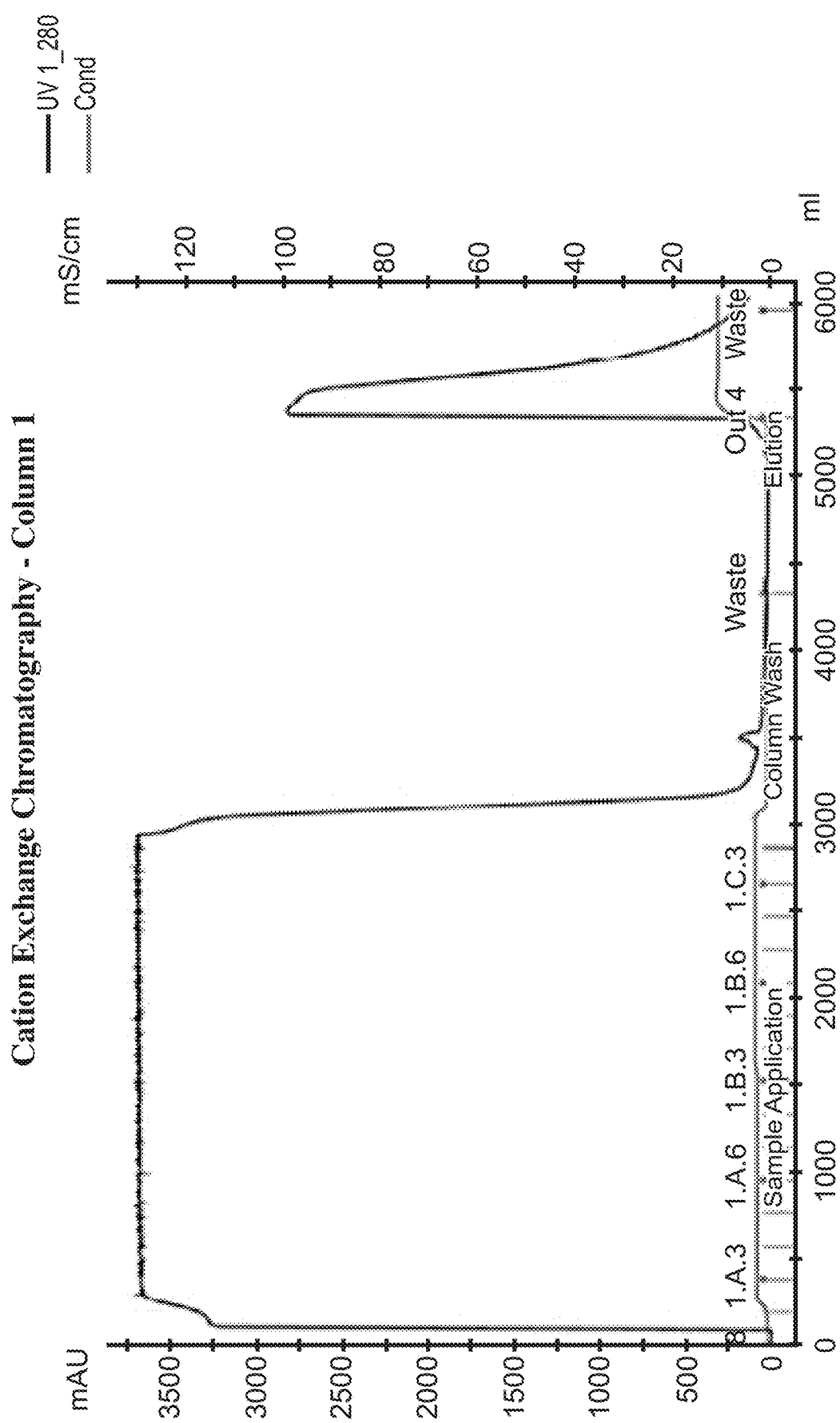
FIGS. 3(a)-3(b) are schematic diagrams of an exemplary process for purification of recombinant human Arginase 1, cobalt-substituted recombinant human Arginase 1 and PEGylated cobalt-substituted recombinant human Arginase 1.
Figure 3B:
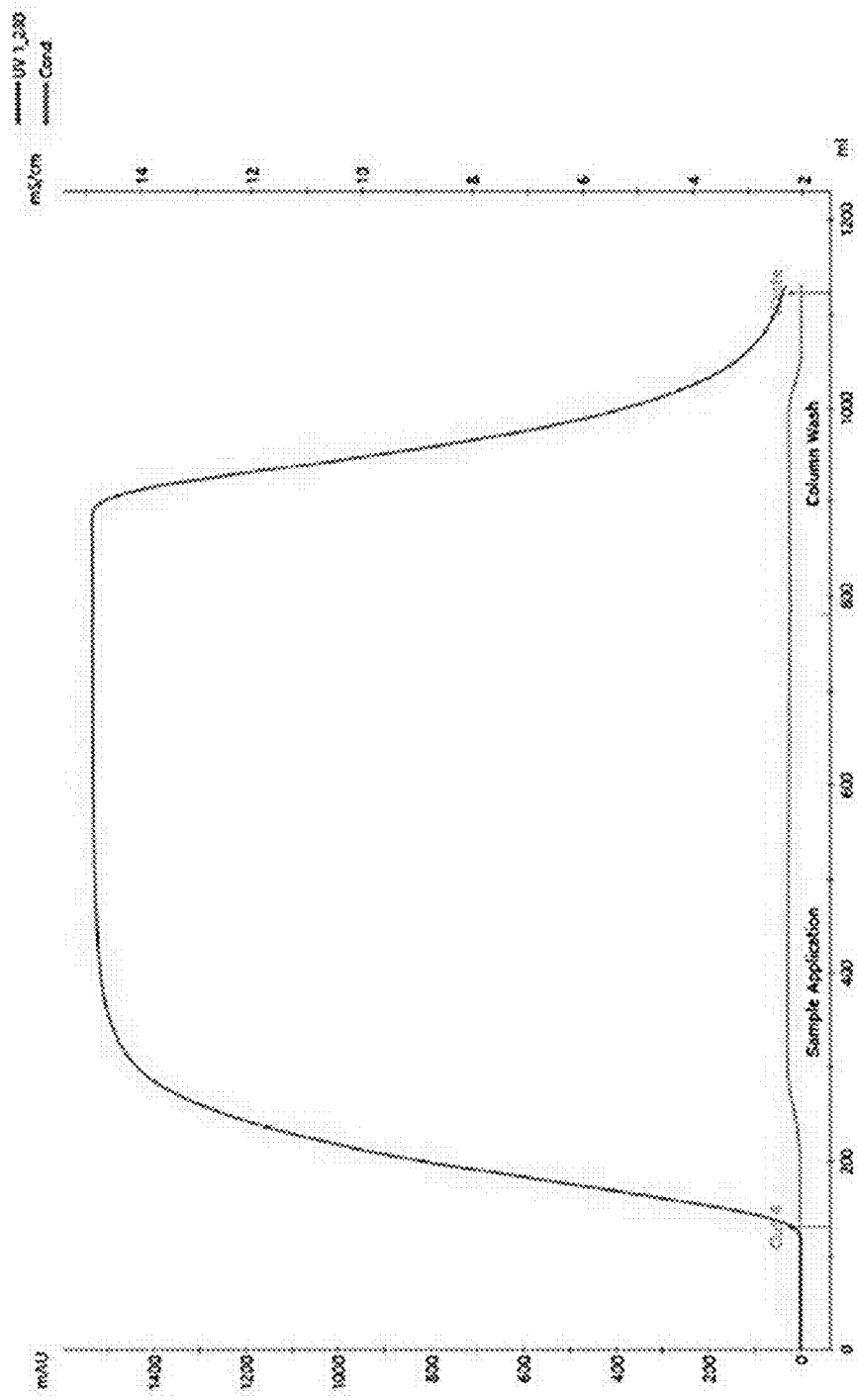
Figure 3C:
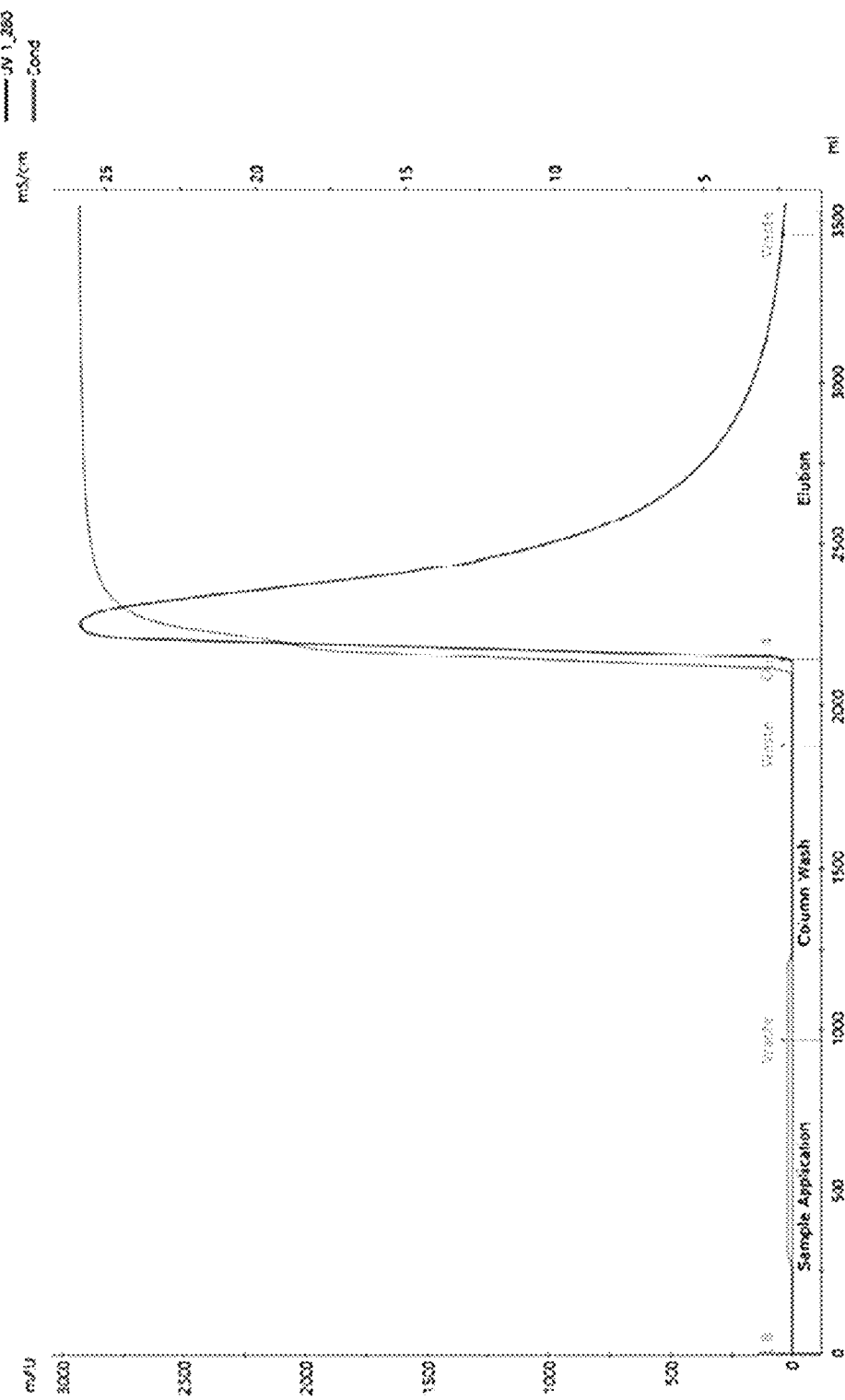

An overview of exemplary upstream and downstream production methods can be seen in FIGS. 2 and 3(a)-3(b).

Shake Flask Expansion

The purpose of the shake flask expansion/fermentation is to generate an inoculum to seed the production fermenter. Shake flask expansion creates cell mass for inoculation of the production reactor as well as extra for analytical purposes. A representative overview of the Arginase 1 fermentation processes can be seen in FIG. 2.

An aliquot of the inoculum medium is introduced into one 500 mL flask (a Primary flask) and six 3 L disposable flasks (Secondary flasks). The flasks are autoclaved, and post-sterile additions are transferred to each flask. Prior to inoculation, the primary medium is pre-warmed to the processing temperature of 37° C. Before secondary inoculation, the secondary flasks are pre-warmed to the processing temperature of 37° C.

One vial of an Arginase 1-expressing E. coli working cell bank (WCB) is removed from cold storage and thawed. A target volume of thawed cells (approximately 1.1 mL) is added aseptically to the primary flask, and the flask is incubated at 37° C. with agitation. Samples are removed from the flask hourly starting several hours post-inoculation to follow cell growth by optical density at 600 nm (OD600). Once the target OD600 of ≥1.0 is reached in the primary flask, a target volume (15 mL) of primary culture is aseptically transferred into each secondary flask. The secondary flasks are incubated at 37° C. with agitation. Samples are removed from one secondary flask hourly starting at 4 h post-inoculation, increasing to every 30 min once the OD600 has reached ≥1.5. When the measurement has met the specified density of ≥2.0 OD600, the remaining secondary flasks are sampled. If the average OD600 of all secondary flasks meets a specified transfer criterion, the flasks are pooled, and the inoculum is transferred to the production fermenter. A representative overview of the fermentation process for Arginase 1 can be seen in FIG. 2.

Production Fermentation

The purpose of the Production Fermentation is to expand the shake flask culture and induce production of Arginase 1. Production fermentation can create large scale quantities of Arginase 1. Following a shake flask expansion phase to build cell mass, the fermentation process produces Arginase 1 (in E. coli) as a soluble protein. In one embodiment a 1500 L fermenter contains the initial batch medium including sterile additions before inoculation. After inoculation, inputs to the fermenter include nutrient feed, antifoam solution, addition of acid or base to maintain culture pH. A secondary vessel holds the nutrient feed medium. An automated control strategy maintains important parameters for consistent cell growth including dissolved oxygen, sparge rate, agitation rate, pH, pressure, and temperature. Arginase 1 expression is induced by addition of IPTG (isopropyl betta-D-1-thiogalactophranoside), with harvest occurring approximately 18 hours later. The performance of the fermenter is assessed at the end of production by monitoring cell density, percent solids, and the proportion of soluble Arginase 1.

In a preferred embodiment, the fermentation medium is prepared directly in the production fermenter. Purified water is added to the fermentation medium to the required weight before in-place sterilization (SIP). Post-sterilization additions of kanamycin, glucose, and potassium phosphate are filter-sterilized into the production fermenter once the medium has cooled. If necessary, the sterile medium is brought to a designated pre-inoculation weight with purified water using a 0.2 µm sterile filter. The fermentation medium is titrated with base (ammonium hydroxide) to a controlled pH value.

The production fermenter at 37° C. is inoculated aseptically using a pooled inoculum via a pressure-assisted transfer. Fermentation broth samples are collected at a regular frequency and measured for OD600 analysis from the time of inoculation until fermentation cool down. Glucose samples are taken at a regular interval beginning at 3 h post-inoculation and increasing in frequency after 9 h post-inoculation. Antifoam solution is added as needed during the fermentation process to avoid excessive foaming of the culture. Dissolved oxygen is controlled by an agitation cascade with oxygen sparge on demand. Culture pH is maintained using acid and base inputs. Growth medium is preferably maintained at 36-38° C. and at a pH of 7.0-7.4 with agitation and aeration.

The nutrient feed consists of yeast extract, Martone B-1, L-cysteine HCl, and glycerol. The feed starts when the glucose concentration is less than 10 g/L (12-14 h post-inoculation) and continues at a fixed rate until the end of production. Expression is triggered with addition of IPTG. Induction continues for 18 hours. Completion of the fermentation process is followed by a cool down in preparation for harvest operations. The production fermenter can generate titers of soluble Arginase 1 of approximately 6 g/L. An overview of the Production Fermentation can be seen in FIGS. 3(a)-3(b).

Harvest Operations

Harvest operations capture cells containing soluble Arginase 1, break open the cells/lyse the cells, and clear the lysate of cell debris by using centrifugation and/or filtration. The recovered cell slurry can be frozen or kept at a low temperature for long-term storage. Harvest operations may collect the cells by centrifugation, lysed with two passes through a homogenizer or cell disruption under pressure (French press), centrifuged a second time, and membrane filtered prior to the first chromatography step.

In a preferred embodiment, whole cells are separated from fermentation medium using a disc stack centrifuge. The resulting cell slurry resuspended in 25 mM HEPES, pH 7.6, followed by two passes through a homogenizer. The pH of the 25 mM HEPES can also be used in the range of pH 7.2-7.6. The lysed material is clarified using a centrifuge to remove cell debris, then membrane filtered through 0.24 µm grade filters. In a preferred embodiment, harvest steps are performed at a target temperature of ≤15° C.

In an alternative embodiment, cell disruption is performed using high pressure. Cell slurry is transferred to a homogenizer at a controlled rate and the homogenized outflow is passed through a heat exchanger to reduce the temperature increase seen during pressure homogenization. The chilled cells undergo two homogenization passes. The first pass lysis pool is transferred from the collection vessel back to the feed vessel. The hold duration between passes is minimized to reduce potential microbial growth.

The post-lysis material is clarified by centrifugation to remove cellular debris from the soluble components of the lysate. The lysate is transferred at a controlled rate to a disk-stack, intermittent discharge, centrifuge. The clarified lysate is collected for further processing.

The clarified lysate is filtered, such as with an about 0.2 µm filter. Process transition filters can also be used for microbial control during process operations. For this purpose, filters can be either 0.5 µm or 0.2 µm filters. This step also removes small particulates from clarified material that may not have separated during clarification operations. Prior to use, the filters are flushed extensively with purified water and equilibrated with 25 mM HEPES, pH 7.6 buffer. Each downstream process step can be preceded by a pre-filter to mitigate the potential for bioburden load.

Purification of rhARG1, Co-rhARG1 and Co-rhARG1-PEG

Regardless of the methods used to culture cells that express the rhARG1 (e.g. the fermentation processes described above), the purification methods described herein can be used to capture rhARG1 and further purify the enzyme. The purification methods can include optional steps such as loading with cobalt to produce Co-rhARG1 and/or reacting with a PEGylation reactant to provide Co-rhARG1-PEG.

Various embodiments of the purification process relate to the use of a cation exchange (CEX) column to capture rhARG1. In one or more embodiments, the CEX column is the first column ("Column 1") in system with multiple chromatography columns. The protein product eluted from this Column 1 is "First Protein Product".

In one or more embodiments, Column 1 uses cation exchange chromatography to bind rhARG1 at a pH in the range of about 7 to about 8, such as a pH of about 7.6. In one or more embodiments, the rhARG1 is bound in the absence of salt or at low salt concentrations. In one or more embodiments, the rhARG1 is eluted with a buffer having a high salt (e.g. NaCl) concentration, such as up to about 0.5 M NaCl. Exemplary salt concentrations include about 0.01, about 0.02, about 0.03, about 0.04, about 0.05, 0.1, about 0.2, about 0.3, about 0.4 and about 0.5 M NaCl.

In various embodiments, a salt gradient is used to separate different charge variants of rhARG1. Exemplary salt gradients are from about 0 to about 0.5 M NaCl, about 0 to about 0.4 M NaCl, about 0 to about 0.3 M NaCl, about 0 to about 0.2 M NaCl or about 0 to about 0.1 M NaCl.

In one or more embodiments, the method further comprises loading the First Protein Product (optionally after cobalt substitution) onto an anion exchange (AEX) chromatography column ("Column 2") and collecting the flow-through to provide a second protein product ("Second Protein Product"). In another aspect of the methods, the method further comprises loading the Second Protein Product onto third column which captures the Arginase 1 and is then eluted to provide a third protein product ("Third Protein Product"). In some embodiments, this third chromatography column ("Column 3") may be a size exclusion chromatography (SEC) column or a multimodal chromatography (MMC) column.

Various embodiments provide that the rhARG1 is loaded with Co to replace the Mn cofactor. In one or more embodiments, the Co loading is performed using a $Co^{2+}$ salt such as $CoCl_2$. Incubation times are temperature dependent, such that lower cobalt substitution temperatures require longer incubation times and higher cobalt substitution temperatures do not require as long incubation times. The cobalt loading temperature may be as low as 1° C. or greater than 50° C. and corresponding incubation times can be as long as over 8 hours or less than 10 minutes.

Various embodiments provide that the rhARG1 or Co-rhARG1 is reacted with a PEGylation reactant such as methoxy PEG succinimidyl carboxymethyl ester (MW 5000). The PEGylation reactant is typically provided in molar excess of 10-40 compared to the enzyme. Incubation times can be in the range of 0.5 to 4 hours. The pH during PEGylation can be about 8 to about 9, such as a pH of about 8.4.

In one or more embodiments, the purified PEGylated proteins, rhARG1 or Co-rhARG1, comprises Arginase I monomer, Gluconoylated Arginase I, Phosphogluconoylayted Arginase I, 2×Gluconoylated Arginase I, Gluconoylated+phosphogluconoylated Arginase I and 2×Phosphogluconoylated Arginase I.

In some embodiments, the purified PEGylated proteins, rhARG1 or Co-rhARG1, comprises at least 70% of Arginase I monomer. Exemplary amounts include at least 70%, at least 75, at least 80%, at least 85%, or at least 90% Arginase I monomer. In some embodiments, the purified PEGylated proteins, rhARG1 or Co-rhARG1, comprises less than 10% of Gluconoylated Arginase I. Exemplary amounts include about 1%, about 2%, about 3%, about 4%, about 5%, about 6%, about 7%, about 8% or about 9% Gluconoylated Arginase I, or any range in between these values In some embodiments, the purified PEGylated proteins, rhARG1 or Co-rhARG1, comprises less than 10% of Phosphogluconoylayted Arginase I. Exemplary amounts include about 1%, about 2%, about 3%, about 4%, about 5%, about 6%, about 7%, about 8% or about 9% Phosphogluconoylated Arginase I, In some embodiments, the purified PEGylated proteins, rhARG1 or Co-rhARG1, comprises at least 70% of Arginase I monomer, less than 10% of Gluconoylated Arginase I, and less than 10% of Phosphogluconoylayted Arginase I.

Imaged capillary isoelectric focusing (iCIEF) provides a measurement of consistency for pegylated protein due to the level of heterogeneity in the PEGylated trimer. In one or more embodiments, the iclEF analysis of purified PEGylated protein, rhARG1 or Co-rhARG1, comprises nine distinctively peaks, peak-1, peak-2, peak-3, peak-4, peak-5, peak-6, peak-7, peak-8 and peak-9, each corresponding to nine distinctively charged species, species-1, species-2, species-3, species-4, species-5, species-6, species-7, species-8 and species-9. The area under curve for each peak corresponds to the proportion of that particular species. In one or more embodiments, certain peaks may be combined together for related species such as peaks-1+2 or peaks-3+4.

In some embodiments, the purified PEGylated protein, rhARG1 or Co-rhARG1, comprises the area under curve for peak-1 in the proportion of less than about 30%, less than about 25%, less than about 20%, less than about 15%, and less than about 10%.

In some embodiments, the purified PEGylated protein, rhARG1 or Co-rhARG1, comprises the area under curve for peak-2 in the proportion of less than about 40%, less than about 35%, less than about 30%, less than about 25%, less than about 20%, less than about 15%, and less than about 10%.

In some embodiments, the purified PEGylated protein, rhARG1 or Co-rhARG1, comprises the area under curve for combined peaks-1+2 in the proportion of less than about 50%, less than about 45%, less than about 40%, less than about 35%, less than about 30%, less than about 25%, less than about 20%, less than about 15%, and less than about 10%.

In some embodiments, the purified PEGylated protein, rhARG1 or Co-rhARG1, comprises the area under curve for peak-3+4 in the proportion range of about 2% to about 40%, about 2% to about 35%, about 2% to about 30%, about 2% to about 25%, about 4% to about 40%, about 4% to about 35%, about 4% to about 30%, about 4% to about 25%, about 6% to about 40%, about 6% to about 35%, about 6% to about 30%, about 6% to about 25%, about 8% to about 40%, about 8% to about 35%, about 8% to about 30%, about 8% to about 25%, about 10% to about 40%, about 10% to about 35%, about 10% to about 30%, and about 10% to about 25%.

In some embodiments, the purified PEGylated protein, rhARG1 or Co-rhARG1, comprises the area under curve for peak-5 in the proportion range of about 5% to about 40%, about 5% to about 35%, about 5% to about 30%, about 5% to about 25%, about 10% to about 40%, about 10% to about 35%, 10% to about 30%, about 10% to about 25%, about 15% to about 40%, about 15% to about 35%, about 15% to about 30%, and about 15% to about 25%.

In some embodiments, the purified PEGylated protein, rhARG1 or Co-rhARG1, comprises the area under curve for peak-6 in the proportion range of about 2% to about 35%, about 2% to about 30%, about 2% to about 25%, about 2% to about 20%, about 4% to about 35%, about 4% to about 30%, about 4% to about 25%, about 4% to about 20%, about 6% to about 35%, about 6% to about 30%, about 6% to about 25%, about 6% to about 20%, about 8% to about 35%, about 8% to about 30%, about 8% to about 25%, about 8% to about 20%, about 10% to about 35%, about 10% to about 30%, about 10% to about 25%, and about 10% to about 20%.

In some embodiments, the purified PEGylated protein, rhARG1 or Co-rhARG1, comprises the area under curve for peak-7 in the proportion of less than about 35%, less than about 30%, less than about 25%, less than about 20%, less than about 15% and less than about 10%.

In some embodiments, the purified PEGylated protein, rhARG1 or Co-rhARG1, comprises the area under curve for peak-8 in the proportion of less than about less than about 25%, less than about 20%, less than about 15%, less than about 10% and less than about 5%.

In some embodiments, the purified PEGylated protein, rhARG1 or Co-rhARG1, comprises the area under curve for peak-9 in the proportion of less than about 18%, less than about 16%, less than about 14%, less than about 12%, less than about 10%, less than about 8%, less than about 6%,and less than about 4%.

Administration of rhARG1, Co-rhARG1 and Co-rhARG1-PEG

The rhARG1, Co-rhARG1 and Co-rhARG1-PEG as described herein (and compositions comprising them) can be administered via any appropriate route, including intravenously, intrathecally, subcutaneously, intramuscularly, intratumorally, and/or intraperitoneally. In one or more embodiments, the rhARG1, Co-rhARG1 and Co-rhARG1-PEG (or compositions comprising them) are administered intravenously (IV) or subcutaneously (SC).

Compositions containing rhARG1, Co-rhARG1 and Co-rhARG1-PEG thereof can be provided in formulations together with physiologically tolerable liquid, gel or solid carriers, diluents, and excipients. Such compositions are typically prepared as liquid solutions or suspensions, as injectables. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Exemplary methods and instructions regarding the administration of rhARG1, Co-rhARG1 and Co-rhARG1-PEG (e.g. pegzilarginase) are provided below. Although the following description is specific to pegzilarginase, the methods and instructions are also applicable to other recombinant Arginase 1 and 2 enzymes.

Recommended Intravenous Dosage Regimen

Obtain a baseline plasma arginine concentration before initiating treatment. The initial recommended dosage of pegzilarginase for ARG1-D patients administered once weekly as a single intravenous infusion is 0.10 mg/kg. If the initial dose of 0.10 mg/kg does not reduce plasma arginine to levels ≤150 micromol/L, then the dose may be adjusted up to a maximum of 0.20 mg/kg once weekly. If during treatment, plasma arginine levels fall below 50 micromol/L, then consider reducing the dosage. Upon administration of 5 or more IV doses of pegzilarginase, consider using subcutaneous administration of pegzilarginase for ARG1-D patients and continue to periodically monitor plasma arginine levels.

Recommended Subcutaneous Dosage Regimen

When transitioning from pegzilarginase intravenous therapy to subcutaneous administration, administer the first subcutaneous dose instead of the next scheduled intravenous dose. The initial subcutaneous dose should be the same mg/kg dose as the last IV dose administered. The subcutaneous dose may be modified as clinically indicated to ensure plasma arginine levels remain in the range of 5-150 micromol/L.

Blood Arginine Monitoring

After initiating treatment with pegzilarginase, plasma arginine monitoring should be performed until the patient's plasma arginine level is inside the target range of 50 to 150 µmol/L. Thereafter, periodic plasma arginine monitoring is recommended to assess blood arginine control. Upon changing to subcutaneous dose administration or when making changes to diet, additional plasma arginine monitoring may be required.

Preparation and Administration Instructions

Pegzilarginase is supplied as a frozen liquid formulation in 10 mL single-use glass vials that contain 5 mL of pegzilarginase at a concentration of either 1 mg/mL or 5 mg/mL. Each single-use glass vial of pegzilarginase is intended for use as a single intravenous injection or as a subcutaneous injection. Inspect pegzilarginase visually for particulate matter and discoloration prior to administration. Pegzilarginase is a colorless to slightly yellow or slightly pink solution. Discard if discolored, cloudy or if particulate matter is present in the vial. Remove the flip-top from the vial. Wipe the rubber stopper of the vial with alcohol swabs to disinfect. Use a sterile syringe with an 18 G needle to remove the appropriate volume of drug from the vial. If more than one vial is required, please use a separate needle to draw the solution from each vial. Calculate the solution to be withdrawn from the vial for use in the syringe pump. Once the appropriate volume of drug has been drawn into the syringe, draw normal saline using a separate needle to achieve a total volume of 40 mL. Calculate the required amount of drug to be used as follows:

Amount of 1.0 mg/mL pegzilarginase =

$$\text{Patient Weight(kg)} \times \text{dose level (mg/kg)}$$

Amount of 5.0 mg/mL pegzilarginase =

$$\frac{\text{Patient Weight(kg)} \times \text{dose level (mg/kg)}}{5}$$

Administer pegzilarginase via intravenous infusion over 30 minutes using a syringe pump.

TABLE 2

Weight-Based Dosing for Administration of 0.1 mg/kg Once Weekly

| Body Weight (kg)* | Volume to Inject (mL) | Vial Configuration |
|---|---|---|
| 3 | 0.30 | 1 mg/mL |
| 4 | 0.40 | 1 mg/mL |
| 5 | 0.50 | 1 mg/mL |
| 6 | 0.60 | 1 mg/mL |
| 7 | 0.70 | 1 mg/mL |
| 8 | 0.80 | 1 mg/mL |
| 9 | 0.90 | 1 mg/mL |
| 10 | 1.0 | 1 mg/mL |
| 15 | 1.5 | 1 mg/mL |
| 20 | 2.0 | 1 mg/mL |
| 25 | 2.5 | 1 mg/mL |
| 30 | 3.0 | 1 mg/mL |
| 35 | 3.5 | 1 mg/mL |
| 40 | 4.0 | 1 mg/mL |
| 50 | 5.0 | 1 mg/mL |
| 60 | 1.20 | 5 mg/mL |
| 70 | 1.40 | 5 mg/mL |
| 80 | 1.60 | 5 mg/mL |

In one or more embodiments, the volume for a subcutaneous injection has a maximum volume, such as a maximum of 2 mL/injection for adult patients and/or a maximum volume of 1 mL/injection for pediatric patients. If the calculated volume for subcutaneous administration is greater than a maximum volume, then a higher vial concentration may be used (e.g. 5 mg/mL instead of 1 mg/mL) and/or the volume may be split into multiple smaller injections (e.g. a 4 mL injection is split into 2 injections of 2 mL each).

Dosage Forms and Strengths pegzilarginase injection is a colorless to slightly yellow or slightly pink solution available as follows in 10 mL vials:
  a. Solution for Injection: 5 mL of 1.0 mg/mL
  b. Solution for Injection: 5 mL of 5.0 mg/mL

Warnings and Precautions

Hypersensitivity reactions may occur with administration of pegzilarginase. Monitor all patients for signs and symptoms of acute allergic reactions (e.g. urticaria, pruritus, erythema, hypotension, tachycardia) during and following pegzilarginase infusion. In case of severe hypersensitivity reactions, slow or discontinue the administration of pegzilarginase immediately and administer appropriate medical care. Consider premedication of patients with a non-sedating antihistamine prior to dosing. In the event that corticosteroids are required, they should be used with caution due to their potential to cause hyperammonemia.

Pregnancy: Pregnancy Category B

Reproduction studies have been performed in mice and rats at doses up to 100 mg/kg. There was no evidence of harm to the fetus due to pegzilarginase. There are, however, no adequate and well-controlled studies in pregnant women. Because animal reproduction studies are not always predictive of human response, pegzilarginase should be used during pregnancy only if clearly needed.

Nursing Mothers

It is not known if pegzilarginase is present in human milk. The developmental and health benefits of breastfeeding should be considered along with the mother's clinical need for pegzilarginase and any potential adverse effects on the breastfed child from the drug.

Description

Pegzilarginase is a cobalt substituted, recombinant human arginase I enzyme that is covalently conjugated to monomethoxy polyethylene glycol (mPEG) that acts by catalyzing the same reaction as arginase 1, converting arginine into ornithine and urea. Human arginase 1 is a binuclear manganese metalloenzyme. To produce pegzilarginase, the manganese cofactor is replaced with cobalt to yield Co-Arginase I. The substitution of the native manganese (Mn+2) with cobalt (Co+2) in the active site of arginase I enhances the stability and catalytic activity at physiological pH. Pegylation extends the circulating half-life. The average molecular weight of pegzilarginase is approximately 284 kDa. Pegzilarginase has a specific activity ranging from approximately 320-600 units per mg of protein content. One activity unit is defined as the amount of enzyme required to convert 1 micromole of arginine to ornithine per minute at 37° C.

Pegzilarginase is intended for intravenous or subcutaneous infusion and is supplied as a sterile, clear, colorless to slightly yellow or slightly pink solution formulated at a 1 mg/mL and at a 5 mg/mL concentration in a buffer containing 50 mM sodium chloride, 5 mM potassium phosphate, and 1.5% w/v glycerol, at a pH of 7.4. It is provided as a preservative-free, sterile solution in a clear, single-use, glass vial. Each vial of 1 mg/mL pegzilarginase drug product contains 5 mL of drug product (5 mg pegzilarginase per vial). Each vial of 5 mg/mL pegzilarginase drug product contains 5 mL of drug product (25 mg pegzilarginase per vial). Vials are stoppered with a coated rubber stopper and sealed with an aluminum flip off seal and are stored frozen at ≤−60° C. and thawed before use.

Pharmacodynamics pegzilarginase treatment of adults and pediatric patients with Arginase 1 Deficiency resulted in the reduction of blood arginine concentrations from pre-treatment baseline values into the normal blood arginine range of 40 to 115 micromole/L. Maximum suppression of L-arginine was observed at approximately 8 hours post-dose, decreasing in a dose dependent manner with recovery to pre-dose levels occurring by 168 hours post dose. A strong correlation was observed between pegzilarginase and arginine, with an immediate suppressive effect on arginine following IV administration, and the maximum decrease of arginine concentration being reached within 24 hours post-dose.

Pharmacokinetics

Following IV administration to 14 subjects, pharmacokinetic samples were collected throughout the dosing interval from 0-168 hours to characterize the relationship between pegzilarginase pharmacokinetics and arginine. Across the dose range (0.015 mg/kg-0.2 mg/kg), pegzilarginase exposure, as measured by $C_{max}$ and $AUC_{0-168}$, increased approximately proportional to dose, with a 13-fold increase in dose resulting in a 14-fold increase in $C_{max}$ and $AUC_{0-168}$. No accumulation of pegzilarginase was observed following a once weekly IV dosing regimen, with a $T_{1/2}$ of approximately 30 hours across the dose range, and low to moderate inter-subject variability (13-46% CV) in the exposure metrics.

Animal Toxicology and/or Pharmacology

The pharmacologic effects of pegzilarginase on arginine levels were assessed in a neonatal transgenic mouse model of Arginase I and a tamoxifen-induced arginase deficiency model in adult mice. These models mimic the human disease in that a significant excess of circulating arginine and catabolites of arginine are present; however, unlike humans with Arginase I Deficiency, these animals develop severe and generally lethal hyperammonemia. Pharmacologic effects also were assessed in a rat arginine-induced model of hyperargininemia. Pegzilarginase reduced plasma arginine levels in a dose-dependent manner.

The potential toxicity and TK of pegzilarginase were evaluated in postnatal day (PND) 21 (equivalent to a 2-year old human) juvenile rats administered once weekly IV bolus injections at 0.1, 0.3, and 1.0 mg/kg for 6 months followed by a 6-week recovery period. Pegzilarginase was well tolerated, with no test article-related mortality and no significant test article effects observed on: food consumption, coagulation, urinalysis, ophthalmoscopic examinations, sexual maturation, growth hormone analyses, bone marrow analyses, functional observation battery (FOB) evaluations and neurobehavioral testing (auditory startle habituation, motor activity, or Morris water swim maze). There were no pegzilarginase-related macroscopic findings at the end of the 6-month terminal and 6-week recovery intervals. Adverse microscopic changes were limited to the testes and epididymides and correlated with reduced weight of male reproductive organs and adverse sperm analyses findings at 0.3 and 1.0 mg/kg. At 1.0 mg/kg, an adverse effect was observed on sperm analyses with reduced sperm motility, lower caudal epididymal sperm counts, decreased sperm concentration, and increased percentage of abnormal sperm observed. These observations were considered a direct treatment-related effect and correlated with microscopic changes of subtle tubular degeneration in the testes at 0.3 mg/kg and 1.0 mg/kg. Following the 6-week recovery period for the control and 1.0 mg/kg groups, these changes were overall reversible with the exception of the increased percentage of abnormal sperm and sperm counts. The partial reversibility after 6 weeks was not unexpected because the normal sperm development cycle is approximately 9 weeks or longer than the 6-week recovery period.

Importantly, there were no apparent PEGylation effects observed by histopathology. Toxicokinetic data indicated that pegzilarginase exposure was maintained throughout the study. In conclusion, the NOAEL in females was 1.0 mg/kg. In males, the NOAEL was 0.1 mg/kg based on microscopic changes in the testes at 0.3 mg/kg and 1.0 mg/kg.

The potential toxicity and TK of pegzilarginase were evaluated following once weekly intravenous bolus injection to cynomolgus monkeys at doses of 0.1, 0.3, and 1.0 mg/kg for 13 weeks followed by a 4-week recovery period. Clinical signs observed at 1.0 mg/kg included decreased body weight, increased incidences of sparse hair (entire body), dry/discolored skin (entire body), tremors, inappetence, watery feces, decreased activity, ataxia, muscle wasting, and/or unkempt/hunched appearance. No treatment-related effects were noted in clinical pathology parameters (coagulation, growth hormone, and urinalysis), ECG and ophthalmic examinations, respiratory rate, and blood pressure assessments.

How Supplied/Storage and Handling

Pegzilarginase is supplied as a solution for injection.

Pegzilarginase is supplied frozen (≤−60° C.). Diluted pegzilarginase should be used immediately. If immediate use is not possible, diluted pegzilarginase may be stored for up to 8 hours at 2° C. to 8° C. (36° F. to 46° F.) during administration.

EXAMPLES

Before describing several exemplary embodiments of the disclosure, it is to be understood that the disclosure is not limited to the details of construction or process steps set forth in the following description. The disclosure is capable of other embodiments and of being practiced or being carried out in various ways.

In the experimental disclosure which follows, the following abbreviations apply: eq (equivalents); M (Molar); µM (micromolar); mM (millimolar); N (Normal); mol (moles); mmol (millimoles); µmol (micromoles); nmol (nanomoles); g (grams); mg (milligrams); µg (micrograms); L (liters); ml (milliliters); µl (microliters); cm (centimeters); mm (millimeters); µm (micrometers); nm (nanometers); MW (molecular weight); PBS (phosphate buffered saline); min (minutes).

Example 1

Cation Exchange Column Chromatography (Column 1)

In a preferred embodiment, Arginase 1 is captured on a cation exchange column (CEX) to reduce product-related impurities and process-related impurities such as host cell proteins (HCP), DNA, and endotoxin (see FIGS. 3(a)-3(b) for an overview of the purification process). In a particular embodiment, the first column (Column 1) chromatography step in the Arginase 1 purification process uses SP Sepharose FF resin and an inlet heat exchanger. Column 1 uses cation-exchange chromatography to bind Arginase 1 in the absence of salt at pH 7.6, and elute with a buffer of increased salt concentration (FIG. 4(a)). In one embodiment the salt is NaCl and the elution from Column 1 is performed with 25 mM HEPES, 0.1M NaCl, pH 7.2-7.6 at room temperature. However, alternative embodiments are possible such as application of a NaCl gradient to Column 1.

Figure 4A:
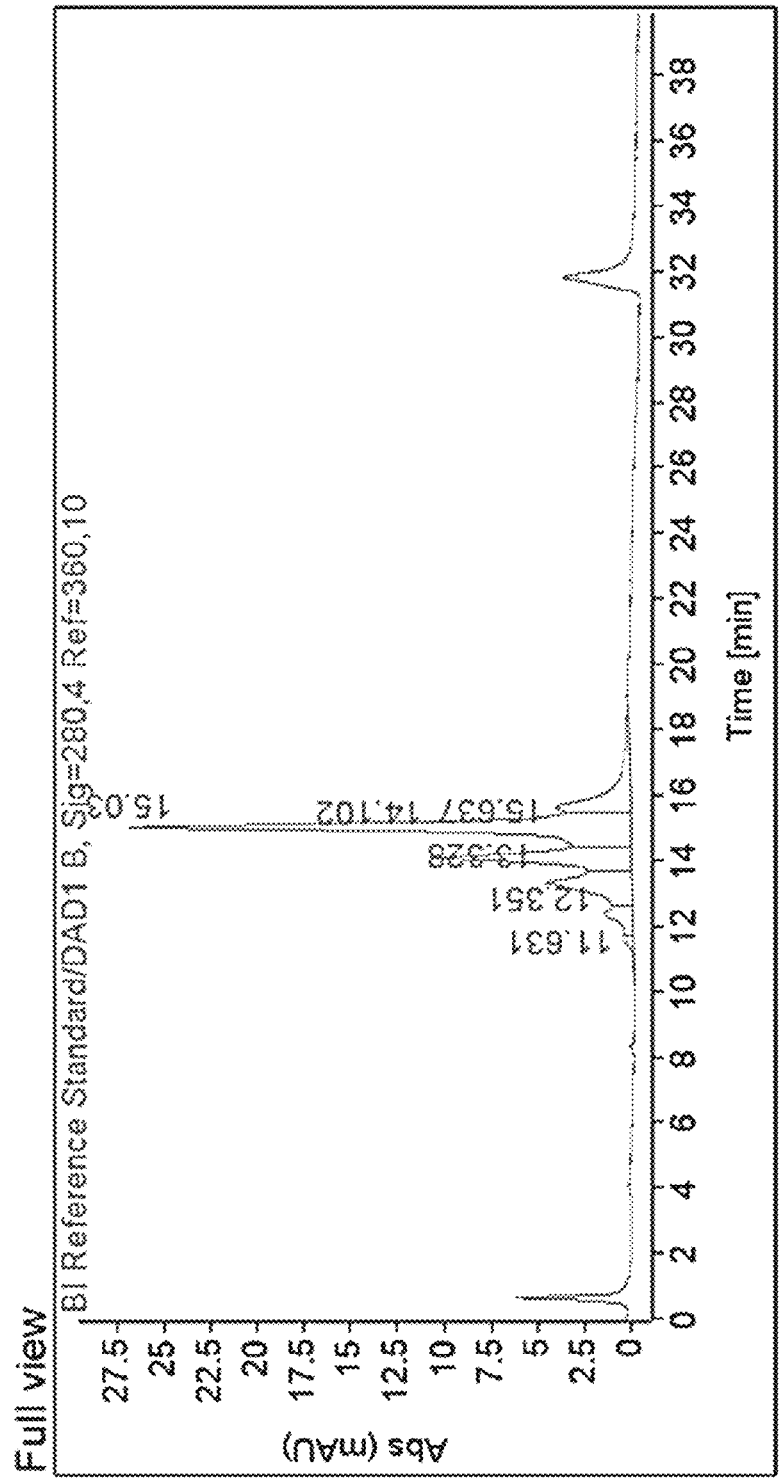
FIGS. 4(a)-4(c) show column chromatography purification of Arginase 1.

FIG. 4(a) shows a representative purification of Arginase 1 on Column 1. Approximately three liters of clarified E. coli lysate were loaded on the cation exchange column. As can be seen from the high level of absorbance at 280 nm, a large amount of protein did not bind onto the column and is detected in the flow through. The column was then washed with approximately two liters of column wash solution. As detected by absorbance at 280 nm, a fraction enriched for Arginase 1 was then eluted with 0.1 M NaCl (final peak).

Example 2

Cobalt Substitution

In a preferred embodiment, the Arginase 1 native manganese co-enzyme is replaced by cobalt. During cobalt substitution (also called cobalt loading), one or both of the two manganese ions normally present in Arginase 1 are replaced with cobalt ions. A wide variety of temperatures can be used for the cobalt substitution step as well as a wide concentration of cobalt (See Table 2). Incubation times for cobalt substitution can be a short as 10 minutes and be performed at over 50° C. Conversely, cobalt loading temperature can be as low as 1° C. or 5° C. and performed for over 8 hours. Also, the higher proportion of cobalt loaded into Arginase 1 leads to a higher specific activity.

The Arginase 1 eluted from Column 1 (also called Column 1 Pool) can be held at room temperature for the cobalt substitution step. In one embodiment, Cobalt Chloride Stock Solution (0.5 M $CoCl_2$) is diluted 50-fold by adding it to Column 1 Pool at a defined rate, with final cobalt chloride concentration at 10 mM. The cobalt substitution is then mixed for two hours at 20° C. In another embodiment, Arginase 1 cobalt loading is performed in a solution of 10 mM $CoCl_2$ for about 2 hours to about 8 hours at room temperature.

An overview of the cobalt loading step can be seen in Table 3.

TABLE 3

Co-Arginase I Cobalt Loading

| Identity | Co (mM) | Temp (° C.) | Time (Min) | Total Co (µg/mg Arginase) | Total Mn (µg/mg Arginase) | Specific Activity (U/mg) |
|---|---|---|---|---|---|---|
| APO-Arginase I* | NA | NA | NA | <0.025 | 0.008 | 24 |
| APO Loading 1* | 0.1 | 5 | 15 | 0.3 | ND | 117 |
| Coh-Arg I* | 10 | 20 | 60 | 2 | 0.06 | 410 |
| APO Loading 2* | 1 | 5 | 15 | 2.4 | ND | 395 |
| APO Loading 3* | 10 | 20 | 15 | 2.8 | ND | 493 |
| APO Loading 4* | 10 | 20 | 60 | 2.9 | ND | 489 |
| APO Loading 5 | 10 | 37 | 15 | 2.8 | ND | NT |
| APO Loading 6 | 10 | 53 | 15 | 2.6 | ND | NT |
| Co-Argl-PEG | 10 | 53 | 15 | 3 | ND | 500 |
| Theoretical | | | | 3.4 | | |

*Graphed

Example 3

Ultrafiltration/Diafiltration 1 (UF/DF 1)

UF/DF 1 removes free cobalt ions and exchanges the Co-Arginase 1 into a solution in preparation for anion exchange chromatography on. The UF/DF1 step uses membranes with a molecular weight cutoff of 30 kDa. One important function of this step is to reduce the levels of free cobalt and buffer exchange the Co-Arginase 1 Pool prior to anion exchange chromatography. Membranes are sanitized with cleaning solution (0.5 N NaOH) and rinsed with water. A normalized water permeability test (NWP) is performed followed by equilibration prior to use in production. Once the UF/DF system is equilibrated, the Co-Arginase 1 Pool is diafiltered against 25 mM HEPES, 0.1 M NaCl, pH 7.6, for three diavolumes, followed by four diavolumes of 50 mM Tris, pH 8.4. After diafiltration, the pool is recirculated and recovered from the system using two times the system's hold-up volume with 50 mM Tris, pH 8.4.

The UF/DF1 membranes are cleaned by performing a 2 M NaCl flush followed by a denaturing cleaning step using 0.5 N NaOH with a 30 minute recirculation. The system is flushed with purified water and the NWP tested to assess the effectiveness of the cleaning procedures. Membranes may be stored in 0.1 N NaOH.

In an alternative embodiment, the first exchange of buffer is into 25 mM HEPES, 0.1M NaCl, pH 7.2-7.6 and the second exchange is into 50 mM Tris, pH 8.1-8.5.

Example 4

Anion Column Chromatography (Column 2)

A preferred embodiment of the Arginase 1 purification uses anther column which is an anion exchange column chromatography ("Column 2"). One embodiment of Column 2 is a Q Sepharose FF resin. One function of this Column 2 step is to reduce process-related impurities such as host-cell DNA and endotoxin from the UF/DF1 pool. Column 2 binds these impurities while Co-Arginase 1 flows though and is collected in the column effluent during the load and wash steps. In one embodiment, the anion exchange flow-thru chromatography for Column 2 is performed with Q Sepharose FF, and up to 40 g protein/L resin is loaded onto the column with buffer 50 mM Tris, pH 8.1-8.5.

Figure 4B:
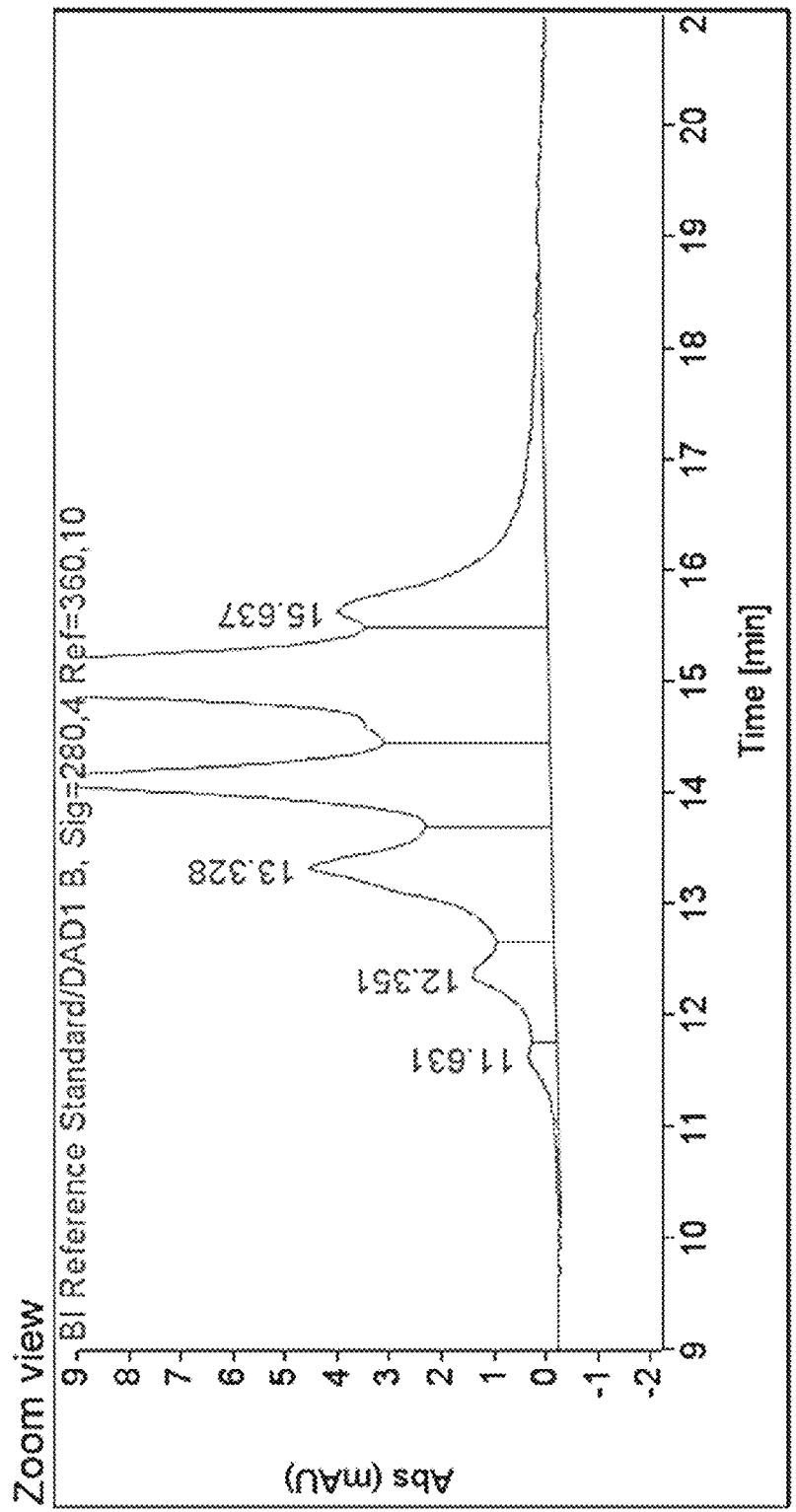

In another embodiment of the methods, the First Protein Product is loaded onto an anion exchange column to capture impurities while Arginase 1 is retrieved in the flow through. FIG. 4(b) is a representative chromatogram of Arginase 1 purification over an anion exchange column (Column 2). As can be seem from absorbance at 280 nm a large amount of protein is detected in the flow through. Impurities are captured on Column 2 and not eluted into the Column 2 Pool (also called Second Protein Product) which is further enriched for Arginase 1.

Example 5

Capto Multimodal Column Chromatography (Column 3)

Figure 4C:
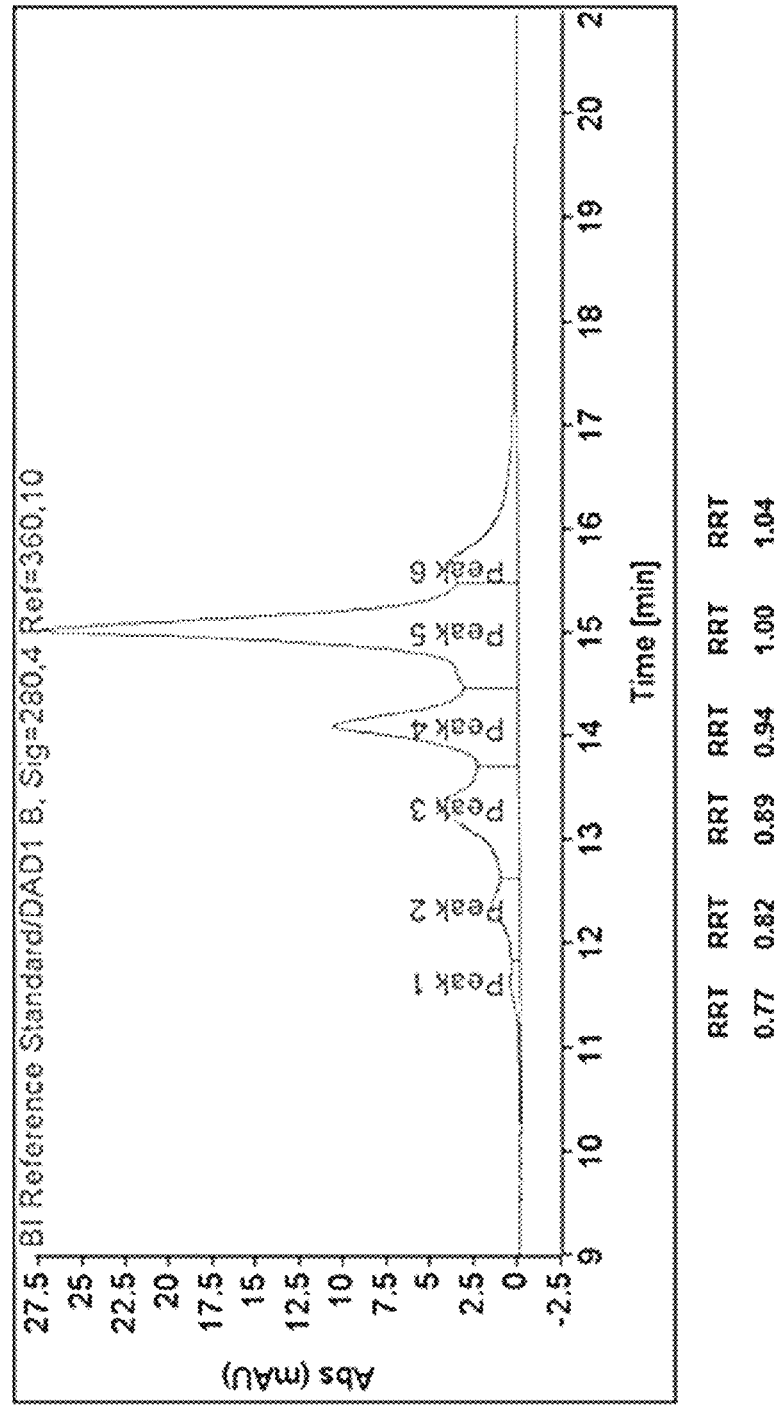
Figure 4D:
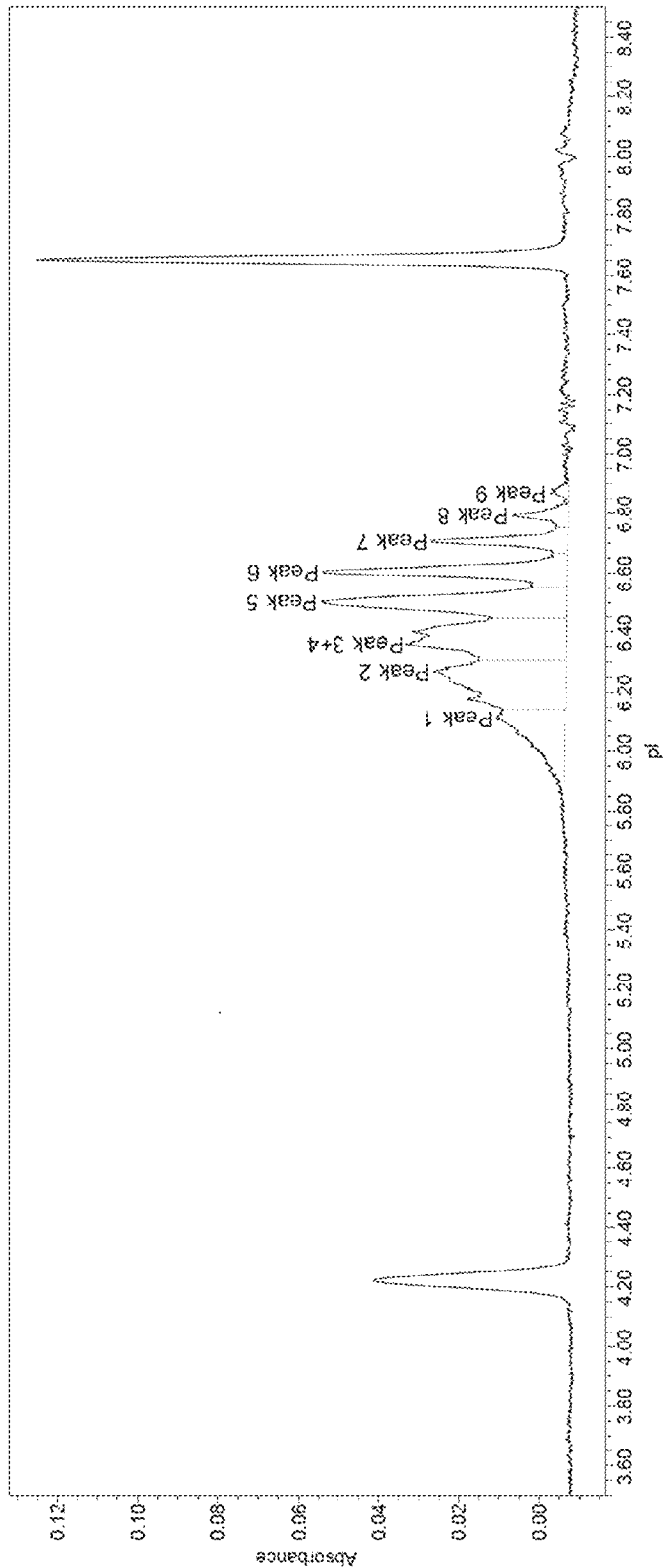

In a preferred embodiment, the Arginase purification process uses a third column chromatography column (Column 3). In one embodiment, Column 3 is a Capto multimodal chromatography (MMC) column or alternatively a size exclusion column. Embodiments that use MMC capture Arginase 1 on the column while process-related impurities such as host cell proteins (HCP), DNA, and endotoxin are washed out in the flow through. In this embodiment, Co-Arginase 1 can be captured by the column in the absence of salt at pH 8.4 and then Co-Arginase 1 eluted with a buffer of increased salt concentration. A representative example of Capto Multimodal Cation exchange chromatography column is shown in FIG. 4(c).

In one embodiment, MMC chromatography (Column 3) uses approximately 15 column volumes to load up to 30 g protein/L resin, and the high salt step elution is performed with 50 mM Tris, 250 mM NaCl, pH 8.1-8.5. In several embodiments, the flow through from the anion exchange column (Column 2) is loaded onto a Capto MMC column at pH 8.4, washed, then the bound Co-Arginase 1 is eluted using 50 mM tromethamine, 250 mM sodium chloride.

Example 6

Ultrafiltration/Diafiltration 2 (UF/DF 2)

UF/DF 2 concentrates Arginase 1 and exchanges the protein into a pre-PEGylated intermediate. The UF/DF2 step uses membranes with a molecular weight cutoff of 30 kDa. An important function of this step is to buffer exchange the Column 3 Pool of the un-PEGylated Co-Arginase 1 intermediate prior PEGylation (or prior to additional filtration and storage). Membranes are sanitized with cleaning solution (0.5 N NaOH) and rinsed with water. Once the UF/DF system is equilibrated, Column 3 Pool (also called Third Protein Product) is diafiltered against 20 mM sodium phosphate, 50 mM sodium chloride, 1.5% (w/v) glycerol, pH 7.4, for five diavolumes. If the Column 3 pool concentration is <8 g/l, the pool is further concentrated to 8 g/L. After diafiltration (and concentration, if necessary), the pool is recirculated and recovered from the system using two times the system's holdup volume with 20 mM sodium phosphate, 50 mM sodium chloride, 1.5% (w/v) glycerol, pH 7.4. After recovery, a two-step dilution with diafiltration solution may be employed. The first dilution has a concentration target of 6 g/L and the second step has a concentration target of 5 g/L. Two steps may be used to reach the target. The second step may not be necessary if the concentration following the first dilution is within the targeted range.

Example 7

Intermediate Filtration and UF/DF 3

Prior to the PEGylation reaction, the cobalt-containing Arginase 1 can be stored long-term, including frozen long-term. The intermediate Co-Arginase can be filtered through a 0.2 µm filter and can be frozen for long term storage.

The UF/DF3 step uses membranes with a molecular weight cutoff of 30 kDa. One function of this step is to buffer exchange and concentrate the filtered UF/DF2 pool (fresh or thawed) to provide conditions optimal for PEGylation. If frozen Co-Arginase 1 intermediate is used as the starting material, thawing will be done at room temperature for up to 36 hours. The membranes are sanitized with cleaning solution (0.5 N NaOH) and rinsed with water. A normalized water permeability test (NWP) is performed followed by equilibration prior to use in production. Once the UF/DF system is equilibrated, the Co-Arginase 1 Intermediate is diafiltered against 0.1 M sodium phosphate, pH 8.4, for five diavolumes. After diafiltration, the pool is concentrated, recirculated, and recovered from the system using two times the system's hold-up volume with 0.1 M sodium phosphate, pH 8.4. After recovery, a two-step dilution with diafiltration solution is employed. The first dilution has a concentration target of 11 g/L and the second step has a concentration target of 10 g/L. Two steps are utilized to facilitate the target is levels. The second step may not be necessary if the concentration following the first dilution is within the targeted range.

Regarding the UF/DF 2 and UF/DF 3 steps, the first buffer exchange can be into 20 mM Sodium Phosphate, 50 mM NaCl, 1.5% Glycerol, pH 7.4, ≥5 DV, and protein concentrated to approximately 5.0 mg/mL. The second buffer exchange can be made into 0.1M sodium phosphate, pH 8.1-8.5, and protein concentrated to approximately 10.0 mg/mL (in preparation for PEGylation of the drug substance).

Example 8

PEGylation of Arginase 1

PEGylation covalently attaches PEG (polyethylene glycol) to the Co-Arginase 1 (drug substance) molecule (see Table 4 for a representative embodiment of the PEGylation step). In one embodiment, the PEGylation reaction covalently binds 5000 Da PEG molecules to Co-Arginase 1. In alternative embodiments, PEGylation can be performed prior to cobalt substitution of Arginase 1 or at other points in the production process. In one embodiment, the PEG conjugation reaction can use solid or liquid methoxy PEG succinimidyl carboxymethyl ester which reacts with sterically available lysines on Co-Arginase 1. The resulting PEGylated protein (Co-rhARG1-PEG) has a molecular weight of approximately 280 kDa. The PEGylated pool can be filtered and stored at 2-8° C. until UF/DF4 operations.

TABLE 4

PEGylation Process for Co-rhARG1 Drug Substance

| Step | Process Operation |
|------|-------------------|
| 1 | Thaw intermediate (if applicable) ↓ |
| 2 | Ultrafiltration/diafiltration ↓ |
| 3 | Add solid methoxy PEG succinimidyl carboxymethyl ester (MW 5000) and incubate for greater than 15 min pH 8.4 ↓ |
| 4 | Ultrafiltration/diafiltration ↓ |
| 5 | Filter the (Co-rhARG1-PEG) drug substance, fill in polycarbonate bottles, and freeze at ≤ −60° C. |

In one embodiment, solid methoxy PEG succinimidyl carboxymethyl ester (MW 5000) can be added to the Arginase 1 containing solution at a 19.3×molar excess and incubation 0.5-4.0 hours, pH 8.4.

Following PEGylation, ultrafiltration/diafiltration removes unbound PEG, exchanges the Arginase 1 into a formulation buffer and concentrates the Arginase 1 for the formulation step. This UF/DF4 step uses membranes with a molecular weight cutoff of 100 kDa. One function of this step is to buffer exchange the PEG pool into the final formulation while removing free PEG. Membranes used for this purpose are sanitized with cleaning solution (0.5 N NaOH) and rinsed with water. Once the UF/DF system is equilibrated, the PEG Pool is diafiltered against 5 mM potassium phosphate, 50 mM sodium chloride, 1.5% (w/v) glycerol, pH 7.4 for ten diavolumes. After diafiltration, the pool is recovered from the system with pressure. The recovered UF/DF4 Pool is diluted to 5 g/L with 5 mM potassium phosphate, 50 mM sodium chloride, 1.5% (w/v) glycerol, pH 7.4, prior to the final filtration and fill steps. IN an alternative embodiment, Arginase 1 is exchanged into 20 mM Sodium Phosphate, 50mM NaCl, 1.5% Glycerol, pH 7.4, and adjusted to a protein concentration of about 5.0 mg/mL.

In some embodiments, the formulation buffer 5 mM potassium phosphate, 50 mM sodium chloride, 1.5% glycerol, pH 7.4 was found to enhance the stability upon storage of Arginase 1 compared other buffers such as sodium phosphate buffer. In one or more embodiments, the buffer 5 mM potassium phosphate comprises 1 mM $K_2HPO_4$ and 4 mM $KH_2PO_4$.

Drug substance (Co-rhARG1-PEG) is a PEGylated cobalt-substituted human Arginase 1 made by conjugating activated PEG molecules with the &amino group of lysines and the amine group of N-terminal amino acid. A dye-based fluorescent assay is used to determine the molar ratio of PEG molecules per protein using ortho phthaldialdehyde. Ortho-phthaldialdehyde reacts in the presence of thiols, specifically with primary amines, to form fluorescent derivatives. Measurement of the fluorescent signal allows for the quantitation of reactive free amines present in a protein molecule. Quantitation is based on a standard curve using N-acetyl lysine. The number of PEGylated amines per protein can be determined by subtracting the number of free amines as measured by the fluorescent assay of the PEGylated drug substance from the theoretical number of free amines present in the unconjugated Co-Arginase 1. The theoretical number of free amines from lysine residues plus the N-terminal amino acid is 25. Free unconjugated PEG in the drug substance is measured by SEC-HPLC with detection by refractive index. Results can be expressed as μg/mL of free PEG (see Table 5).

TABLE 5

SEC-HPLC Method Parameters Free PEG Co-rhARG1-PEG Drug Substance

| Description | Method parameter |
|-------------|------------------|
| Column | TOSOH G3000PWxl, 7.8 × 300 mm, 7 μm column |
| Detector | Refractive Index Detector |
| Injection volume | 10 μl |
| Flow rate | 0.8 mL/min |
| Autosampler temperature | 5° C. |
| Column temperature | 20° C. |
| Mobile phase A | 1X PBS |
| Stop time | 20 minutes |

Example 9

CIEX-HPLC Characterization of Drug Intermediate

During *E. coli* fermentation, various Arginase 1 charge variants may be produced. Charge variants can be analyzed by a cation exchange HPLC (CIEX-HPLC) method using a TSK gel cation exchange column. This type of analysis uses a mobile phase (A) of 20 mM MES, pH 6.0 and a mobile phase B of 20 mM MES, 500 mM NaCl pH 6.0; flow rate of 1.0 mL/minutes; run time of 40.0 minutes; column temperature of 22° C.; and mobile phase gradient according to Table 6.

TABLE 6

CIEX-HPLC Charge Variants Co-Arginase 1 Intermediate Gradient Program

| Minutes | % Mobile Phase B |
|---------|------------------|
| 0.00 | 0 |
| 1.95 | 0 |
| 17.00 | 30 |
| 23.00 | 60 |
| 25.00 | 100 |
| 30.00 | 100 |
| 30.10 | 0 |
| 40.00 | 0 |

Figure 5:
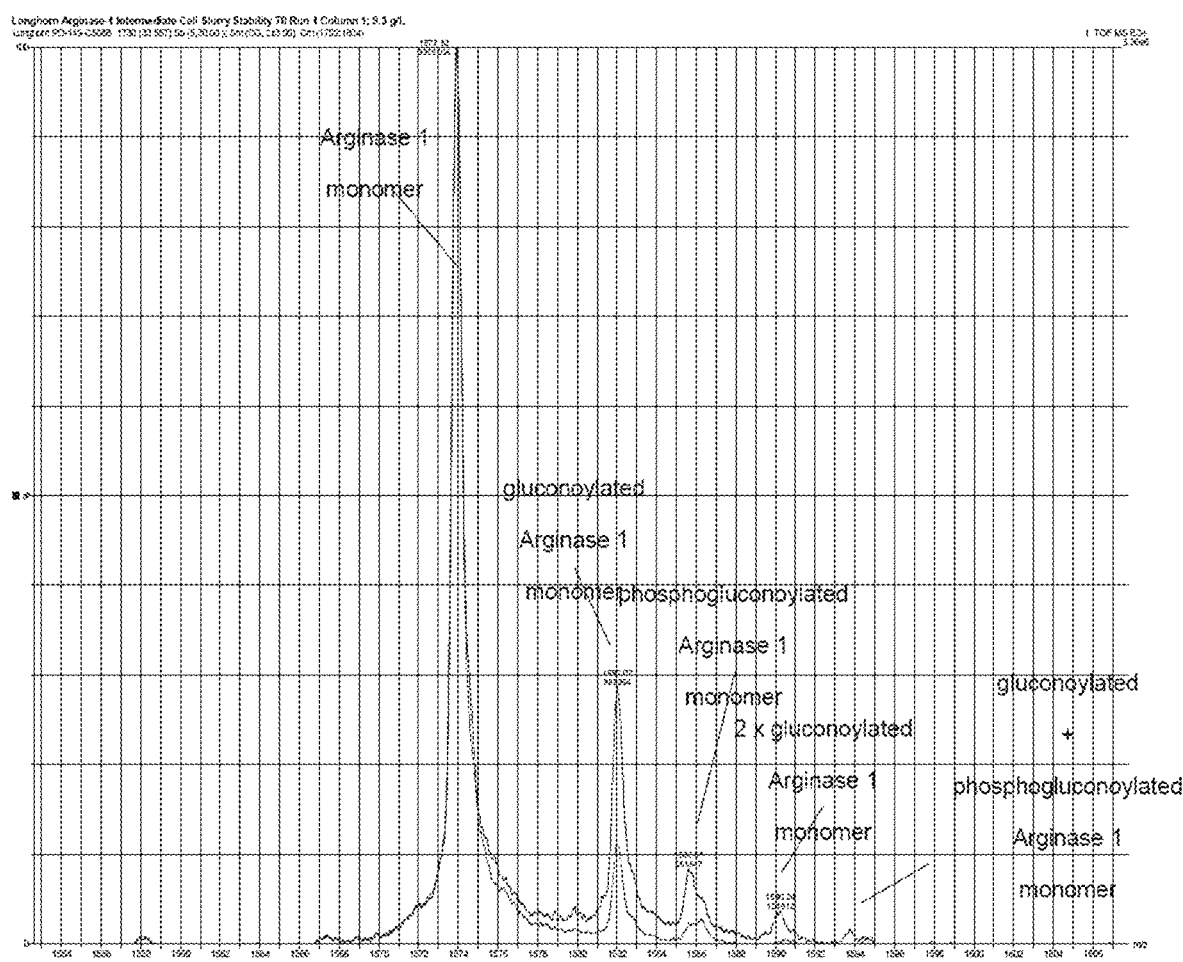
FIGS. 5(a)-5(d) show the results of an analytical cation exchange HPLC method used to determine the charge heterogeneity profile of the Co-Arginase 1 intermediate sample eluted from Column 1 (also called First Protein Product). A 1 mg/ml sample of Arginase 1 was loaded onto a cation exchange column with a mobile phase of 20 mM MES, pH 6.0 buffer, with a flow rate of 1.0 mL/minute. A gradient of 0-500 mM NaCl was introduced over 40 minutes and the amount of protein eluted from this column was estimated by absorbance at 280 nm.

Samples are diluted with formulation buffer prior to analysis. The results are described as percent charge variant distribution. A representative chromatogram is shown in FIG. 5(*a*) where six predominant peaks are typically observed for Co Arginase 1 intermediate.

Example 10 iCIEF Characterization of Drug Substance

The drug intermediate is PEGylated to form the drug substance. PEGylation of the drug intermediate renders the use of the drug intermediate CIEX-HPLC method less suitable than other embodiments developed as part of this invention. An anion IEX-HPLC was evaluated but did not give an adequate separation. Alternatively, an imaging capillary isoelectric focusing (iCIEF) method was developed to analyze charge variants of the drug substance.

Analytes in imaging capillary isoelectric focusing (iCIEF) migrate through a capillary by the counter-migration of hydronium ions (anolyte), and hydroxyl ions (catholyte) in the presence of an applied electric field. The sample is diluted in a matrix containing carrier ampholytes and pI markers. Separation of proteins occurs in two focusing steps. An initial prefocusing step establishes the pH gradient. Charge variants are more sharply focused and separated during a second higher voltage focusing step. An image of UV light absorption of the entire capillary is digitally captured every 30 seconds and after completion of the focusing steps.

The results can be expressed as percent charge variant distribution. A representative electopherogram is shown in FIG. 5(b) where nine predominant peaks are observed for drug substance. Peaks 3 and 4 are integrated together because the resolution between those peaks has been shown to be variable. The relative areas of these peaks are provided in Table 7:

TABLE 7 iCIEF Characterization of Charge Variants of Co-rhARG1-PEG

|    | Name      | pI    | Area   | % Area |
|----|-----------|-------|--------|--------|
| 1  | Marker    | 4.220 |        |        |
| 2  | Peak 1    | 6.111 | 130195 | 12     |
| 3  | Peak 2    | 6.268 | 245568 | 22     |
| 6  | Peak 3 + 4| 6.360 | 255343 | 23     |
| 7  | Peak 5    | 6.501 | 226011 | 20     |
| 8  | Peak 6    | 6.604 | 156066 | 14     |
| 9  | Peak 7    | 6.708 | 71805  | 6      |
| 10 | Peak 8    | 6.794 | 27780  | 2      |
| 11 | Peak 9    | 6.866 | 8847   | 1      |
| 12 | Marker    | 7.650 |        |        |

Example 11

Enzyme Activity of Co-Arginase 1 Intermediate and Drug Substance

The enzymatic assay used to measure activity and to establish identity of Co-Arginase 1 intermediate and Co-rhARG1-PEG drug substance monitors the conversion of arginine to ornithine. The reaction mixtures have one enzyme concentration tested at seven different arginine substrate concentrations over a range of 0-2 mM. The reactions are conducted for a fixed time at 37° C. The reaction time has been established to ensure that there is less than 10% consumption of substrate at any given substrate concentration. The reaction is quenched and the product, ornithine, is derivatized and quantified by reverse phase-UPLC.

Figure 8A:
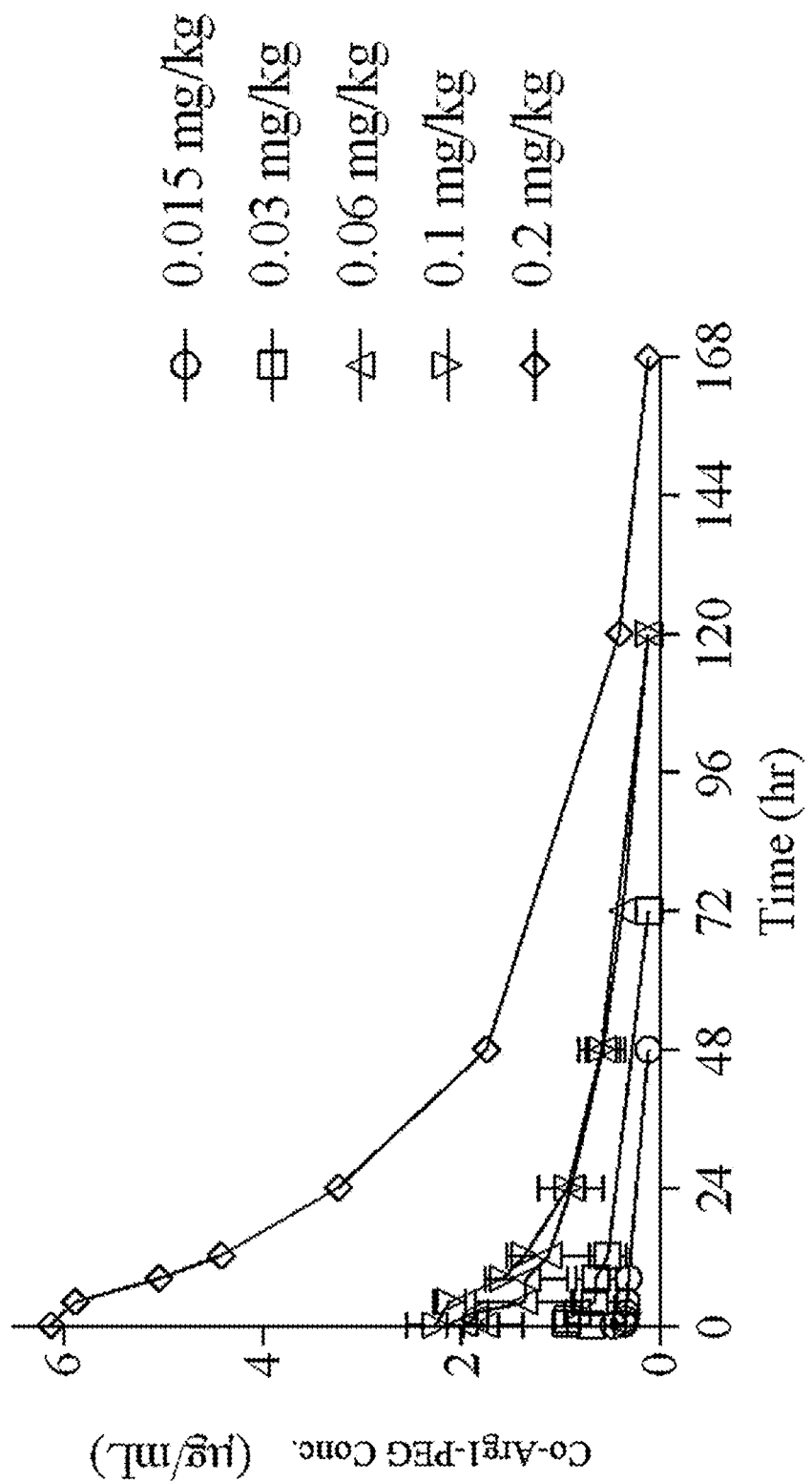
FIGS. 8(a)-8(b) show the enzyme activity of Co-Arginase 1 intermediate and Co-rhARG1-PEG drug substance.
Figure 8B:
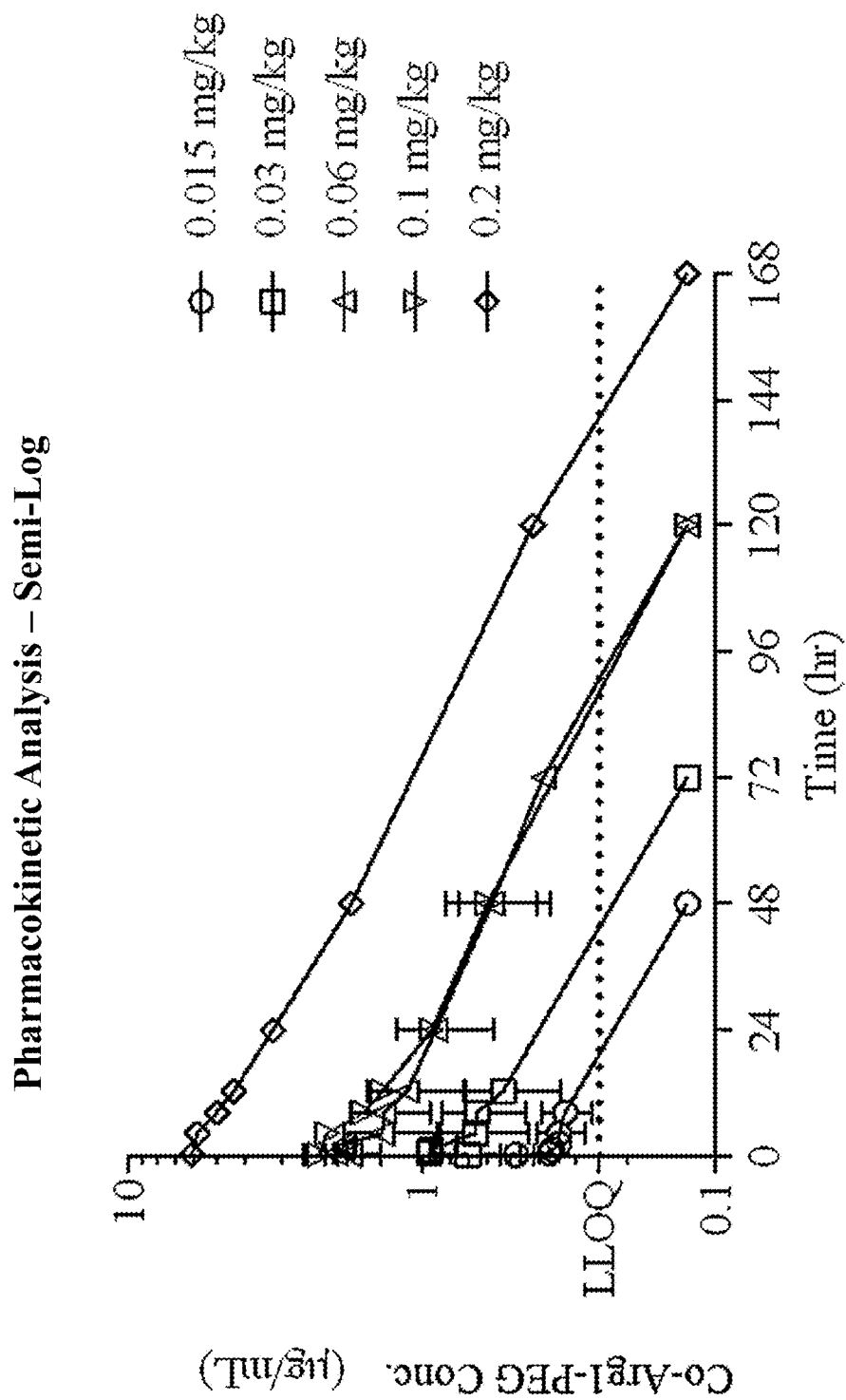
Figure 8C:
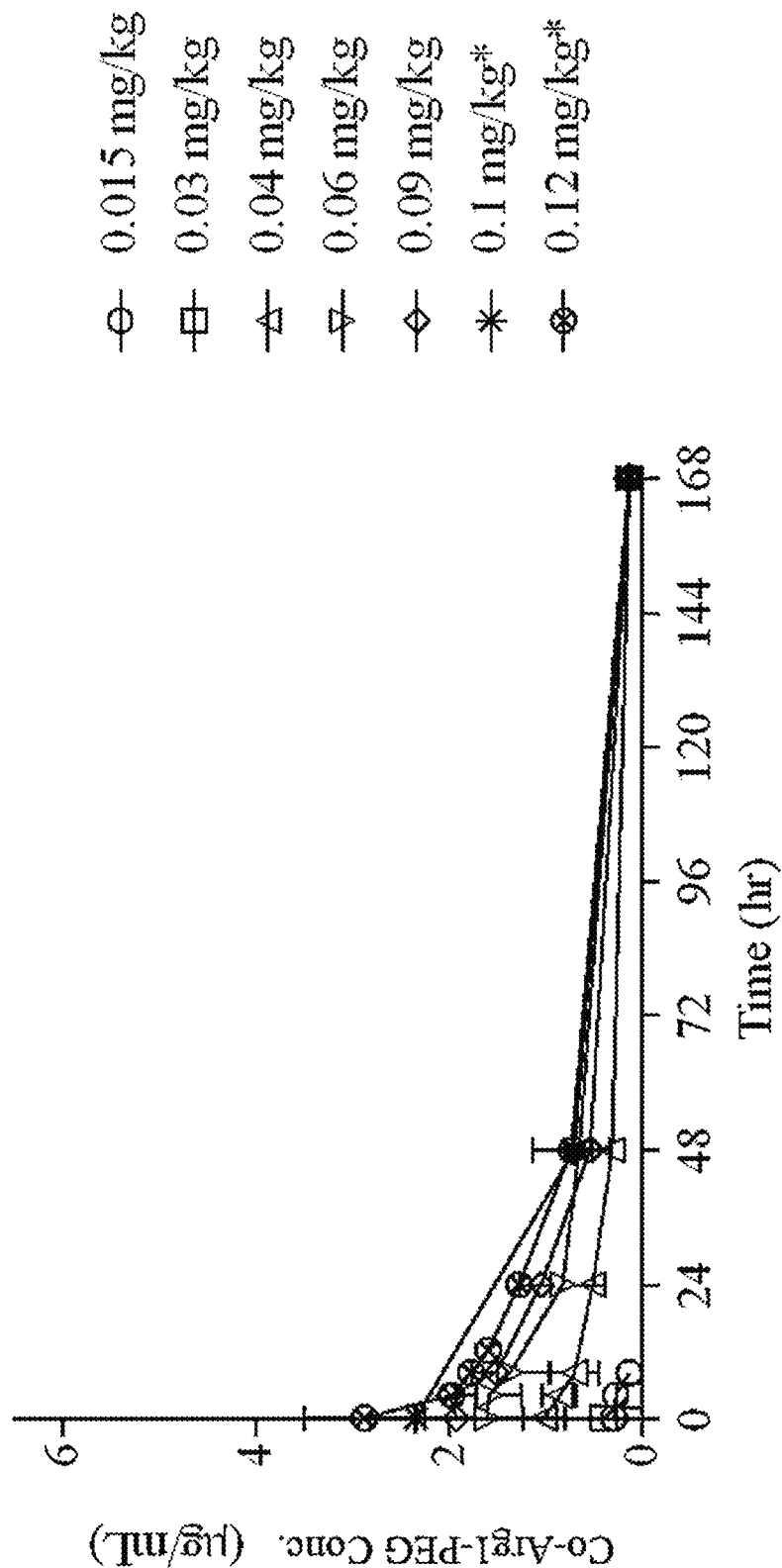
Figure 8D:
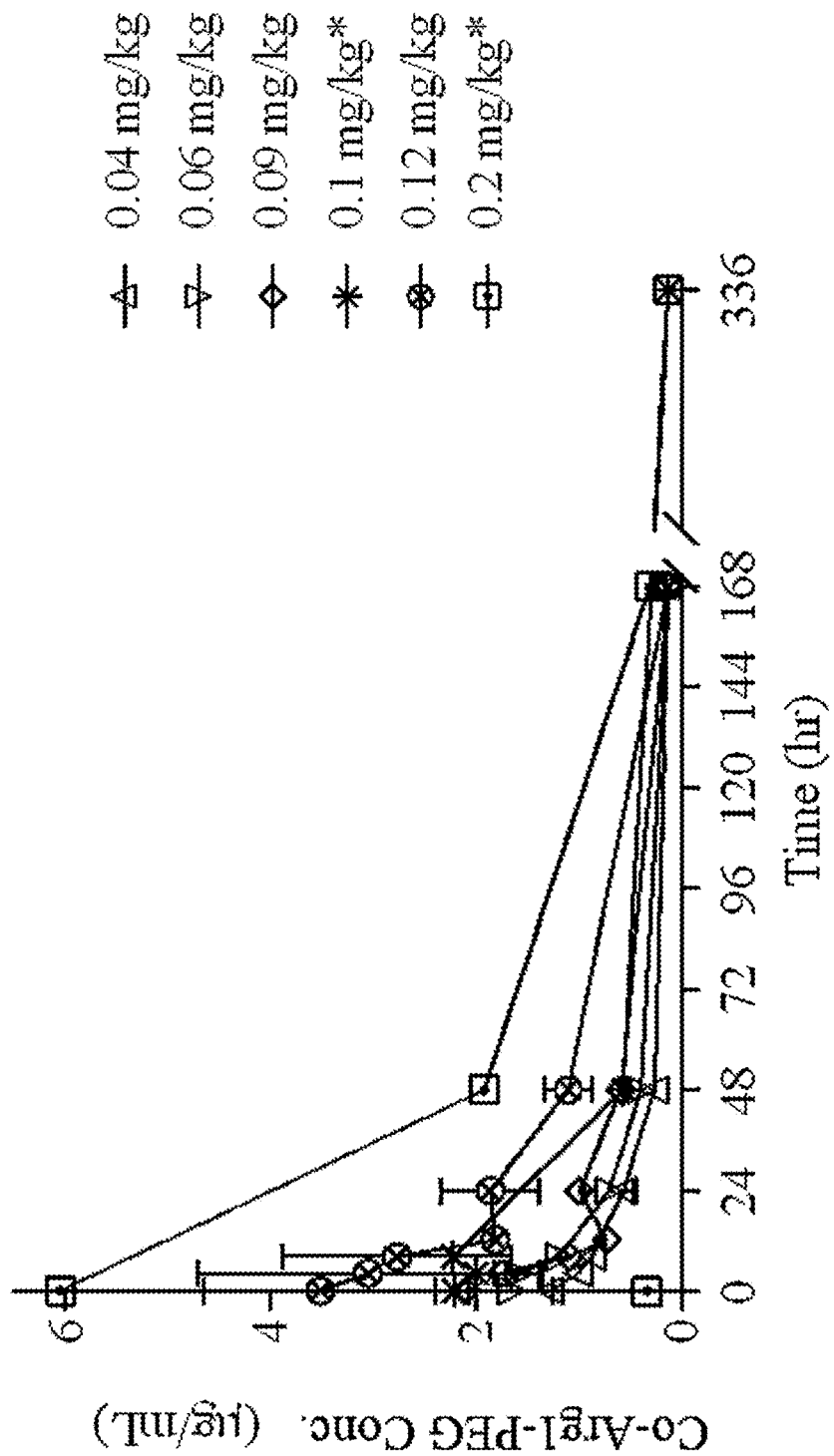
Figure 8E:
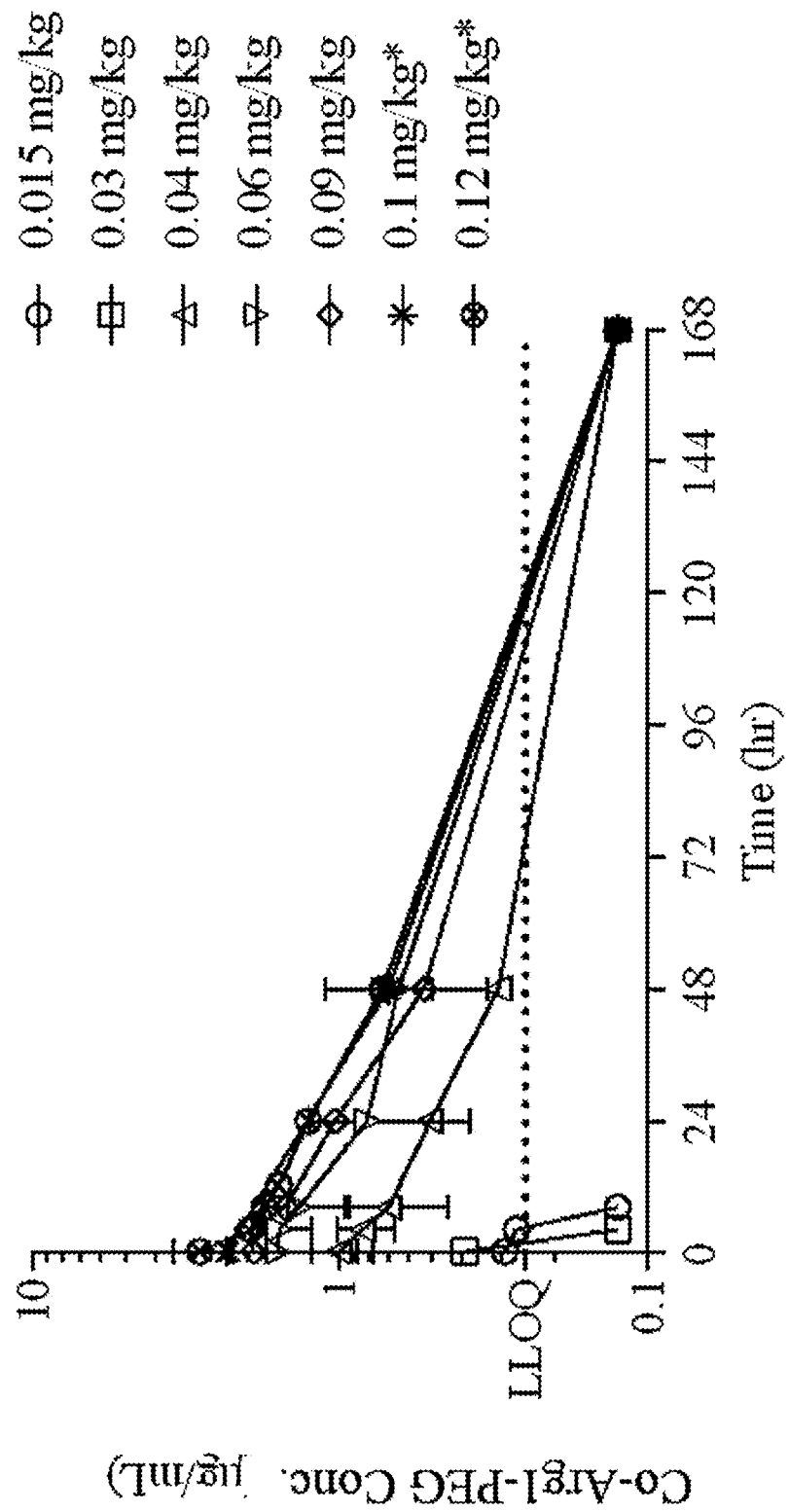
Figure 8F:
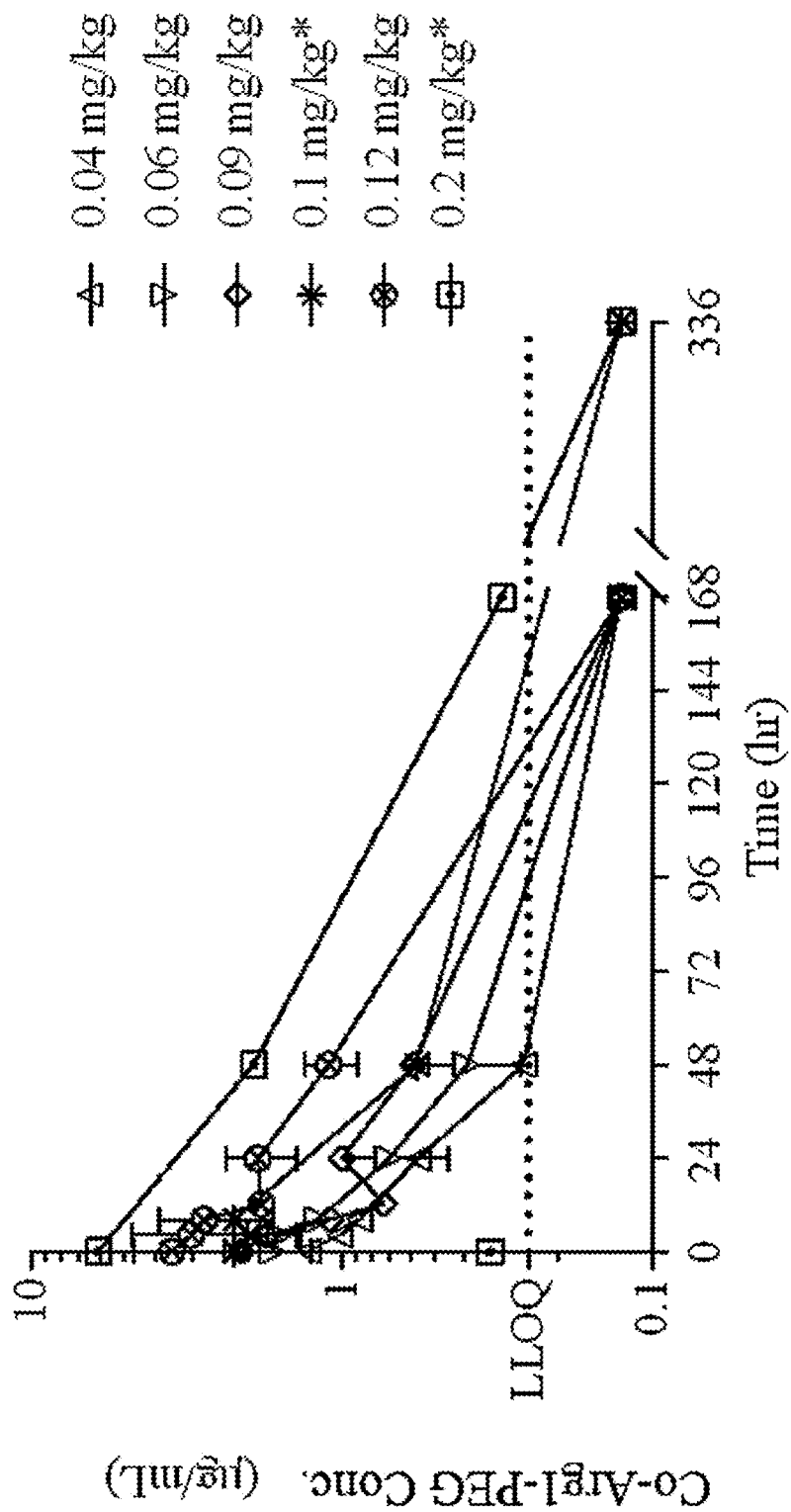

Examples of plots of reaction velocity vs substrate concentration are shown in FIG. 8(a) (Co-Arginase 1 Intermediate) and FIG. 8(b) (Co-rhARG1-PEG drug substance) along with representative $K_{cat}$, $K_m$, and $K_{cat}/K_m$ values.

Example 12

Analysis of Cobalt and Manganese

Cobalt, residual manganese, and free cobalt were measured using inductively coupled plasma mass spectrometry (ICP-MS). Samples were digested by microwaving and using 1% nitric acid and 6% hydrogen peroxide to release all the metals from the matrix. The resulting digestion was analyzed by ICP-MS. Cobalt and residual manganese samples were digested without any sample treatment. Free cobalt was measured on permeate samples that have been ultrafiltered to separate the enzyme from the permeate to measure cobalt that is not associated with the enzyme. Table 8 summarizes some of the characteristics of Co-Arginase 1 Intermediate.

TABLE 8

Typical Co-Arginase 1 Intermediate Characteristics

| Test | Purpose | Analytical Principle | Typical Values |
|------|---------|---------------------|----------------|
| CIEX HPLC | Charge | HPLC | Peak 1: 0-4% |
|  |  |  | Peak 2: 2-8% |
|  |  |  | Peak 3: 10-20% |
|  |  |  | Peak 4: 16-30% |
|  |  |  | Peak 5: 40-52% |
|  |  |  | Peak 6: 4-15% |
| SDS-PAGE (reduced) | Purity | Charge mobility | ≥95% |
| $K_m$ | Activity | HPLC | 0.15-0.24 mM |
| $k_{cat}$ |  |  | 200-380/sec |
| Specific activity | Activity | HPLC | 320-600 U/mg |
| Cobalt | Activity | ICP-MS | 7-13 µg/mL |
| Free cobalt | Stability | ICP-MS | ≤0.05 µg/mL |
| Residual manganese | Impurity, activity | ICP-MS | ≤1 µg/mL |
| pH | Acidity | pH | 7.0-7.8 |

TABLE 9

Typical Co-rhARG1-PEG Drug Substance Characteristics

| Test | Purpose | Analytical Principle | Typical Values |
|------|---------|---------------------|----------------|
| Charge heterogeneity | Quality | Imaging capillary isoelectric focusing (iCIEF) | Peak 1: <20% |
|  |  |  | Peak 2: <30% |
|  |  |  | Peaks 3 and 4: 10-30% |
|  |  |  | Peak 5: 15-30% |
|  |  |  | Peak 6: 10-25% |
|  |  |  | Peak 7: <25% |
|  |  |  | Peak 8: <15% |
|  |  |  | Peak 9: <8% |
| $K_m$ | Activity | HPLC | 0.15-0.24 mM |
| $k_{cat}$ |  |  | 200-380/sec |
| Specific activity | Activity | HPLC | 320-600 U/mg |
| Total Cobalt | Activity | ICP-MS | 7-13 µg/mL |
| Residual Manganese | Activity | ICP-MS | <1 µg/mL |
| Free Cobalt | Stability | ICP-MS | ≤0.05 µg/mL |
| PEG: Protein Molar Ratio | PEGylation | HPLC | 8-16 moles/mole |
| Free PEG | Impurities | HPLC | <500 µg/mL |
| pH* | Acidity | pH | 7.0-7.8 |

Example 13

Co-Arginase 1 Intermediate Post-Translational Modifications

Co-Arginase 1 intermediate post-translational modifications were detected using a variety of techniques such as peptide mapping, LC-MS intact mass spectrometry, and reverse phase LC/MS. The summary of all identified modifications is listed in Table 10.

TABLE 10

Identified Modifications of Co-Arginase 1 Intermediate

| Modification | Method of Detection |
|---|---|
| N-terminal gluconoylation/ Gluconoylation | Peptide mapping (Glu-C digestion) RP-HPLC-MS/MS and LC-MS RP-UPLC/MS |
| Phosphogluconoylation | RP-UPLC/MS |
| Di-Gluconoylation | RP-UPLC/MS |
| N-terminal methionine-truncation | Peptide mapping (Glu-C digestion) RP-HPLC-MS/MS and LC-MS |
| Acetylation | Peptide mapping (Glu-C digestion) RP-HPLC-MS/MS and LC-MS |
| N-deamidation/ succinimide formation | Peptide mapping (Glu-C digestion) RP-HPLC-MS/MS and LC-MS |

Characterization determined that when Co-Arginase 1 intermediate modification was present, the predominant modification was N-terminal gluconoylation (confirmed by peptide mapping). Additional characterization of Arginase 1 modified species was performed by testing samples taken at three time points (fermentation, post-Column 1, and on drug intermediate from Column 3). The analytical methods typically require Arginase to be dissociated and analyzed as a monomer. Arginase 1 N-terminal gluconoylated (analyzed as a monomer) was typically 10.8 to 13.9%. Other modifications were N-terminal phosphogluconoylated monomer (4.3 to 6.5%), and di-gluconoylated monomer (0.7 to 1.2%), across the three timepoint samples. In a sample used from a standardized reference production run, the levels of un-modified Co-Arginase 1 (monomer) and Co-Arginase 1 intermediate were comparable at 80.6% to 83.6%, respectively. The standard condition used for the purification process (i.e. no salt gradient applied to Column 1) moderately altered the relative level of un-modified monomer carried through to Co-Aminase 1 intermediate (81.1 to 83.6%).

TABLE 11

Co-Arginase 1 Characterization LC/MS Results

| Sample ID | Arginase 1 Monomer (Unmodified) (%) | Gluconoylated Arginase 1 Monomer (%) | Phosphogluconoylated Arginase 1 Monomer (%) | Di-Gluconoylated Arginase 1 Monomer (%) |
|---|---|---|---|---|
| Standardized Reference | 80.6 | 13.9 | 4.3 | 1.1 |
| Fermentation | 81.1 | 12.4 | 6.5 | 1.2 |
| Post-Column | 81.4 | 12.2 | 5.4 | 0.9 |
| Drug Substance | 83.6 | 10.8 | 4.9 | 0.7 |

Example 14

Variation of Column 1 Conditions

Figure 7A:
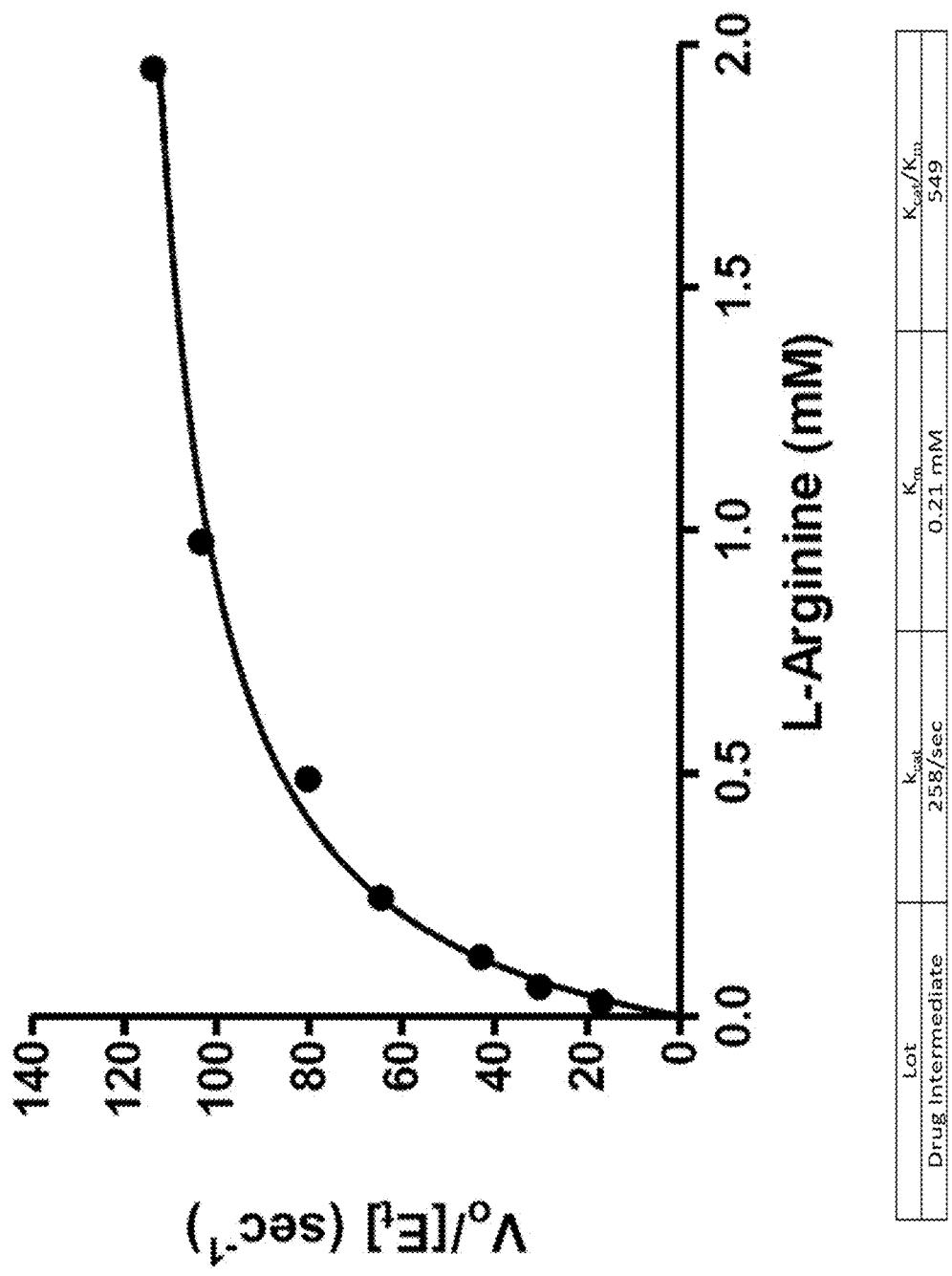
FIG. 7 show the results of a gradient of 0.0-0.2 M NaCl applied to Column 1. Fractions were collected every 0.25 CV (Column Volume) through the gradient. The data represent two column 1 runs using two different lots of harvested cell slurry as feed material. The load factor used for the evaluations was 30 g/L. The gradient successfully separated different gluconoylated species while maintaining product recovery.
Figure 7B:
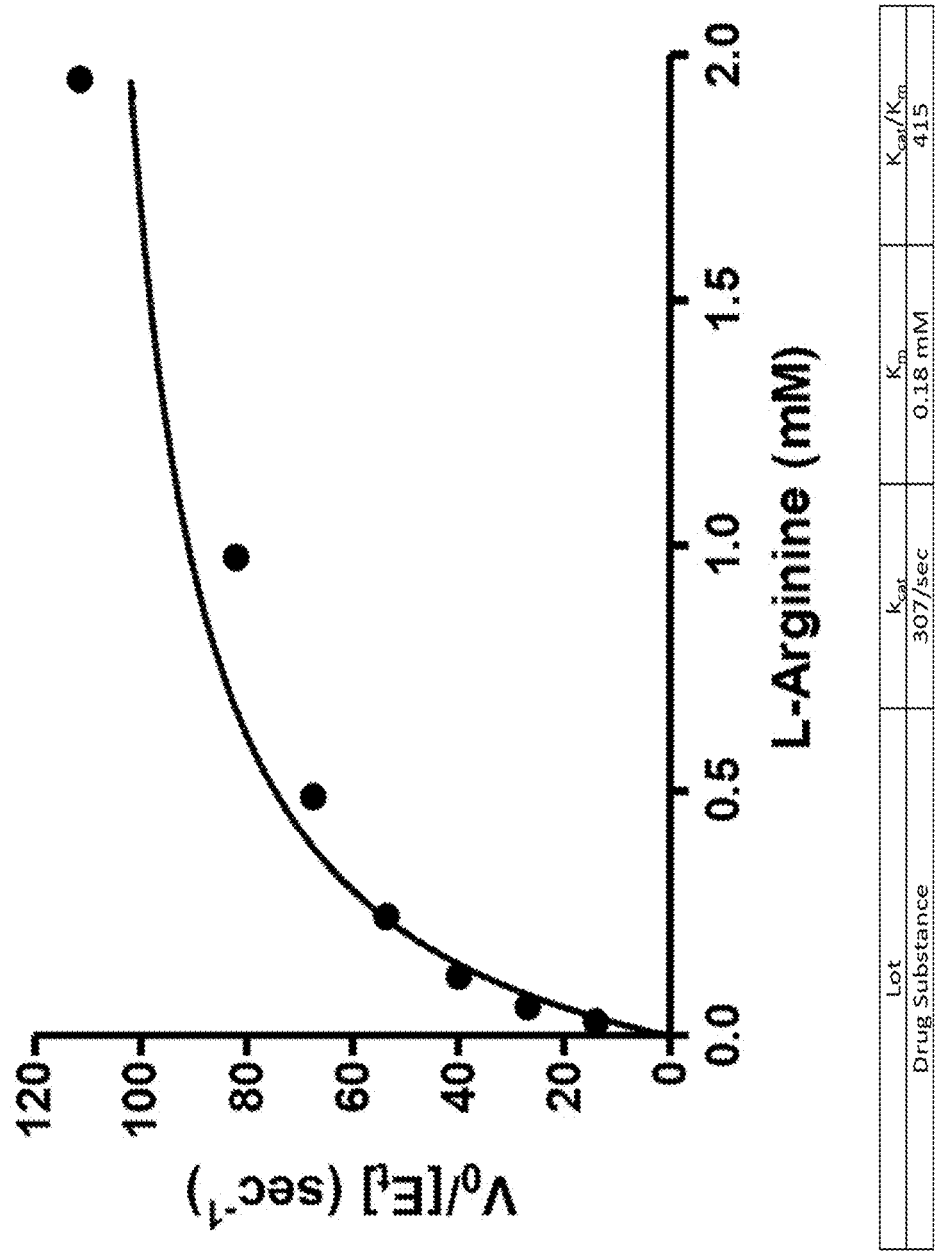

In alternative embodiments, a NaCl gradient can be applied to Column 1. Using a NaCl gradient over Column 1 enables separation of different Arginase 1 variants to select for preferred embodiments. FIG. 7 shows a gradient from 0.0-0.2 M NaCl applied to Column 1. Individual fractions collected from the Column 1 elution were assayed by SE-HPLC, CEX-HPLC, and RP-HPLC.

An analytical CEX-HPLC method was used that assigns Arginase 1 charge variants Peak Numbers of 1 through 6 (see FIG. 5(c)). The Peak Numbers align with the various gluconoylation states as well as un-gluconoylated Arginase 1. This analysis showed six peaks in the Arginase 1 eluted from the NaCl gradient. Arginase 1 variants assigned Peak Numbers 1, 2, and 3 eluted early in the Column 1 elution peak. Peak 4 eluted through the highest concentration portion of the eluted Arginase 1 and peak 5 (unmodified Arginase 1) and peak 6 eluted later in the elution peak. Thus, the 0.0-0.2 M NaCl successfully separated different charge variants of Arginase 1.

Alternative NaCl gradients can be used for Column 1 elution such as 0-0.5 M NaCl. The use of a NaCl gradients was found to reproducibly separate Arginase 1 into six distinct peaks enabling selection of specific Arginase 1 variants for further processing in the manufacture of drug substance or drug product.

Figure 6:
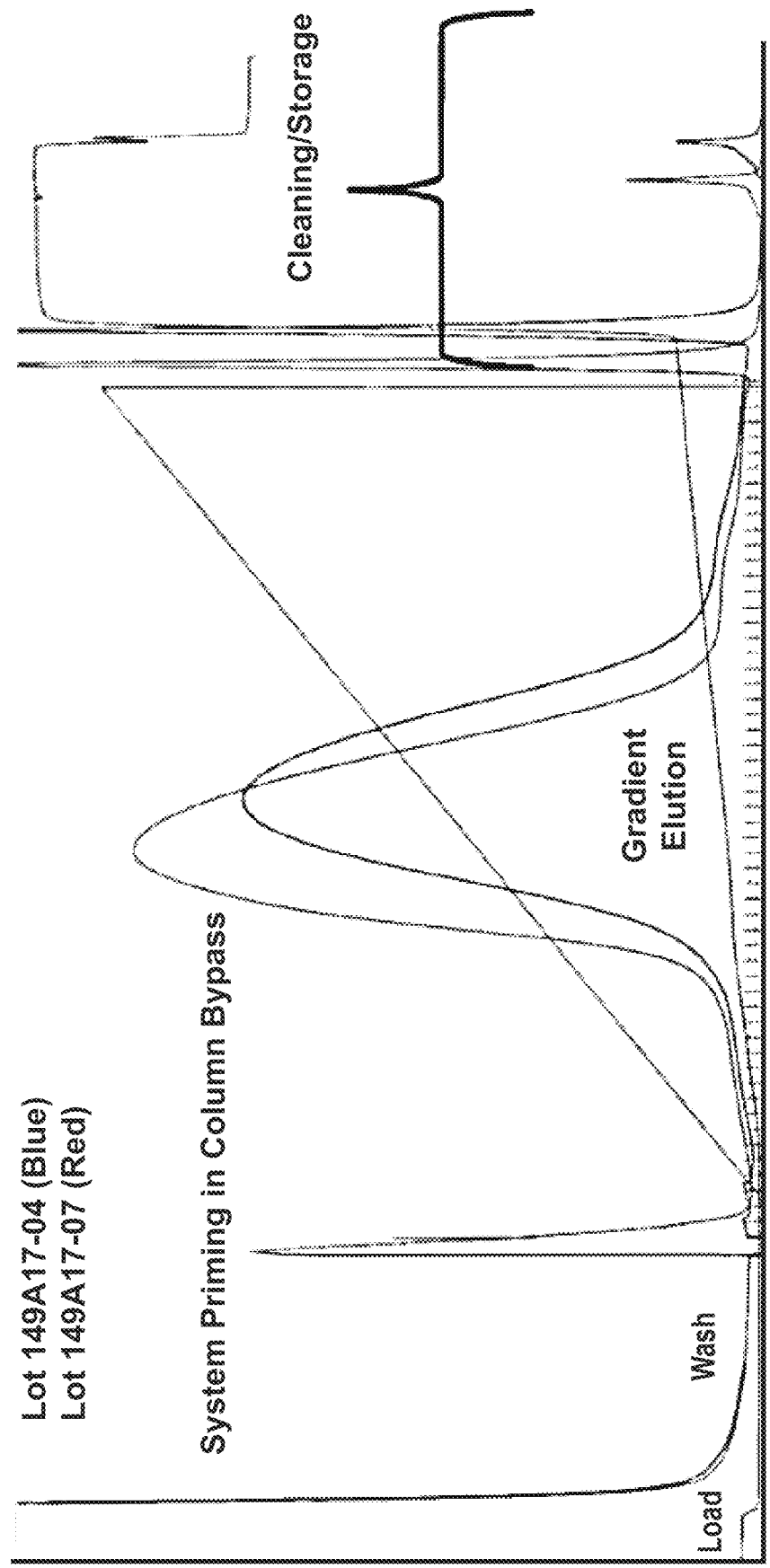
FIG. 6 shows the results of a LC/MS method to determine Arginase 1 gluconylation variants produced by expression of rhARG in E. coli. The LC/MS analysis identifies unmodified Arginase 1 (monomer), gluconylated Arginase 1, phosphogluconylated Arginase 1, and 2 times (2×) gluconylated Arginase 1. The trace is from two separate production runs of drug intermediate. The overlay of mass spectra was summed over 33-35 minutes on a RP LCMS at 35° C.; Spectra are normalized to the peak intensities of the signals due to unmodified Arginase 1. Peak intensities of variants are proportional to relative abundance.

Further analysis of the first protein product (and the Arginase 1 variants) was also analyzed by LC/MS (see FIG. 6). The LC/MS analysis identifies specific types of gluconylation generated by production of Arginase 1 in E. coli. The LC/MS analysis identifies unmodified Arginase 1, gluconylated Arginase 1, phosphogluconylated Arginase 1, and 2 times (2x) gluconylated Arginase 1.

Table 12 shows that the application of a 0-0.2 M NaCl gradient (and the corresponding fractionated CEX Peaks 1-6) produces fractions that have differing levels of gluconylation. Each of Peak Numbers 1-6 were analyzed by LC/MS. The data show that the dominant peak (Peak 5) has a high percentage of non-gluconylated Arginase 1 as well as high specific activity. Depending upon the desired characteristics different fractions (corresponding to Peaks 1-6) can be collected for further processing.

TABLE 12

LC/MS analysis of drug intermediate Peaks 1-6.

| Fraction | Concentration (mg/mL) | % Non-Gluconylated Arginase 1 Monomer Mass by MS | Specific Activity (U/mg) |
|---|---|---|---|
| Peak Number 1 | 0.2 | 28.4 | 118 |
| Peak Number 2 | 0.9 | 37.8 | 286 |
| Peak Number 3 | 3.4 | 56.2 | 298 |
| Peak Number 4 | 6.5 | 68.2 | 349 |
| Peak Number 5 | 12.0 | 96.6 | 329 |
| Peak Number 6 | 2.2 | 97.1 | 198 |

In addition to varying NaCl concentrations on Column 1, different amounts of protein can be loaded on Column 1 to enhance purification of non-gluconylated Arginase 1 species.

Varying the load factor of Column 1 and using a NaCl gradient over Column 1 can compensate for unexpected perturbations experienced during *E. coli* fermentation that produce gluconylated Arginase 1 species.

Example 15

Variation in Fermentation Conditions

Experiments were performed to determine the robustness of fermentation conditions for production of Arginase 1. Table 13 shows that fermentation of *E. coli* at the at sub-optimal pH of 7.6 produces more gluconylation that at the preferred pH 7.2 fermentation. Vessels B 1, B8, and B12 used optimal conditions of fermentation: pH 7.2, Dissolved Oxygen 30%, feed rate of media 0.06 mL/min. Vessel B3 was used to ferment Arginase 1 expressing *E. coli* at pH 7.6 (a pH that is higher than optimal conditions). The increase in pH resulted in a higher proportion of phospho-gluconylated adducts (23% vs 10-12% in control runs)

TABLE 13

Gluconylated Arginase 1 Observed in Fermentation Vessels

| Vessel | Native Arg 1 | Gluconylated | Phosphogluconylated | 2X Gluconylated | Gluconylated and Phosphogluconylated |
|---|---|---|---|---|---|
| B1 | 88.5 | 6.2 | 5.3 | — | — |
| B8 | 89.2 | 6.3 | 4.6 | — | — |
| B12 | 89.0 | 5.9 | 5.1 | — | — |
| Average | 88.9 | 6.1 | 5.0 | — | — |
| B3 | 76.7 | 15.0 | 5.8 | 1.8 | 0.6 |

Example 16

Variation of Load Factor on Column 1

Different amounts of *E. coli* cell lysate were applied to Column 1 to determine the effect on purification of Arginase 1 charge variants, as well as yield and purity. Load factors of 15-60 g protein/L resin were used under various conditions showing a shift in the CIEX charge species profiles (Table 14). Higher load factors resulted in better separation of gluconylated variants (but depending on which fractions were collected a trade-off in yield may result). For example, with a load factor of 20 mg protein/mL resin peak 5 was 45.8% whereas with a load factor of 40 mg/mL this increased to 50.0%.

TABLE 14

Effect of Column 1 Load Factor on Protein Product 1

| Sample | Peak | Area (%) | Step Yield (%) |
|---|---|---|---|
| 40 mg/mL LF | 1 | 1.2 | 95.1 |
| | 2 | 1.6 | |
| | 3 | 11.6 | |
| | 4 | 21.2 | |
| | 5 | 50.0 | |
| | 6 | 15.5 | |

TABLE 14-continued

Effect of Column 1 Load Factor on Protein Product 1

| Sample | Peak | Area (%) | Step Yield (%) |
|---|---|---|---|
| 30 mg/mL LF | 1 | 1.1 | 101.0 |
| | 2 | 4.1 | |
| | 3 | 14.0 | |
| | 4 | 21.1 | |
| | 5 | 46.2 | |
| | 6 | 13.5 | |
| 20 mg/mL LF | 1 | 1.6 | 93.2 |
| | 2 | 4.5 | |
| | 3 | 14.3 | |
| | 4 | 20.9 | |
| | 5 | 45.8 | |
| | 6 | 12.8 | |

Example 17

Phase 1/2 Clinical Investigation

The drug product produced by the methods of this invention was used in a Phase 1/2, open-label study to evaluate administration of Co-rhARG1-PEG in Arginase 1 deficiency and hyperargininemia. The primary endpoint of this study was to evaluate the safety and tolerability of intravenous (IV) administration of Co-rhARG1-PEG in subjects with hyperargininemia/Arginase 1 deficiency. The secondary endpoints were: to determine the effects of study drug administered IV on plasma arginine concentrations; to determine the effects of study drug administered IV on plasma guanidino compounds (GCs); and to characterize the pharmacokinetic (PK) profile of study drug administered IV. Other endpoints include evaluation of clinical outcome assessments in capturing clinical benefit such as: 6-Minute Walk Test (6MWT), Gross Motor Function Measure (GMFM) Parts D and E, and Adaptive Behaviour Assessment System (ABAS).

The Phase 1/2 data demonstrated that Co-rhARG1-PEG was highly effective in sustainably lowering plasma arginine. In addition, the control of plasma arginine levels in patients was accompanied by clinically meaningful responses in mobility and adaptive behavior. The treatment was generally well tolerated. Hypersensitivity reactions were infrequent and manageable with standard measures.

The Co-rhARG1-PEG drug product supplied for the study was as a liquid formulation in 10 mL single-use glass vials containing 5 mL of formulated drug product at a concentration of 1 mg/mL. The drug was formulated in 50 mM NaCl, 1 mM $K_2HPO_4$, 4 mM $KH_2PO_4$, and 1.5% w/v glycerol.

Figure 16:
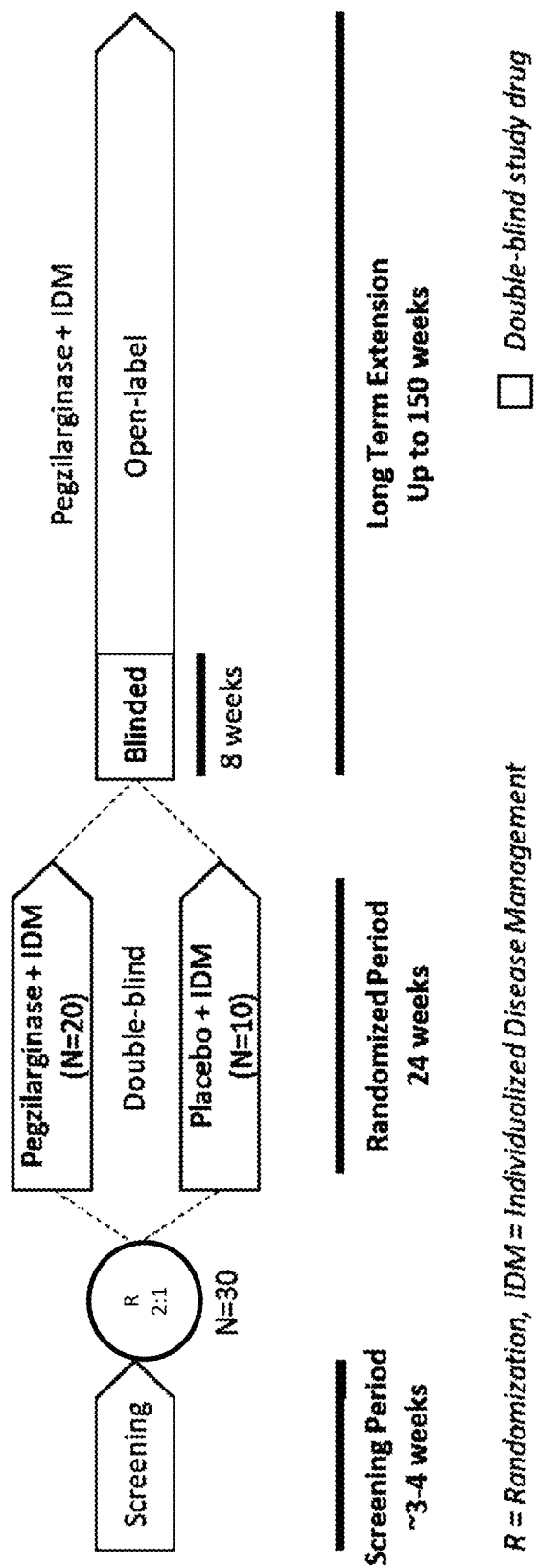
FIG. 16 shows a Phase 1/2 study that was conducted in two parts: Part 1 (Single Ascending Dose Escalation) and Part 2 (Repeated Dosing). The scheme shows the Phase 1/2 trial (101A) and open label extension (102A).

The Phase 1/2 study was conducted in two parts: Part 1 (Single Ascending Dose Escalation) and Part 2 (Repeated Dosing). The study design for this phase 1/2 trial 101A and the 102A open label extension is shown in FIG. 16.

Part 1 introduced the patient to the drug and was focused upon safety. Part 2 was designed to settle the patient on a consistent dose and look for markers of clinical effectiveness. Each part was preceded by a baseline assessment of arginine levels. All patients who participated in Part 1 could continue Arginase 1 dosing in Part 2 if they qualified for continued dosing.

In the study, each patient received a starting dose that could escalate in Part 1 with a 2-week washout/observation period between each successive dose level. The possible doses for each patient in Part 1 were 0.015, 0.03, 0.06, 0.10, 0.15, 0.20, and 0.30 mg/kg, at 2-week intervals as needed to optimize plasma arginine. Any particular dose can be repeated, or a dose increased/decreased between the specified dose levels if emerging data from prior dose levels met certain criteria. For example, the escalation of dose may cease if one or more of the following dose escalation stopping criteria were met: the patient's plasma arginine level was <40 µM for at least 40 (±2) consecutive hours post-dosing for all samples collected during that time period or the patient's plasma arginine level averaged <115 µM for at least 112 (±2) consecutive hours post-dosing for all samples collected during that time period.

If none of these events occurred, the patient could be escalated to the next higher dose level of Arginase 1 every 2 weeks until any dose escalation stopping criterion was reached or the patient had received the highest dose under this protocol of 0.30 mg/kg. Ultimately, for treatment purposes, it is also possible that the dosing might increase over 0.30 mg/kg.

Part 2 was a repeat-dosing period for patients who completed Part 1. Part 2 found a dose and regimen for each patient that safely optimized plasma arginine in the range of about 40 µM to about 115 µM during repeat-dose administration, with emphasis on maintaining pre-dose levels below 150-200 µM. Several dose levels could have been used in Part 2 if the data indicated a potential to better investigate a dose-response outcome during repeat-dose administration. On-treatment arginine levels were also compared with arginine levels determined prior to treatment.

Patients who completed Part 2 of 101A were eligible to participate in a long-term open-label extension (OLE) trial (NCT03378531). Treatment with 24 weekly IV doses with the option to switch to subcutaneous dosing for the remainder of the 3-year OLE period.

Results

Increases in mean $C_{max}$ and mean $AUC_{0-168}$ appeared dose proportional in all patients. Mean (±SD) $C_{max}$ was 0.428±0.0915, 0.723±0.247, 1.73±0.538, 2.27±0.238, and 6.13 (N=1) µg/mL for Co-rhARG1-PEG dose levels of 0.015, 0.03, 0.06, 0.1 and 0.2 mg/kg, respectively. There was a slight anti-drug antibody (ADA) impact on mean $C_{max}$ in ADA positive vs. ADA negative patients (FIGS. 9(a)-9(f)).

Figure 9A:
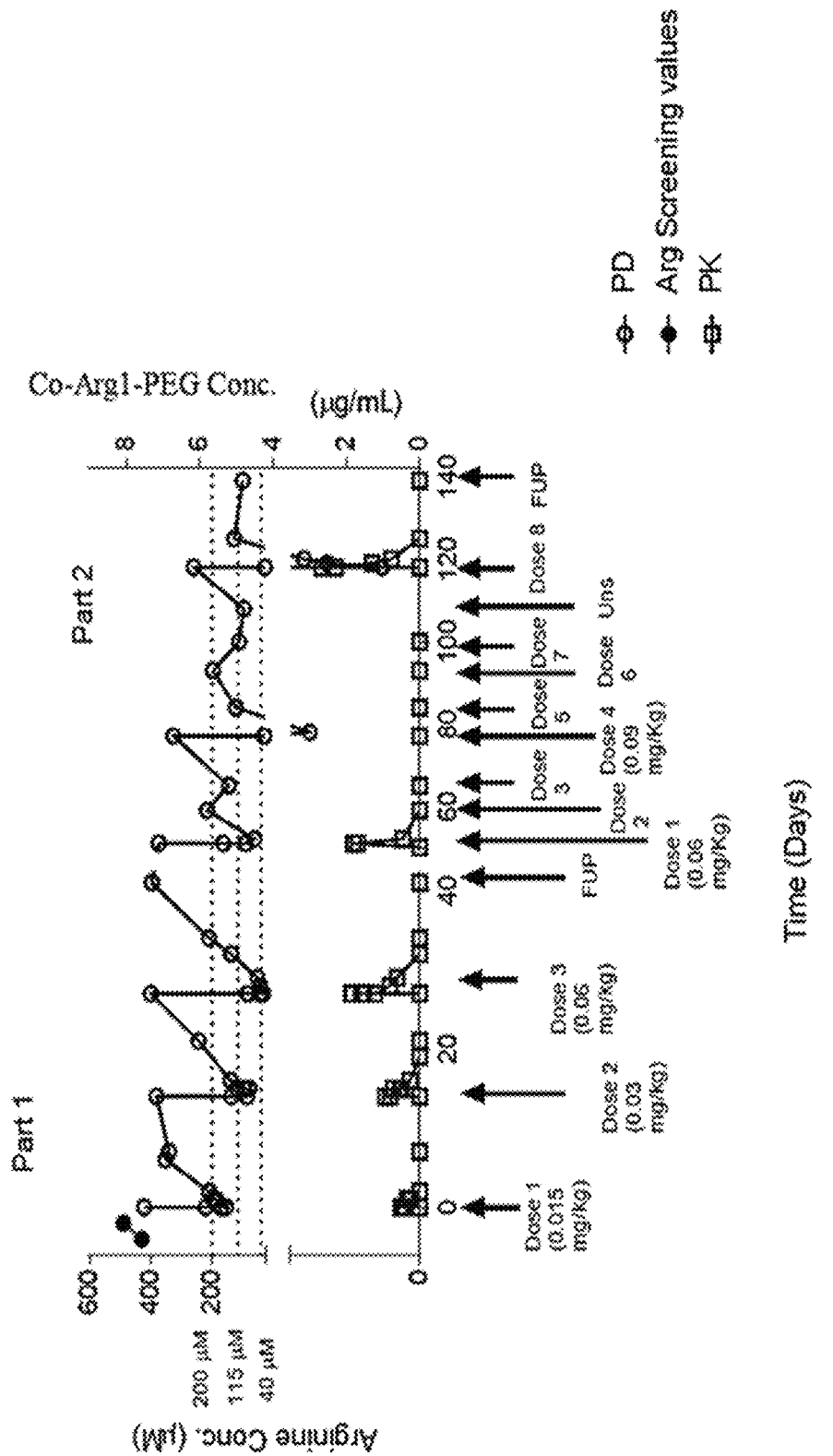
Figure 9B:
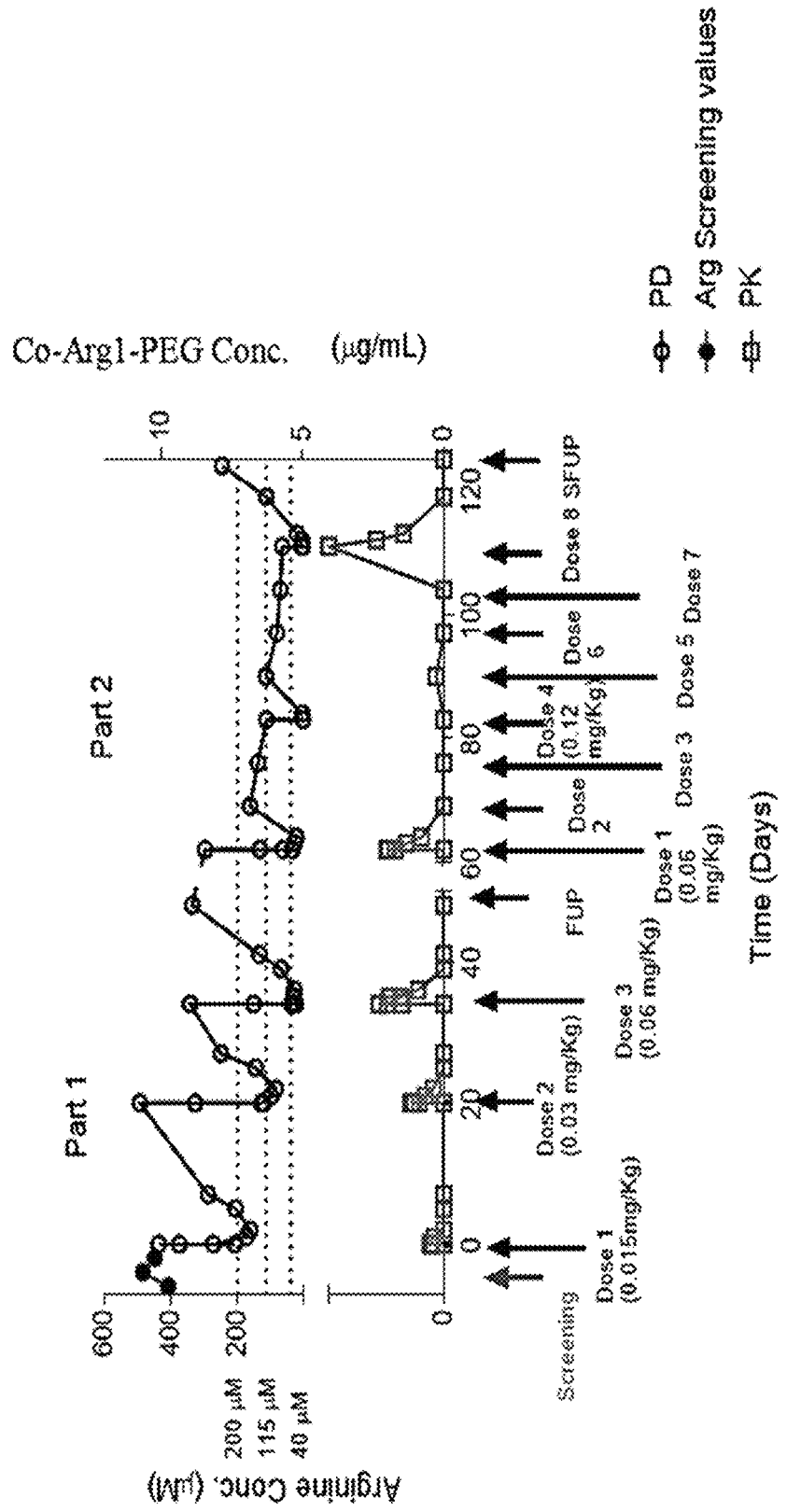
Figure 9C:
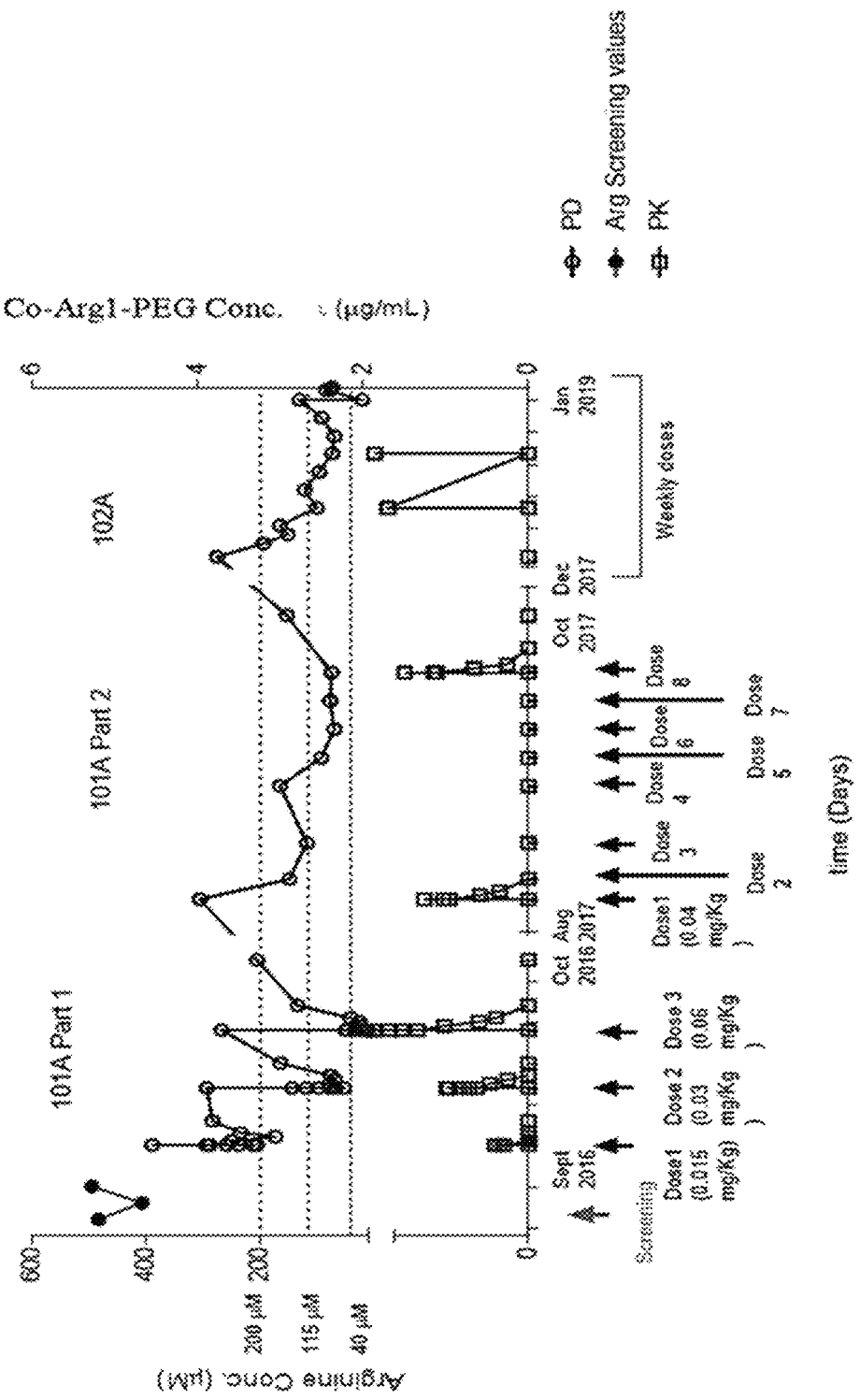

Changes in the AUCs ($AUC_{0-168}$, $AUC_{0-\infty}$) appeared dose proportional across the studied dose range, noting that there no notable change between 0.06 and 0.1 mg/kg (with the data that was available; linear, FIG. 9(a); semi-log, FIG. 9(b)). Mean clearance (CL) estimates ranged from 0.789 to 1.57 mL/hr/kg in all patients and 0.776 to 1.33 mL/hr/kg in ADA negative patients. The mean volume of distribution (Vss) estimates ranged from 35.3 to 52.1 mL/kg in all patients and 32.8 to 52.1 mL/kg in ADA negative patients.

Part 1 of the study helped select an optimal (individual) starting dose for each patient for Part 2 using the observed PD (arginine) response. In Week 1 of Part 2, there was a trend for increasing mean circulating drug concentrations in all patients with escalating doses of Co-rhARG1-PEG across the dose range evaluated (linear, FIG. 9(c); semi-log, FIG. 9(e)). After the first dose of Co-rhARG1-PEG in Part 2, increases in mean $C_{max}$ appeared dose proportional in all patients. Mean (±SD) $C_{max}$ was 0.292 (N=1), 0.395 (N=1), 1.01±0.221, 1.75±0.391, 1.99 (N=1), 2.34 (N=1), and 2.87±0.626 µg/mL for Co-rhARG1-PEG dose levels of 0.015, 0.03, 0.04, 0.06, 0.09, 0.1 and 0.12 mg/kg, respectively.

In Part 2, Week 8, mean circulating drug concentrations in all patients generally increased with escalating doses of Co-rhARG1-PEG. There was no notable ADA impact in the available PK concentrations at Week 8 (linear, FIG. 9(d); semi-log, FIG. 9(f)). As a result of the data, achievement of steady state was assumed for most (13/14) patients at this time. After the 8th QW dose of Co-rhARG1-PEG, increases in mean $C_{max}$ and $AUC_{0-168}$ appeared dose proportional in all patients.

Figure 10A:
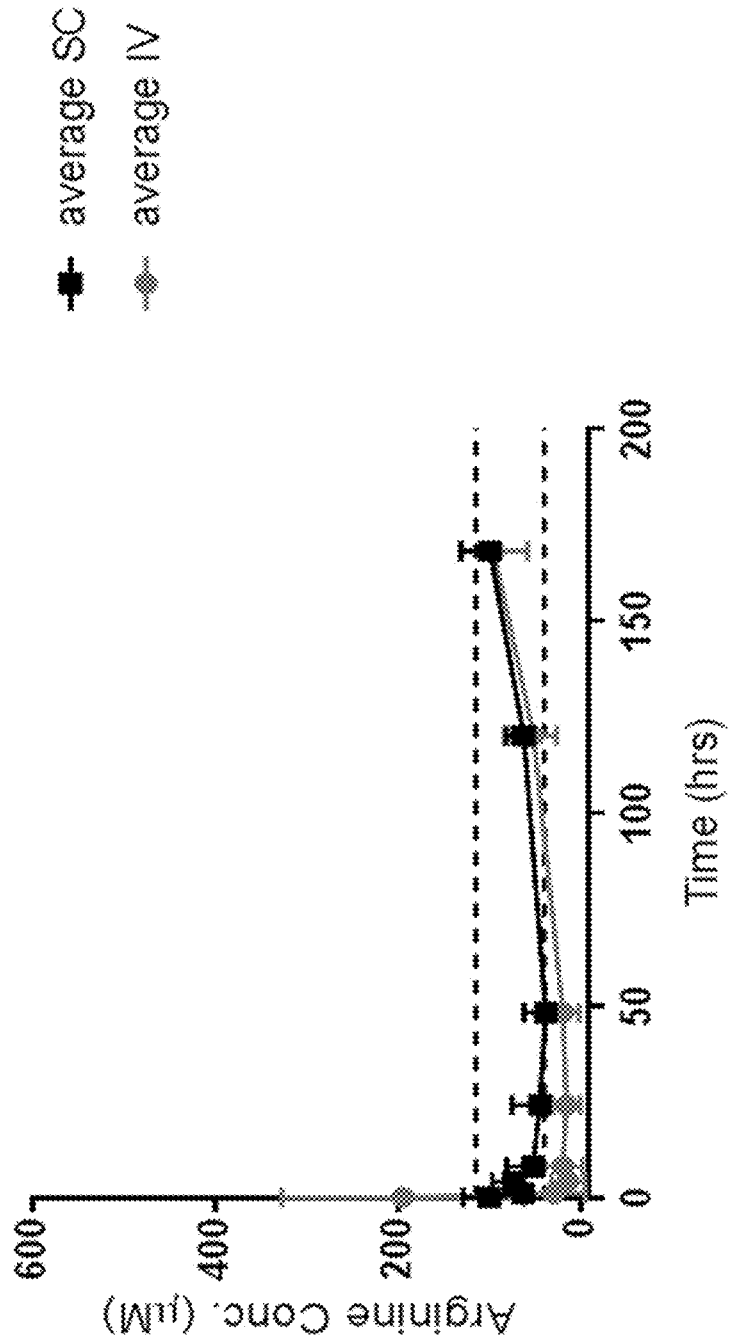
Figure 10B:
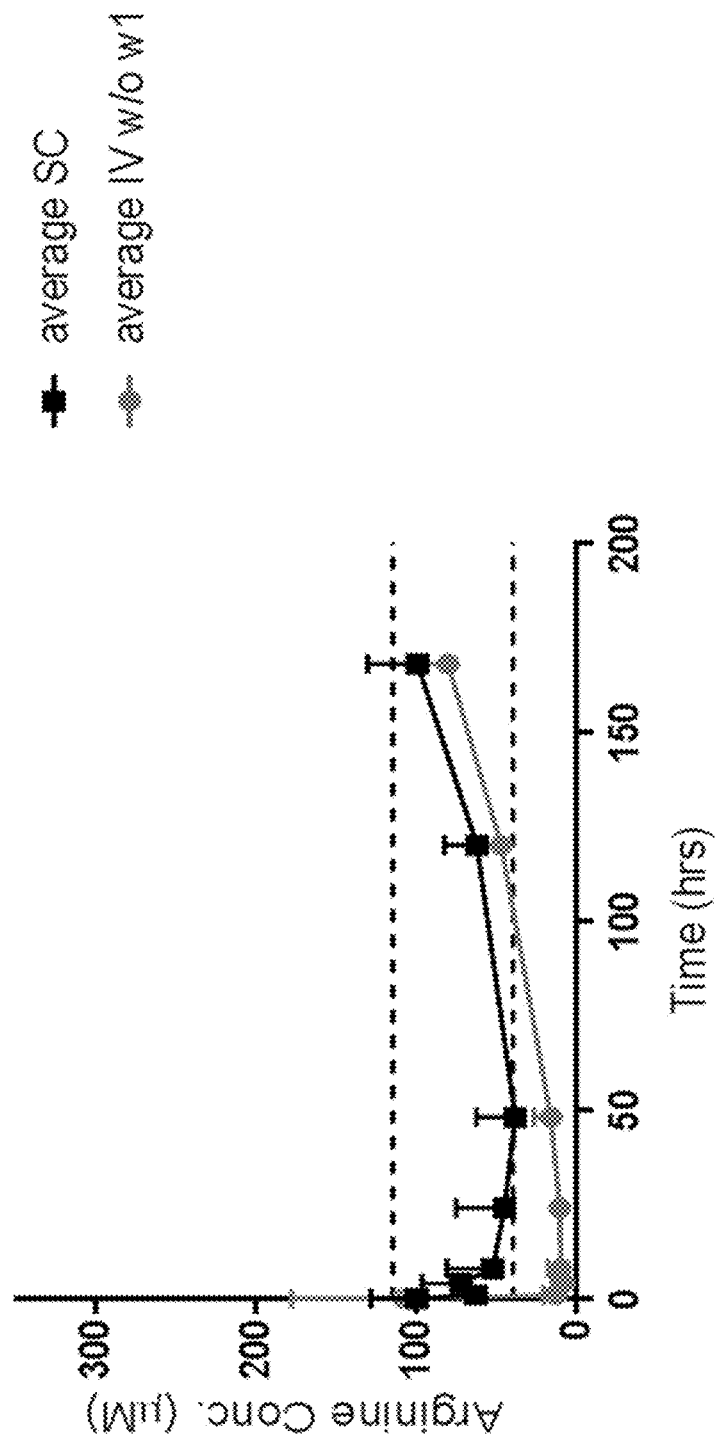

In addition to pharmacokinetic data, pharmacodynamic (arginine) data was collected (FIGS. 10(a)-10(c)). Patients with Arginase 1 deficiency were administered (weekly) QW IV doses of Co-rhARG1-PEG in Part 2 and the starting dose was selected in Part 1 based on the observed PD (arginine) response. After the first QW IV dose of Co-rhARG1-PEG, there were notable reductions in circulating arginine levels, particularly for Co-rhARG1-PEG doses at or above 0.04 mg/kg. In several instances, the individual arginine concentrations dropped below 40 µM. In addition, recoveries to starting arginine levels were incomplete in most patients at doses ≤0.04 mg/kg and just prior to administration of the second QW (weekly) Co-rhARG1-PEG dose.

Overall, exposure to Co-rhARG1-PEG generally increased and there was increased arginine suppression with escalating dose. Individualized dose optimization was undertaken in Part 1 such that there were a range of doses with varying numbers of patients per dose level in Weeks 1 and 8 of Part 2.

Example 18

Subcutaneous Administration

After Part 2 of the Phase 1/2 study of Example 17 was complete, some patients were switched from IV administration of Co-rhARG1-PEG to subcutaneous administration. Surprisingly, subcutaneous administration of Co-rhARG1-PEG gave a pharmacodynamic profile that appeared superior to IV administration. Also unexpectedly, the same formulation as for IV administration was successfully used for subcutaneous administration of Co-rhARG1-PEG.

Figure 11A:
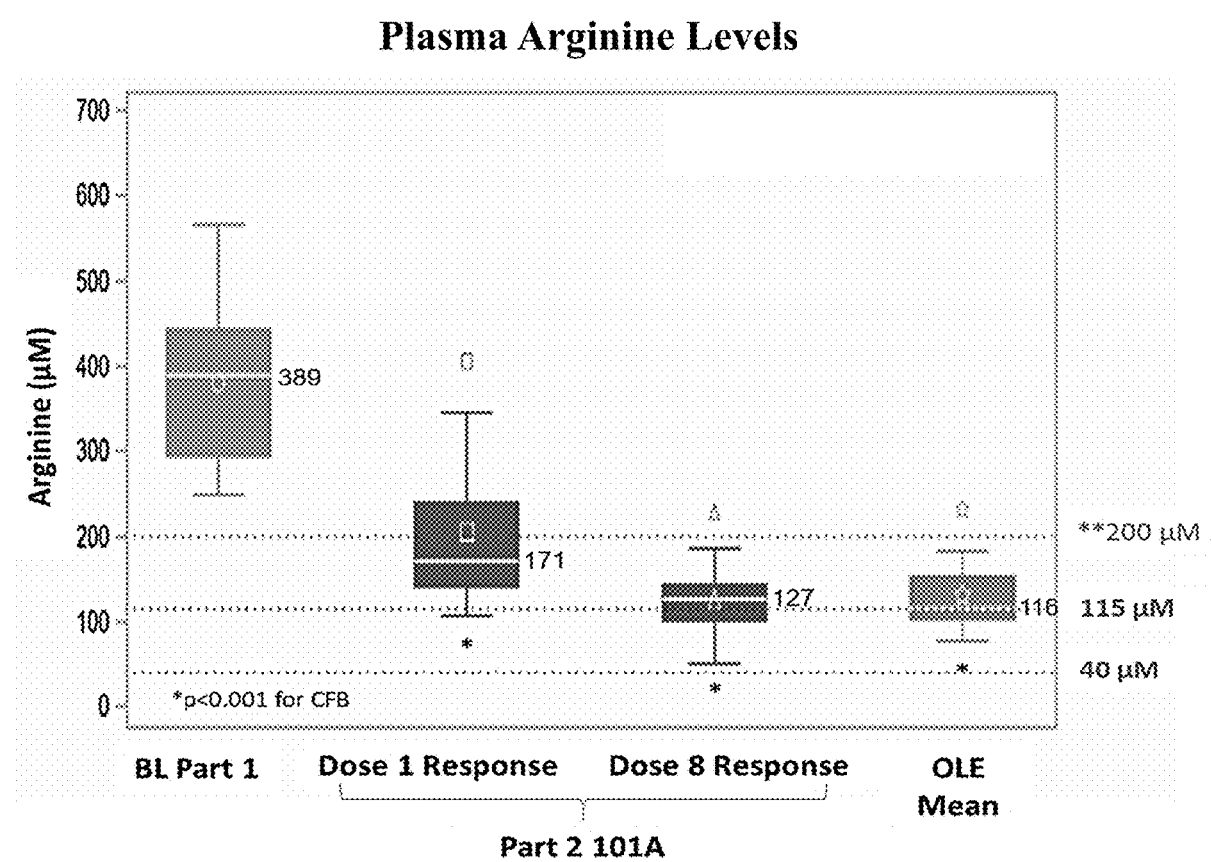
FIGS. 11(a)-11(b) show a comparison of IV and subcutaneous administration of Co-rhARG1-PEG. The preferred plasma arginine concentrations for a patient are between 40 μM and 115 μM (dotted lines). Subcutaneous administration of Co-rhARG1-PEG results in arginine concentrations within this preferred range longer than via IV administration.
Figure 11B:
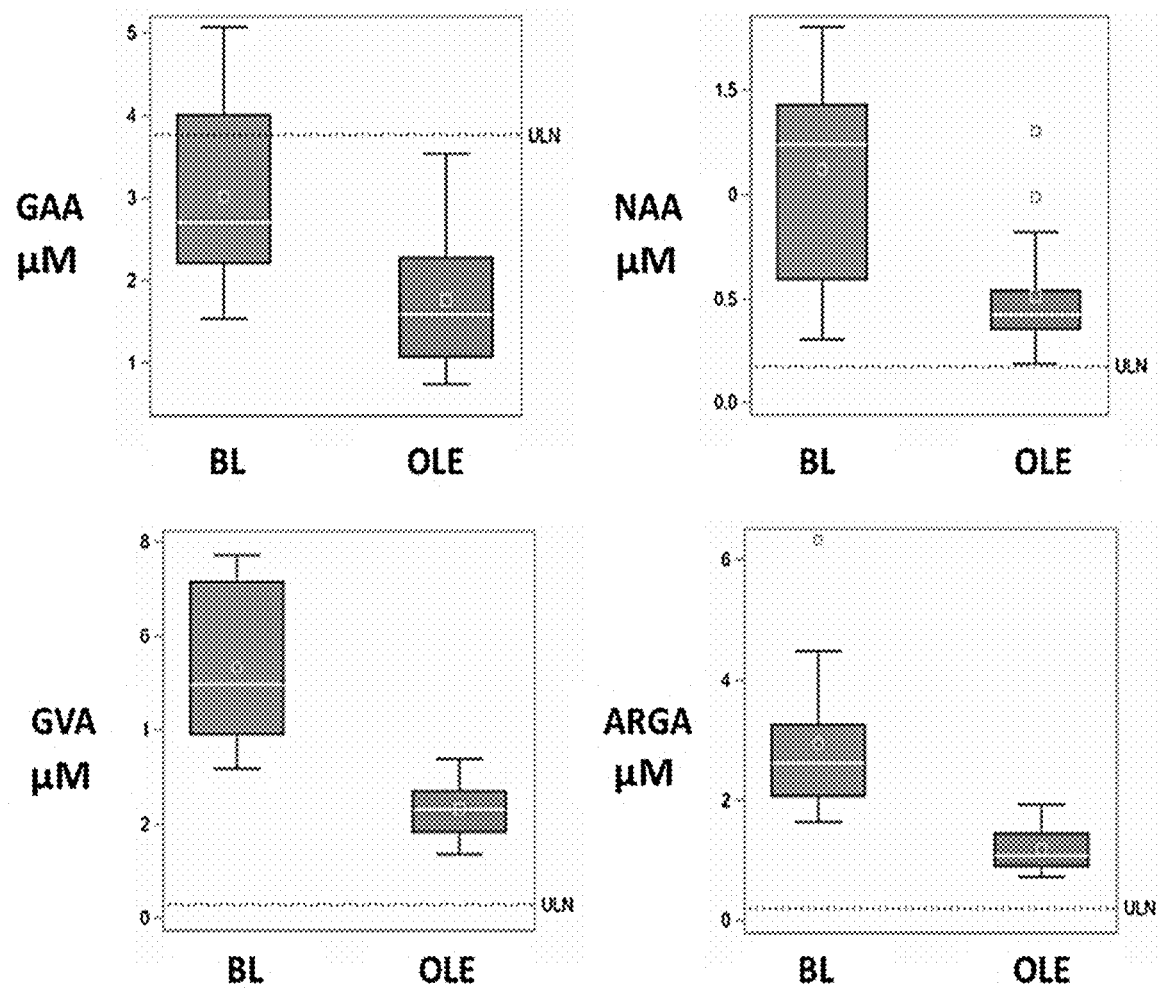

The subcutaneous administration of Co-rhARG1-PEG maintained patient arginine levels within the preferred (healthy) target range for plasma arginine concentration longer than IV administration (FIGS. 11(a)-11(b)). The preferred optimized plasma arginine concentration in a patient is in the range of about 40 µM to about 115 µM (during repeat-dose administration), with emphasis on maintaining levels below the pre-dose 150-200 µM. As can be seen in FIGS. 11(a)-11(b), subcutaneous administration of Co-rhARG1-PEG results in arginine concentrations above the lower level of 40 µM and below the upper level of 115 µM. Surprisingly, subcutaneous administration gave arginine concentrations that are entirely in the preferred range. This means the patient will stay in the appropriate plasma range of arginine concentrations until another weekly Co-rhARG1-PEG dose is received.

Example 19

Pharmacodynamic and Clinical Responses from Phase 1/2 Clinical Study and Open Label Extension 16 patients (11 paediatric and 5 adult) were enrolled into 101A Part 1 and 15 patients advanced into 101A Part 2. 2 patients withdrew from the trial for personal reasons (1 patient after Part 1 dose 3 and 1 patient after Part 2 dose 3). All 14 patients completing 101A Part 2 advanced into the OLE trial.

Baseline characteristics for the patients are shown in Table 15.

TABLE 15

Baseline Characteristics

| | |
|---|---|
| Age, years, median (range) | 15 (5-31) |
| Female, n (%) | 11 (69) |
| Arginine, µM, median (range) | 389 (238-566) |
| Ammonia, µM, median (range) | 38 (9-77) |
| ALT (U/L), median (range) | 34 (15-171) |
| ARG1 mutation, n (%) | 11 (68.8) |
| Homozygotes | 5 (31.2) |
| Compound Heterozygotes | |

Figure 12A:
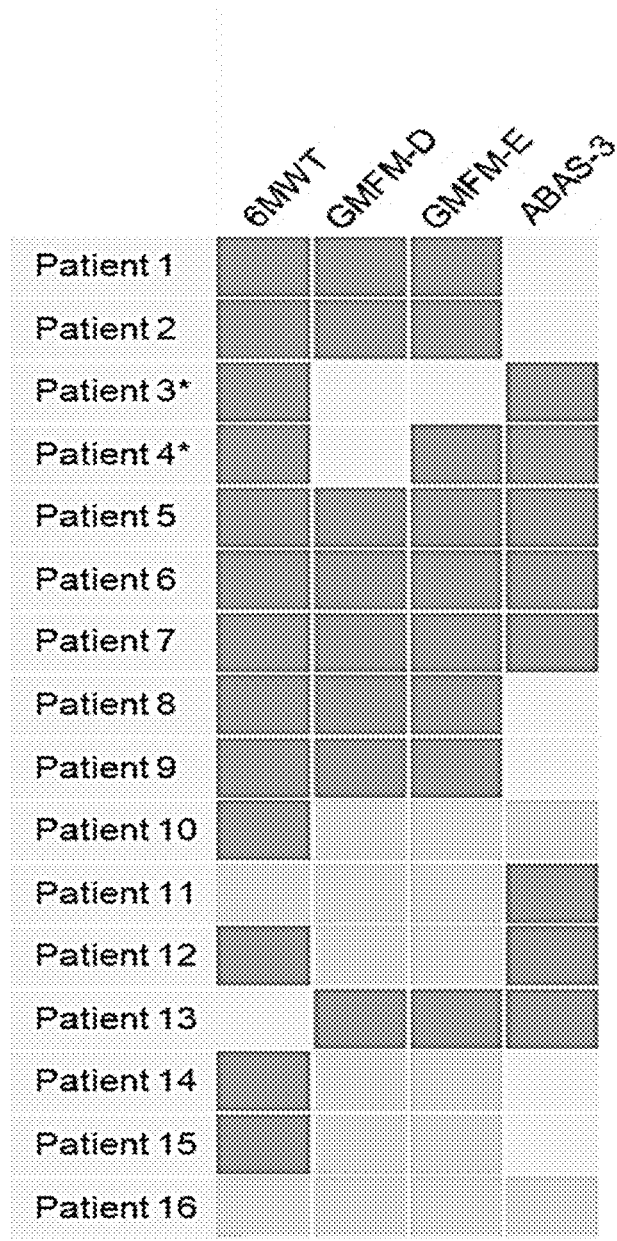
FIGS. 12(a)-12(b) show plasma arginine and plasma guanidino compound levels after administration of Co-rhARG1-PEG.
Figure 12B:
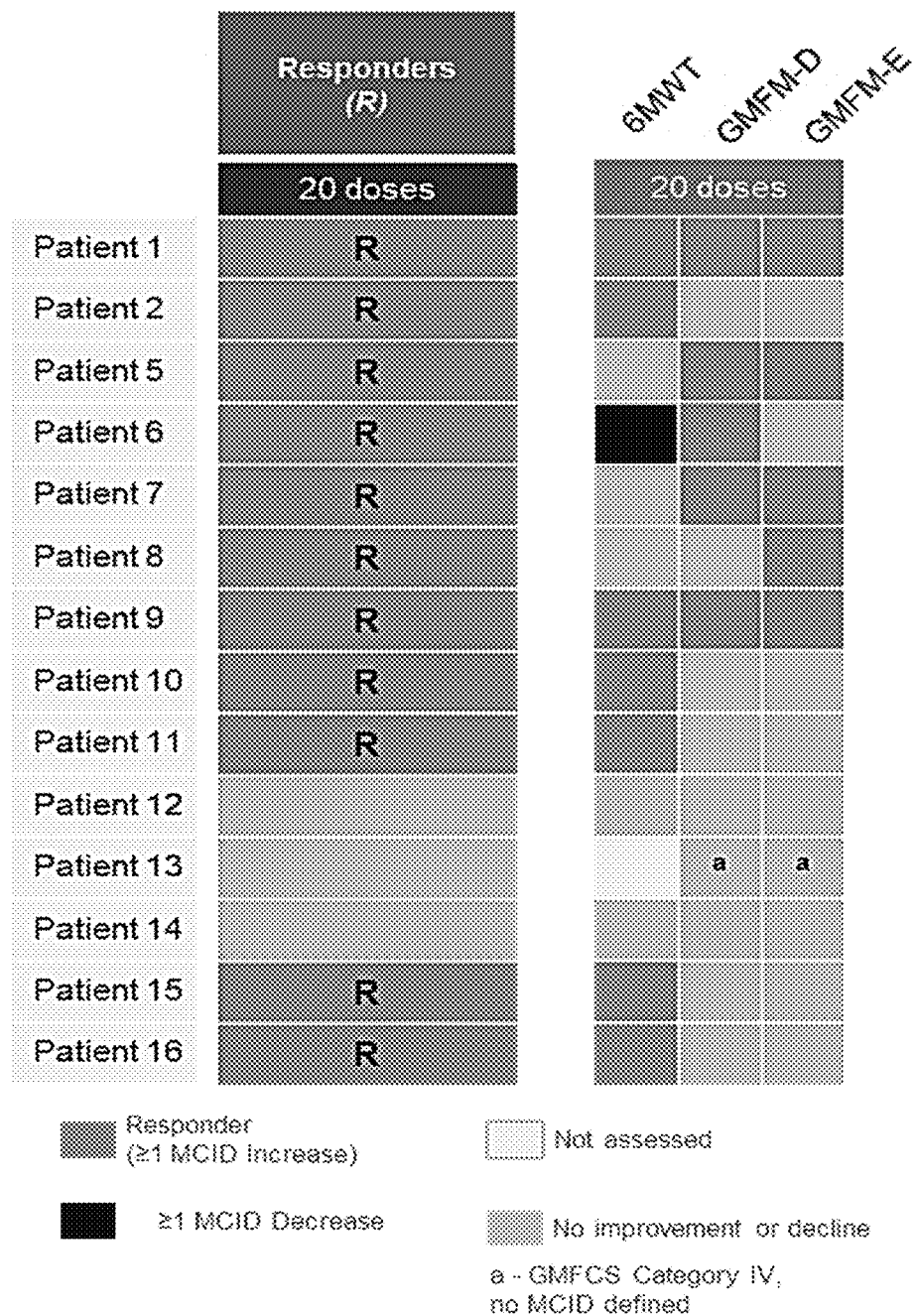

An analysis of plasma arginine and guanidino compound levels found marked and sustained reductions in plasma arginine levels (FIG. 12(a)) were demonstrated with a median reduction of 274 µM from baseline after 20 doses of pegzilarginase. Reductions in plasma arginine from baseline to dose 1, dose 8, and OLE were statistically significant (p<0.001). Plasma arginine reductions were accompanied by decreases in plasma guanidino compound (GC) levels. FIG. 12(b) shows plasma levels for guanidinoacetic acid (GAA), N-α-acetyl-L-arginine (NAA), α-keto-δ-guanidinovaleric acid (GVA) and argininic acid (ARGA) at baseline and the reduction of plasma GC levels during the OLE.

Figure 13A:
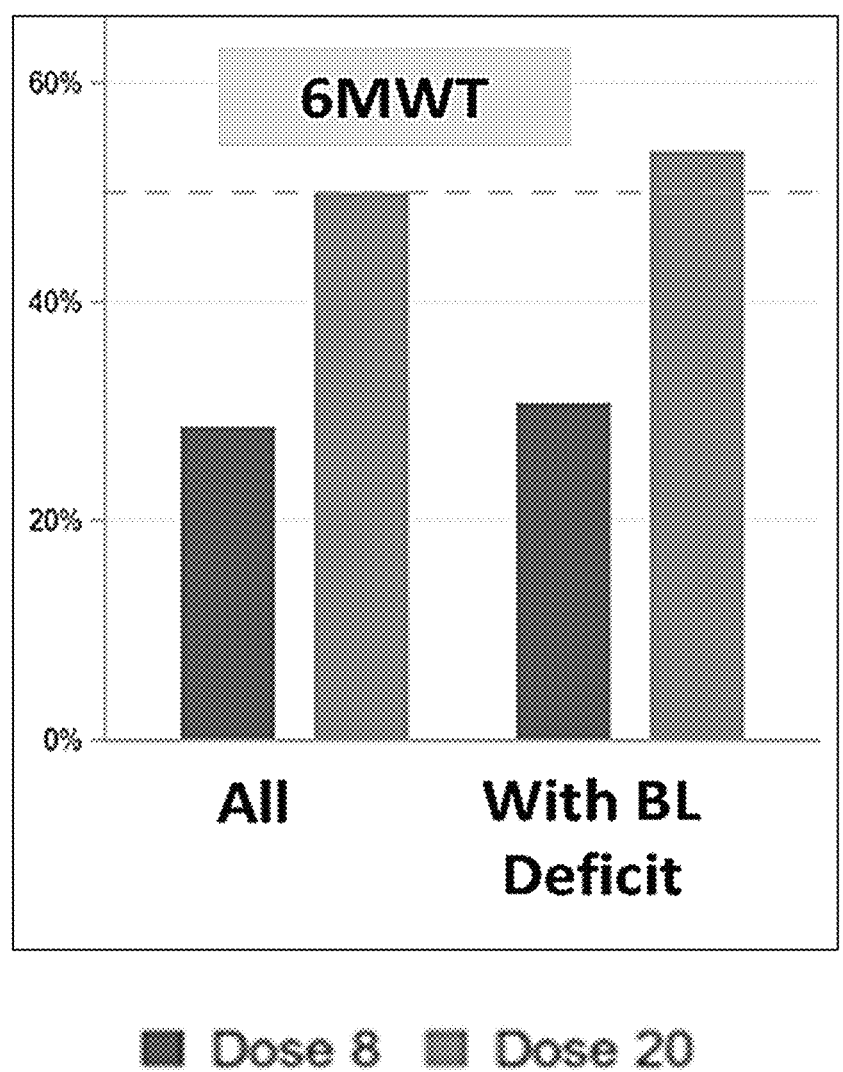
FIGS. 13(a)-13(b) show the baseline deficit and responses for clinical outcomes.

15 of 16 patients completed all mobility assessments at baseline (patient 13 was confined to a wheelchair) (FIG. 13(a)). Deficits were defined as: 6MWT: less than the lower 5$^{th}$ percentile; GMFM Part D: <35 of 39; GMFM Part E: <68 of 72; ABAS-3: ≤85. 88% (14 of 16) of patients had at least one mobility deficit at baseline; 88%, 50% and 56% of the 16 patients were classified as having a baseline deficit in the 6MWT, GMFM Part D and GMFM Part E, respectively. Adaptive behaviour ABAS-3 assessments were available for 10 patients at baseline. 6 patients were not tested for technical reasons, including constraints due to language, age and cognitive impairment 8 of 10 (80%) patients had baseline deficiencies in 1 or more domains assessed by ABAS-3.

Figure 13B:
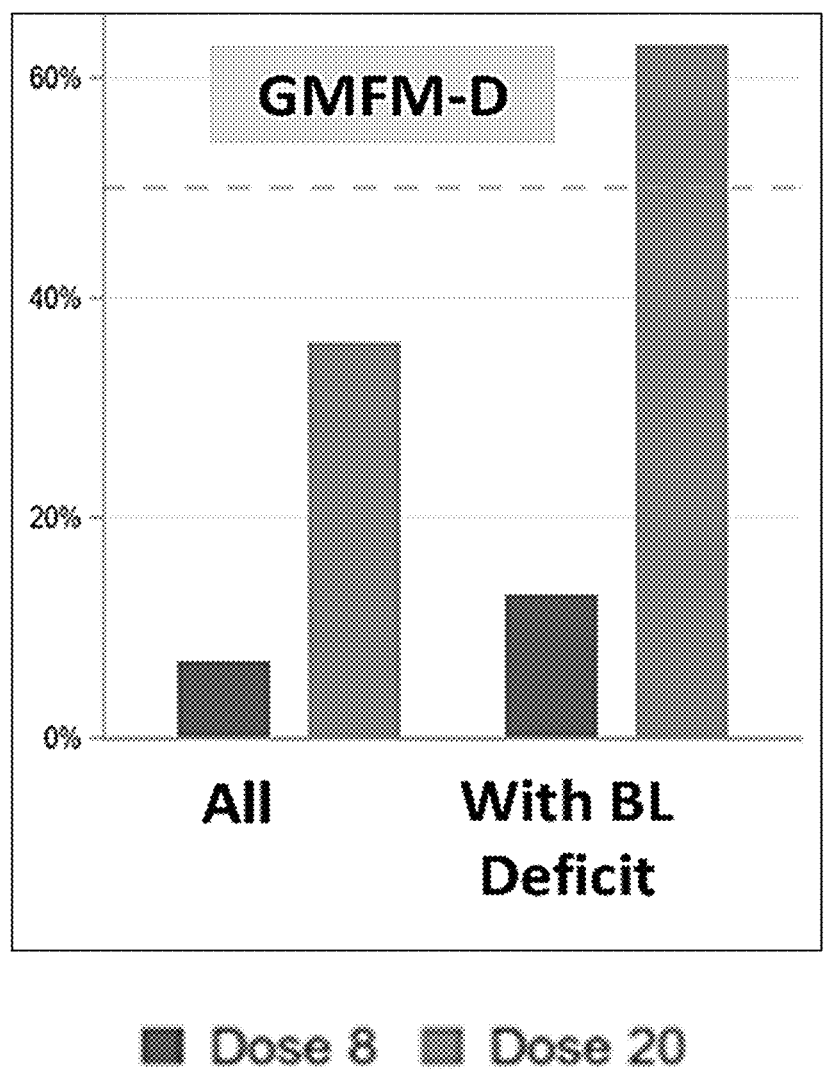
Figure 13C:
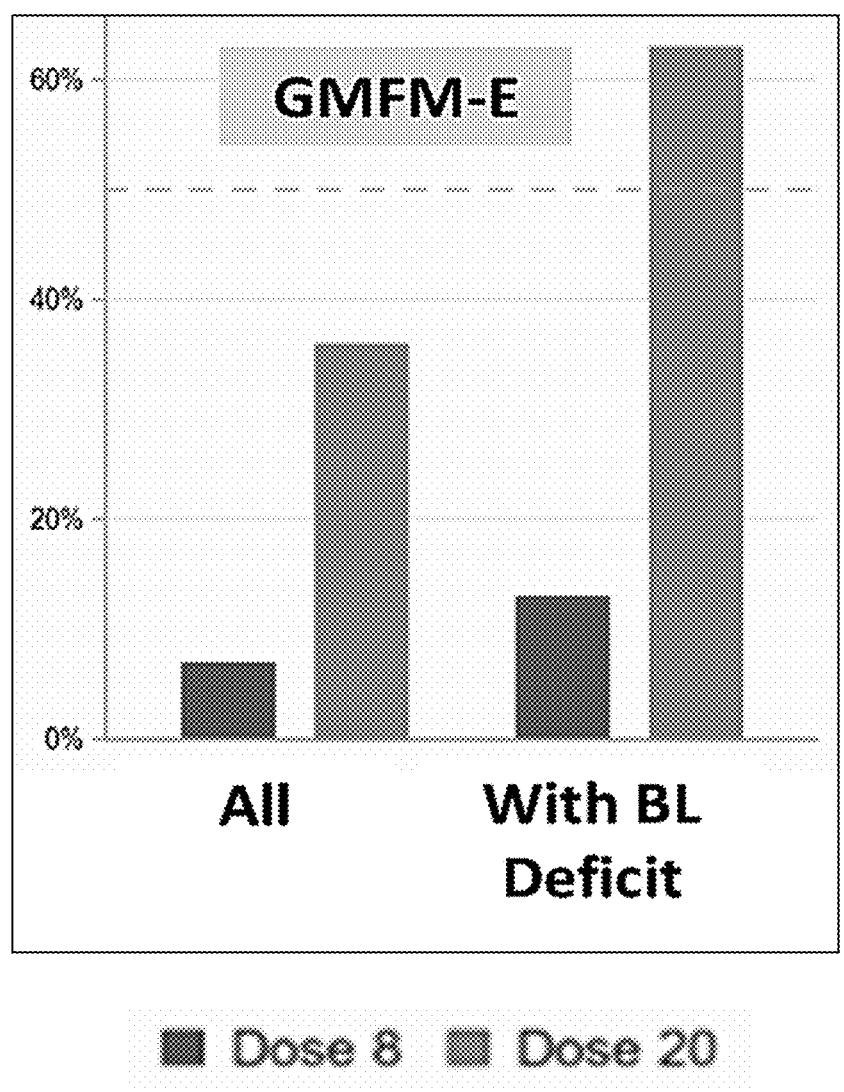
Figure 14:
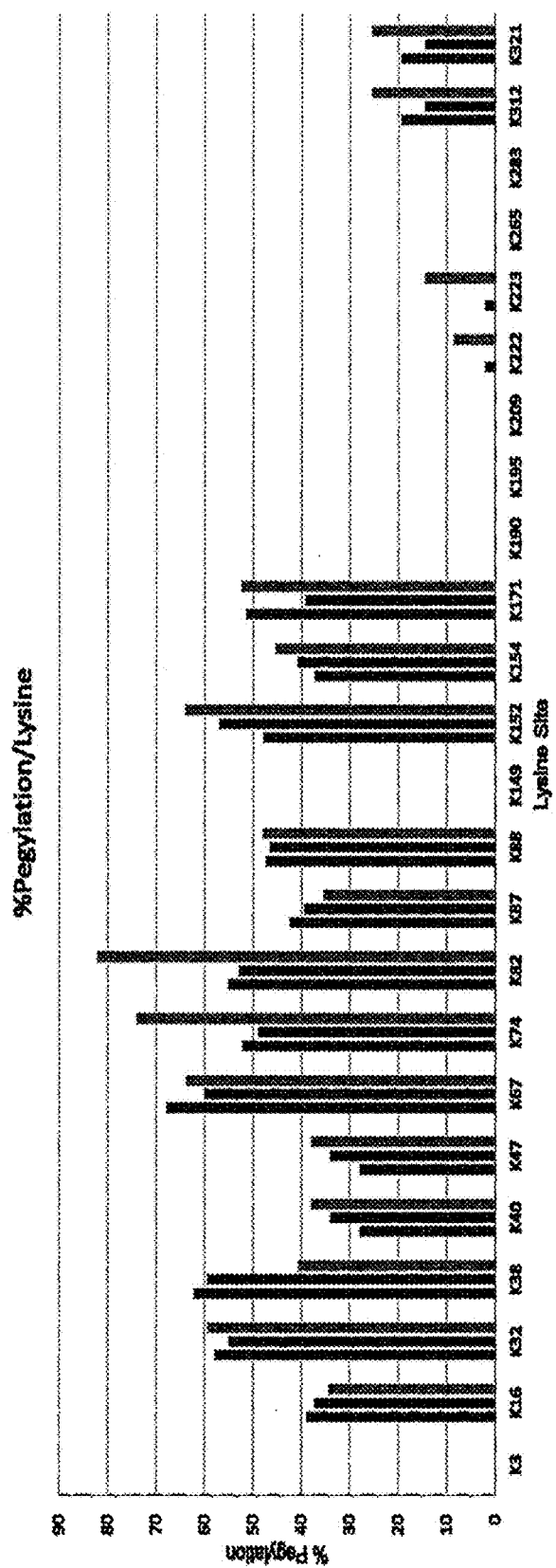
FIGS. 14(a)-14(c) show the time-dependent improvements in 6MWT, GMFM-D and GMFM-E.

The overall clinical response showed that 11 of 14 patients (79%) were defined as responders at dose 20 based on a ≥1 MCID improvement in at least one of the 6MWT, GMFM-D or GMFM-E assessments (FIG. 13(b)). 20-dose data demonstrated that 6MWT, GMFM-D, and GMFM-E are sufficiently sensitive to change for capturing clinical benefit in ARG1-D patients. The percentage of overall responders increased substantially from dose 8 to dose 20. All 5 patients (100%) who reached dose 44 maintained their dose 20 overall clinical response status as responders.

All responders for individual components had a ≥1 MCID improvement (FIG. 13(b) and FIGS. 14(a)-14(c)). For the 6MWT, 7 of 13 (54%) patients were responders on this component alone. Mean change in 6MWT was 32 meters across all patients and 66 meters in the 7 responders. For GMFM-D: 5 of 8 (63%) patients with a baseline deficit were responders on this component alone (mean MCID 1.84, range 1.21 to 3.33). For GMFM-E: 5 of 8 (63%) patients with a baseline deficit were responders on this component alone (mean MCID 4.79, range 1.67 to 8.33). The percentages of responders for the individual mobility components were substantially greater at dose 20 relative to dose 8.

Data from all patients following 20 doses of pegzilarginase demonstrated marked and sustained reductions in plasma arginine, improvements in important disease manifestations, and a clinical responder rate of 79%. The Phase1/2 and OLE trials demonstrate the value of utilizing the 6MWT, GMFM-D, or GMFM-E as tools for capturing the clinical benefit of pegzilarginase. Pegzilarginase was well tolerated and the rates of treatment-related adverse events decreased over time. The improvements in arginine control and evidence of clinical benefit following pegzilarginase treatment provide further validation of the key endpoints and design elements of the pivotal Phase 3 PEACE trial (NCT03921541).

Example 20

Phase 3 Clinical Trial Design

A randomized, double-blind, placebo-controlled Phase 3 study of the efficacy and safety of Co-rhARG1-PEG in children and adults with Arginase 1 deficiency is being performed using the Co-rhARG1-PEG produced by the methods of this invention. This trial is currently underway as Pegzilarginase Effect on Arginase 1 Deficiency Clinical Endpoints, or PEACE (CAEB1102-300A; NCT03921541). The study design for this Phase 3 trial is shown in FIG. 17.

Key Inclusion Criteria a. Aged ≥2 years with a diagnosis of ARG1-D and with plasma arginine levels ≥250 µmol/L to allow statistical testing of the proportion of patients who achieve plasma arginine below medical guidance of 200 µmol/L b. Able to maintain a stable consistent diet for the duration of the blinded period c. Able to remain on stable doses of ammonia scavengers, anti-epileptic therapy and/or medications for spasticity during the blinded period d. Able to perform and successfully complete clinical assessments and must have a baseline deficit in one of the components of the secondary clinical response endpoint as shown in Table 16.

Key Exclusion Criteria a. Hyperammonaemic episode requiring hospitalisation within 6 weeks before starting treatment b. Active infection within 3 weeks prior to receiving the first pegzilarginase dose c. Extreme mobility deficit, defined as inability to be assessed on the Gillette Functional Assessment Questionnaire (GFAQ) or a score of 1 on the GFAQ (cannot take any steps at all)

d. Participated in previous interventional studies with pegzilarginase or currently participating in other clinical trials e. History of hypersensitivity to polyethylene glycol

TABLE 16

Definition of Baseline Deficits for Key Clinical Response Endpoints

| Assessment | Component | Definition of Baseline Deficit |
|---|---|---|
| Timed walk test* | 2MWD (m) | Bottom 15th Percentile for Age and Sex |
| Gross Motor Function Measure+ | Part D | <35 of 39 |
|  | Part E | <68 of 72 |

2MWD = 2-minute walk distance;
GMFM = Gross Motor Function Measure;
Part D = standing;
Part E = walking, running, jumping;
*NIH Toolbox (US Department of Health and Human Services, Washington, DC, USA) motor domain dataset (2-minute Walk Endurance Test)

The primary endpoint of this Phase 3 trial is plasma arginine reduction (change from baseline in plasma arginine levels at week 24 based on the treatment means of change from baseline in individual patients for the active and placebo arms). Secondary endpoint measures include:

a. Clinical Response Endpoint: A clinical responder is defined as a patient with an improvement in at least one of the 2MWT, GMFM-D, or GMFM-E clinical response endpoints at Week 24 as defined in Table 17
b. Response rates for each individual component of the clinical response endpoint
c. Other clinical outcome assessments
   i. Functional Mobility Scale 5, 50, 500 meters
   ii. Gillette Functional Assessment Questionnaire (GFAQ)
   iii. Vineland Adaptive Behaviour Scales-II
d. Evaluation of safety, including immunogenicity
e. Proportion of patients with plasma arginine <200 μM and within normal range (40-115 μM)
f. characterisation the pharmacokinetic profile of pegzilarginase

TABLE 17

Clinical Response Endpoints Defining a Clinical Responder

| Assessment | Component | Definition of Response |
|---|---|---|
| 2MWT | Distance walked | Improvement by ≥ 9% |
| GMFC | Part D | Improvement by 1.5 to 3.3 points based on GMFCS |
|  | Part E | Improvement by 1.8 to 4.0 points based on GMFCS |

The total duration of the study is expected to be approximately 178 weeks per subject, including the long-term open-label extension period (3- to 4-week screening period, 24-week treatment period, followed by an open-label extension period of up to 150 weeks). Subjects will receive weekly IV infusions (approximately 30 minutes) of Co-rhARG1-PEG or volume-adjusted placebo once weekly. Dose modifications of Co-rhARG1-PEG based solely on plasma arginine values will be implemented by the unblinded pharmacist and/or physician, according to a dosing algorithm. After the first 8 weeks of the blinded long-term extension period, subjects will have the option to receive Co-rhARG1-PEG by subcutaneous administration, with investigator and sponsor approval. The initial mg/kg subcutaneous dose may be the same as the IV dose.

Subjects assigned to Co-rhARG1-PEG begin at Dose Level 2 (see Table 18 below), 0.10 mg/kg. Beginning with Visit 5, dose modifications, if required, based on plasma arginine values will be implemented by an unblinded physician, according to the following dosing algorithm:

If the plasma arginine level is >150 μM, a single 168-hour sample will be used to increase the dose by 2 dose levels (not to exceed 0.20 mg/kg) if the 2 doses prior to this sample were a) the same dose level in mg/kg, and b) consecutive (with no missed doses).

If the plasma arginine levels from 2 sequential 168-hour samples (regardless of missed doses) are both <50 μM, the dose is decreased by 1 dose level (see Table 17), not to decrease below 0.05 mg/kg.

TABLE 18

Dose Adjustments for Co-rhARG1-PEG

| Dose Level (a) | Dose |
|---|---|
| 1 (Minimum Possible Dose) | 0.05 mg/kg |
| 2 (Starting Dose) | 0.10 mg/kg |
| 3 | 0.15 mg/kg |
| 4 (Maximum Possible Dose) | 0.20 mg/kg |

(a) Pegzilarginase dosing starts at level 2. 0.10 mg/kg. Dose increases, when required, are by 2 dose levels. Dose decreases are by 1 dose level.

Statistical Considerations

The primary analysis will compare the mean decrease from baseline in plasma arginine levels in patients treated with pegzilarginase vs. placebo after 24 weekly doses, based on the average of the last four plasma arginine measurement results which satisfy strict pre-specified criteria.

Sample sizes of 10 and 20 patients randomized to placebo and pegzilarginase, respectively, achieve 98% power to demonstrate a difference in mean plasma arginine levels of 200 μM at the 0.05 significance level using a two-sided Mann-Whitney-Wilcoxon Test, assuming a common SD of 120 μM.

Additionally, this number of subjects provides more than 80% power to detect a statistically significant difference of 40% between the group proportions for the clinical response endpoint at the 0.05 significance level using a Fisher's Exact Test.

Example 21

Site-Specific PEGylation Analysis

Figure 15:
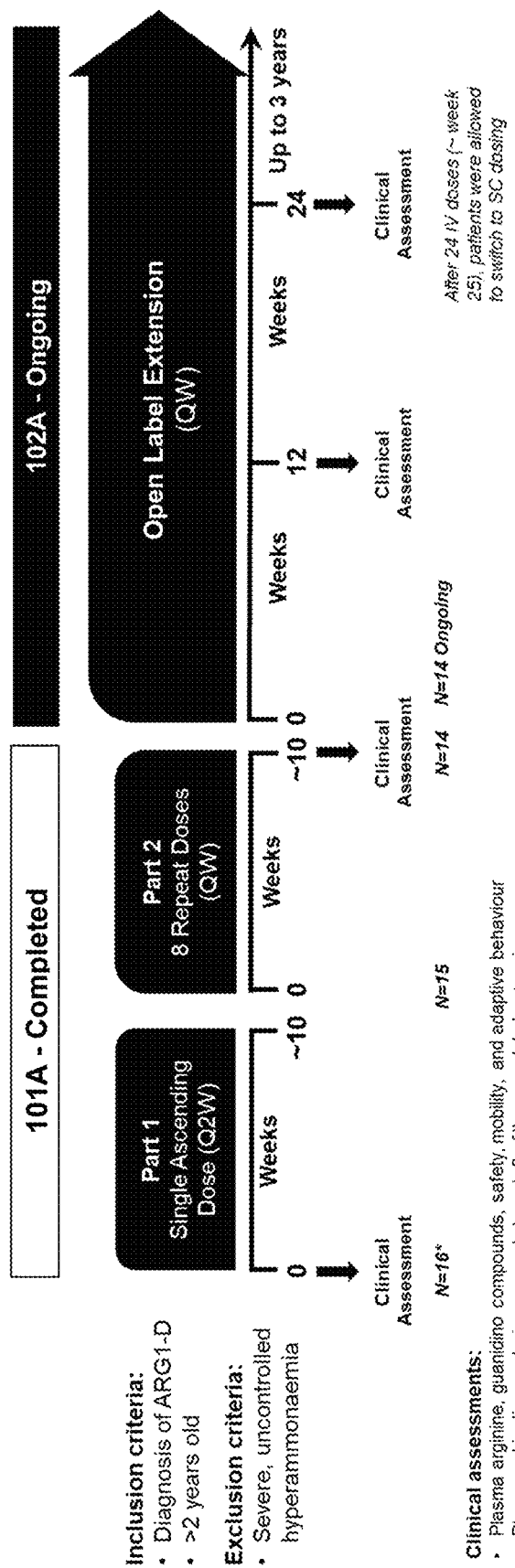
FIG. 15 shows a site-specific PEGylation analysis of different batches of Co-rhARG1-PEG.

An exemplary sites-specific PEGylation analysis is provided in FIG. 15. Three Co-rhARG1-PEG batches were analyzed. Peptide mapping was performed by denaturing Co-rhARG1-PEG Drug Substance, Co-Arginase 1 Intermediate (non-pegylated) Lots and the corresponding Reference Standards, with guanidine-HCl, reduced with DTT, and alkylated with iodoacetamide. These samples were diluted with 50 mM Tris Buffer pH 8.0. Each sample was digested with sequencing-grade trypsin for about 5 h at 37° C. The resulting peptides were resolved on a Waters Acquity BEH 300 C18 column, 2.1×150 mm, Waters C/N 186003687 using an acetonitrile gradient in 0.05% Trifluoro Acetic acid. LC-MS and MS/MS fragmentation of the peptides was obtained on a Waters Xevo G2-XS QTOF MS/MS.

As can be seen, none of the three batches had PEGylation at sites K3, K149, K190, K195, K29, K265 or K283. Also, all three batches had PEGylation at sites K16, K32, K38, K40, K47, K67, K74, K82, L87, K88, K152, K154, K171, K312 and K321. Some batches had a low frequency of PEGylation at sites K222 and K223.

Reference throughout this specification to "one embodiment," "certain embodiments," "various embodiments,"

"one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A method for producing purified recombinant cobalt-substituted human Arginase, wherein the recombinant human Arginase (rhARG) comprises an amino acid sequence that is at least 98% identical to SEQ ID NO: 1, the method comprising:

a) in a bioreactor, culturing *E. coli* cells that produce rhARG;

b) lysing the *E. coli* cells;

c) removing cell debris from the lysate;

d) loading the cell lysate on a cation exchange column;

e) eluting the rhARG with a high salt solution;

f) incubating the eluted rhARG with a cobalt salt to form cobalt-substituted rhARG (Co-rhARG);

g) applying said Co-rhARG to an anion exchange column and collecting the flow-through;

h) applying the flow-through onto a third chromatography column; and i) eluting the Co-rhARG from the third chromatography column with a high salt solution.

2. The method of claim 1, wherein up to 60 grams of rhARG is loaded onto the cation exchange column per liter of cation exchange resin.

3. The method of claim 1, wherein eluting the rhARG from the cation exchange column uses a high salt solution of up to 0.5 M salt concentration.

4. The method of claim 1, wherein eluting the rhARG from the cation exchange column uses a high salt solution of 0.1 M salt concentration.

5. The method of claim 1, wherein eluting the rhARG from the cation exchange column uses a gradient of 0.0 to 0.5 M salt concentration.

6. The method of claim 1, wherein eluting the rhARG from the cation exchange column uses a gradient of 0.0 to 0.2M salt concentration.

7. The method of claim 1, wherein the cobalt salt comprises a $Co^{2+}$ salt.

8. The method of claim 1, wherein the cobalt salt comprises $CoCl_2$.

9. The method of claim 1, wherein the third chromatography column comprises a multimodal chromatography (MMC) column.

10. The method of claim 1, further comprising reacting the rhARG or Co-rhARG with a PEGylation reactant to provide a PEGylated protein.

11. The method of claim 10, wherein the PEGylated protein comprises one or more of PEGylated amino acid residues at K16, K32, K38, K40, K47, K67, K74, K82, L87, K88, K152, K154, K171, K222, K223, K312 and K321.

12. The method of claim 11, wherein the PEGylated protein comprises one or more of 15% to 60% of K16, 35% to 80% of K32, 20% to 85% of K38, 10% to 60% of K40, 10% to 60% of K47, 40% to v 90% of K67, 30% to 95% of K74, 30% to v 98% of K82, 15% to 65% of K87, 25% to 70% of K88, 25% to 85% of K152, 15% to 65% of K154, 20% to 75% of K171, 0% to 30% of K222, 0% to 35% of K223, 0% to 45% of K312, and 0% to 45% of K321 is PEGylated.

13. The method of claim 10, wherein the PEGylated protein comprises PEGylated amino acid residues at least at K16, K32, K38, K40, K47, K67, K74, K82, L87, K88, K152, K154, K171, K312 and K321.

14. The method of claim 10, wherein the PEGylated protein does not have PEGylated amino acid residues at K3, K149, K190, K195, K29, K265 and K283.

15. A method for producing purified PEGylated recombinant cobalt-substituted human Arginase, wherein the recombinant human Arginase (rhARG) comprises an amino acid sequence that is at least 98% identical to SEQ ID NO: 1, the method comprising:

a) in a bioreactor, culturing E. coli that produce rhARG;

b) lysing the E. coli cells;

c) removing cell debris from the lysate;

d) loading the cell lysate on a cation exchange column;

e) eluting the rhARG with a high salt solution;

f) incubating the eluted rhARG with 10 mM $CoCl_2$ to form cobalt-substituted rhARG (Co-rhARG);

g) applying the Co-rhARG to an anion column and collecting the flow-through;

h) applying the flow-through onto a multimodal chromatography (MMC) column;

i) eluting the Co-rhARG from the MMC column with a high salt solution;

j) adding a molar excess of methoxy PEG succinimidyl carboxymethyl ester;

k) removing excess PEG.

16. A method for producing purified recombinant cobalt-substituted human Arginase, wherein the recombinant human Arginase (rhARG) comprises an amino acid sequence that is at least 98% identical to SEQ ID NO: 1, the method comprising:

a) in a bioreactor, culturing E. coli cells that produce rhARG at 36° C. to 38° C., and pH of between 7.0 and 7.4, with agitation and aeration;

i) adjusting the temperature of the bioreactor to 29° C.;

ii) inducing E. coli cells to produce for rhARG;

iii) culturing the E. coli cells for 18 hours;

iv) harvesting the E. coli cells by centrifugation;

b) lysing the E. coli cells by high pressure homogenization in 25 mM HEPES at a pH of between 7.2 to 7.6, and at or below 15° C.;

c) removing cell debris from the lysate by centrifugation at or below 15° C., then filtering the lysate with a 0.8 micron filter then filtering with a 0.5 micron filter;

d) loading the cell lysate on a cation exchange column then washing the column with 25 mM HEPES, pH 7.2-7.6;

e) eluting the rhARG at room temperature with a high salt solution comprising 25 mM HEPES, 0.1M NaCl, pH 7.2-7.6;

f) incubating the eluted rhARG with 10 mM $CoCl_2$ at room temperature for 2 to 8 hours to form cobalt-substituted rhARG (Co-rhARG);

i) exchanging Co-rhARG into 50 mM Tris, pH 8.1-8.5;

g) applying the Co-rhARG to an anion exchange column and collecting the flow-through;

h) applying the flow-through onto a Capto multimodal chromatography (MMC) column;

i) eluting the Co-rhARG from the MMC column with a high salt solution comprising 50 mM Tris, 250 mM NaCl, pH 8.1-8.5.

\* \* \* \* \*

SEQUENCE LISTING

```
Sequence total quantity: 3
SEQ ID NO: 1            moltype = AA  length = 321
FEATURE                 Location/Qualifiers
source                  1..321
                        mol_type = protein
                        organism = Homo sapiens
SEQUENCE: 1
SAKSRTIGII GAPFSKGQPR GGVEEGPTVL RKAGLLEKLK EQECDVKDYG DLPFADIPND   60
SPFQIVKNPR SVGKASEQLA GKVAEVKKNG RISLVLGGDH SLAIGSISGH ARVHPDLGVI  120
WVDAHTDINT PLTTTSGNLH GQPVSFLLKE LKGKIPDVPG FSWVTPCISA KDIVYIGLRD  180
VDPGEHYILK TLGIKYFSMT EVDRLGIGKV MEETLSYLLG RKKRPIHLSF DVDGLDPSFT  240
PATGTPVVGG LTYREGLYIT EEIYKTGLLS GLDIMEVNPS LGKTPEEVTR TVNTAVAITL  300
ACFGLAREGN HKPIDYLNPP K                                            321

SEQ ID NO: 2            moltype = DNA  length = 969
FEATURE                 Location/Qualifiers
misc_feature            1..969
                        note = Codon Optimized DNA Sequence
source                  1..969
                        mol_type = other DNA
                        organism = synthetic construct
SEQUENCE: 2
atgtctgcga agagccgtac gatcggcatt attggtgcgc cgttctctaa aggtcagcca   60
cgcggtggtg tggaagaggg tccgacggtt ctgcgtaagg ccggtttatt agaaaagctg  120
aaagagcagg agtgcgacgt taaggactac ggtgacttac cattcgcgga catcccgaat  180
gatgcccgt tccaaatcgt taagaatccg cgctctgtgg gtaaagcaag cgagcagtta  240
gcaggtaagg tggccgaggt caagaaaaac ggtcgtatta gcctggtttt aggcggtgat  300
catagcttag caattggctc tatctctggt catgcccgtg tgcacccaga tttaggtgtc  360
atttgggttg acgccatac ggatatcaat acgccattaa cgaccaccag cggcaatctg  420
catggccagc cggttagctt cttactgaag gagctgaagg gtaaaattcc agatgttccg  480
ggctttagct gggtcacgcc atgtatttct gccaaggata tcgtgtacat tggcttacgt  540
gacgtcgacc caggtgagca ctacatctta aagaccctgg gtatcaagta tttcagcatg  600
acggaagtgg accgcttagg catcggcaag gtgatggagg agacgctgag ctatctgctg  660
ggccgtaaga aacgtccaat ccatctgagc ttcgatgttg acggcttaga cccgagcttt  720
acgccagcca ccggcacgcc ggtcgttggt ggtttaacgt atcgcgaagg cctgtatatc  780
acggaggaaa tctataagac gggttactg agcggtctgg acattatgga ggttaatcca  840
agcttaggta agacgccgga agaagttacc cgtaccgtta acacggcggt cgcgatcacg  900
ttagcatgtt tcggtttagc ccgcgagggc aaccataaac caattgatta tctgaatcca  960
ccgaagtga                                                          969

SEQ ID NO: 3            moltype = AA  length = 353
FEATURE                 Location/Qualifiers
source                  1..353
                        mol_type = protein
                        organism = Homo sapiens
SEQUENCE: 3
SLRGSLSRLL QTRVHSILKK SVHSVAVIGA PFSQGQKRKG VEHGPAAIRE AGLMKRLSSL   60
GCHLKDFGDL SFTPVPKDDL YNNLIVNPRS VGLANQELAE VVSRAVSDGY SCVTLGGDHS  120
LAIGTISGHA RHCPDLCVVW VDAHADINTP LTTSSGNLHG QPVSFLLREL QDKVPQLPGF  180
SWIKPCISSA SIVYIGLRDV DPPEHFILKN YDIQYFSMRD IDRLGIQKVM ERTFDLLIGK  240
RQRPIHLSFD IDAFDPTLAP ATGTPVVGGL TYREGMYIAE EIHNTGLLSA LDLVEVNPQL  300
ATSEEEAKTT ANLAVDVIAS SFGQTREGGH IVYDQLPTPS SPDESENQAR VRI         353
```